United States Patent
Cheng et al.

(10) Patent No.: US 10,968,218 B2
(45) Date of Patent: Apr. 6, 2021

(54) TETRAHYDROPYRIDOPYRIMIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Xingchun Han, Shanghai (CN); Yongguang Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/346,989

(22) PCT Filed: Oct. 31, 2017

(86) PCT No.: PCT/EP2017/077865
§ 371 (c)(1),
(2) Date: May 2, 2019

(87) PCT Pub. No.: WO2018/083081
PCT Pub. Date: May 11, 2018

(65) Prior Publication Data
US 2020/0062748 A1    Feb. 27, 2020

(30) Foreign Application Priority Data

Nov. 3, 2016 (WO) ................ PCT/CN2016/104442

(51) Int. Cl.
*C07D 471/04* (2006.01)
*A61K 31/519* (2006.01)
*A61P 31/20* (2006.01)

(52) U.S. Cl.
CPC .......... *C07D 471/04* (2013.01); *A61K 31/519* (2013.01); *A61P 31/20* (2018.01)

(58) Field of Classification Search
CPC ..... C07D 471/04; A61K 31/519; A61K 31/20
USPC ....................................... 544/279; 514/258.1
See application file for complete search history.

(56) References Cited

U.S. PATENT DOCUMENTS 9,845,322 B2 * 12/2017 Cheng ................ C07D 471/04
10,196,391 B2 * 2/2019 Cheng ................ A61K 31/506

FOREIGN PATENT DOCUMENTS

WO    2016/107832 A1    7/2016
WO    2016/177655 A1    10/2016

OTHER PUBLICATIONS

International Preliminary Report on Patentability—PCT/EP2017/077865,:pp. 1-7 (dated May 16, 2019).
"International Search Report—PCT/EP2017/077865":pp. 1-5 (dated Dec. 4, 2017).

* cited by examiner

*Primary Examiner* — Venkataraman Balasubramanian
(74) *Attorney, Agent, or Firm* — Genentech, Inc.; Richard G. A. Bone

(57) ABSTRACT

The present invention provides novel compounds having the general formula: wherein $R^1$, $R^2$ and $R^3$ are as described herein, compositions including the compounds and methods of using the compounds.

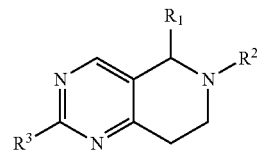

14 Claims, No Drawings

TETRAHYDROPYRIDOPYRIMIDINES FOR THE TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel tetrahydropyridopyrimidines having pharmaceutical activity, their manufacture, pharmaceutical compositions containing them and their potential use as medicaments.

The present invention relates to compounds of formula I

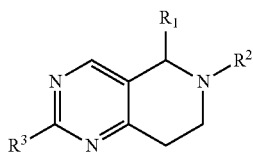

wherein $R^1$, $R^2$ and $R^3$ are as described below, or pharmaceutically acceptable salts, or enantiomers, or diastereomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. Hepatology, 46, (2007), 1759-68) and via the specific binding of HBV surface antigens (HBsAg) to the hepatocyte sodium-taurocholate cotransporting polypeptide (NTCP) receptor (Yan, H. et al. J Virol, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. J Viral Hepat, 17, (2010), 527-36). Inhibition of HBV gene expression or HBV RNA synthesis leads to the inhibition of HBV viral replication and antigens production (Mao, R. et al. PLoS Pathog, 9, (2013), e1003494; Mao, R. et al. J Virol, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. J Clin Invest, 122, (2012), 529-37; Mao, R. et al. J Virol, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. Semin Liver Dis, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. Virol J, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma. The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. Journal of Immunology (1993), 150, 4659-4671; Kondo et al. Journal of Medical Virology (2004), 74, 425-433; Fisicaro et al. Gastroenterology, (2010), 138, 682-93;). Moreover HBsAg has been reported to suppress the function of immune cells such as monocytes, dendritic cells (DCs) and natural killer (NK) cells by direct interaction (Op den Brouw et al. Immunology, (2009b), 126, 280-9; Woltman et al. PLoS One, (2011), 6, e15324; Shi et al. J Viral Hepat. (2012), 19, e26-33; Kondo et al. ISRN Gasteroenterology, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94).

A few patent applications for HBsAg inhibitors have been published, including novel dihydroquinolizinones (WO 2015/113990, WO 2015/173164), novel pyridazones and triazinones (WO2016/023877), novel 6,7-dihydrobenzo[a]quinolizin-2-one derivatives (WO/2016/071215), novel tetrahydropyridopyrimidines and tetrahydropyridopyridines (WO2016/107832) and novel 2-oxo-6,7-dihydrobenzo[a]quinolizine-3 carboxylic acid derivatives (WO 2016/128335), showing that there are some earlier exploratory efforts ongoing in this field. However, there is no commercial product approved. Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity. The present invention relates to a compound of formula I

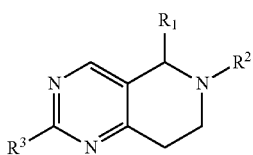

(I)

wherein
$R^1$ is hydrogen, $C_{1-6}$alkyl, $C_{1-6}$alkoxy, halo$C_{1-6}$alkyl or $C_{3-7}$cycloalkyl;
$R^2$ is phenyl or pyridinyl, wherein said phenyl or pyridinyl is unsubstituted, or substituted by one, two or three substituents independently selected from $C_{1-6}$alkyl, cyano, $C_{3-7}$cycloalkyl$C_{1-6}$alkoxy, $C_{3-7}$cycloalkyl, halo$C_{1-6}$ alkoxy, amino, $C_{1-6}$alkylamino, $(C_{1-6}$alkyl$)_2$ amino, halogen, $C_{1-6}$alkoxy, $C_{1-6}$alkoxypyrrolidinyl, $C_{1-6}$alkylcarbonylpiperazinyl, $C_{1-6}$alkylsulfonylpiperazinyl, $C_{1-6}$alkoxycarbonylpiperazinyl, morpholinyl, piperazinyl, oxopiperazinyl, oxopyrrolidinyl$C_{1-6}$alkoxy, pyrrolidinyl$C_{1-6}$alkoxy, pyrrolidinyl, oxopyrrolidinyl, tetrahydrofuranyl$C_{1-6}$alkoxy and tetrahydrofuranyl;
$R^3$ is imidazolyl, oxazolyl, pyrazolyl, thiazolyl or triazolyl, wherein said imidazolyl, oxazolyl, pyrazolyl, thiazolyl or triazolyl is unsubstituted, or substituted by $C_{1-6}$alkyl, halogen, halo$C_{1-6}$alkyl, $C_{3-7}$cycloalkyl, $C_{1-6}$alkoxy, halo$C_{1-6}$alkoxy or phenyl$C_{1-6}$alkyl;
or pharmaceutically acceptable salts, or enantiomers, or diastereomers thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl. More articular "$C_{1-6}$alkyl" groups are methyl and ethyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl. More particular "$C_{3-7}$cycloalkyl" group is cyclopropyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "$C_{1-6}$alkoxy" groups are methoxy, ethoxy and propoxy. More particular "$C_{1-6}$alkoxy" groups are methoxy and ethoxy.

The term "halogen" means fluorine, chlorine, bromine or iodine.

The term "halo$C_{1-6}$alkoxy" denotes a $C_{1-6}$alkoxy group wherein at least one of the hydrogen atoms of the $C_{1-6}$alkoxy group has been replaced by same or different halogen atoms, particularly fluoro atoms. Examples of halo$C_{1-6}$alkoxyl include monofluoro-, difluoro- or trifluoro-methoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "halo$C_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy. More particular "halo$C_{1-6}$alkoxy" group is 2,2-difluoroethoxy.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero$C_{3-7}$cycloalkyl.

The term "$C_{1-6}$alkylsulfonyl" denotes a group —SO$_2$—$C_{1-6}$alkyl, wherein $C_{1-6}$alkyl group is defined above. Examples of $C_{1-6}$alkylsulfonyl include methylsulfonyl and ethylsulfonyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I. Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

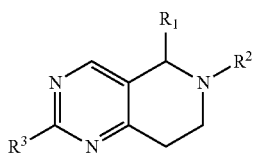

wherein

R$^1$ is hydrogen, C$_{1-6}$alkyl, C$_{1-6}$alkoxy, haloC$_{1-6}$alkyl or C$_{3-7}$cycloalkyl;

R$^2$ is phenyl or pyridinyl, wherein said phenyl or pyridinyl is unsubstituted, or substituted by one, two or three substituents independently selected from C$_{1-6}$alkyl, cyano, C$_{3-7}$cycloalkylC$_{1-6}$alkoxy, C$_{3-7}$cycloalkyl, haloC$_{1-6}$ alkoxy, amino, C$_{1-6}$alkylamino, (C$_{1-6}$alkyl)$_2$amino, halogen, C$_{1-6}$alkoxy, C$_{1-6}$alkoxypyrrolidinyl, C$_{1-6}$alkylcarbonylpiperazinyl, C$_{1-6}$alkylsulfonylpiperazinyl, C$_{1-6}$alkoxycarbonylpiperazinyl, morpholinyl, piperazinyl, oxopiperazinyl, oxopyrrolidinylC$_{1-6}$alkoxy, pyrrolidinylC$_{1-6}$alkoxy, pyrrolidinyl, oxopyrrolidinyl, tetrahydrofuranylC$_{1-6}$alkoxy and tetrahydrofuranyl;

R$^3$ is imidazolyl, oxazolyl, pyrazolyl, thiazolyl or triazolyl, wherein said imidazolyl, oxazolyl, pyrazolyl, thiazolyl or triazolyl is unsubstituted, or substituted by C$_{1-6}$alkyl, halogen, haloC$_{1-6}$alkyl, C$_{3-7}$cycloalkyl, C$_{1-6}$alkoxy, haloC$_{1-6}$alkoxy or phenylC$_{1-6}$alkyl;

or pharmaceutically acceptable salts, or enantiomers, or diastereomers thereof.

A further embodiment of the present invention is (ii) a compound of formula I, wherein R$^1$ is hydrogen or C$_{1-6}$alkyl;

R$^2$ is phenyl or pyridinyl, wherein said phenyl or pyridinyl is substituted by one, two or three substituents independently selected from C$_{3-7}$cycloalkylC$_{1-6}$alkoxy, haloC$_{1-6}$alkoxy, (C$_{1-6}$alkyl)$_2$amino, halogen, C$_{1-6}$alkoxy, C$_{1-6}$alkoxypyrrolidinyl, C$_{1-6}$alkylsulfonylpiperazinyl, morpholinyl, oxopiperazinyl, oxopyrrolidinylC$_{1-6}$alkoxy, pyrrolidinyl and tetrahydrofuranylC$_{1-6}$alkoxy;

R$^3$ is imidazolyl, oxazolyl, pyrazolyl, thiazolyl or triazolyl, wherein said imidazolyl, oxazolyl, pyrazolyl, thiazolyl or triazolyl is unsubstituted or substituted by C$_{1-6}$alkyl or phenylC$_{1-6}$alkyl;

or pharmaceutically acceptable salts, or enantiomers, or diastereomers thereof.

Another embodiment of the present invention is (iii) a compound of formula I, wherein, R$^1$ is hydrogen or methyl;

R$^2$ is phenyl or pyridinyl, wherein said phenyl or pyridinyl substituted by one, two or three substituents independently selected from cyclopropylmethoxy, difluoroethoxy, dimethylamino, fluoro, methoxy, methoxypyrrolidinyl, methylsulfonylpiperazinyl, morpholinyl, oxopiperazinyl, oxopyrrolidinylpropoxy, pyrrolidinyl and tetrahydrofuranylmethoxy;

R$^3$ is imidazolyl, oxazolyl, pyrazolyl, thiazolyl or triazolyl, wherein said imidazolyl, oxazolyl, pyrazolyl, thiazolyl or triazolyl is unsubstituted or substituted by methyl or benzyl;

or pharmaceutically acceptable salts, or enantiomers, or diastereomers thereof.

A further embodiment of the present invention is (iv) a compound of formula I, or pharmaceutically acceptable salts, or enantiomers, or diastereomers thereof, wherein R$^1$ is C$_{1-6}$alkyl, and all remaining substituents have the significances given herein before.

A further embodiment of the present invention is (v) a compound of formula I, or pharmaceutically acceptable salts, or enantiomers, or diastereomers thereof, wherein R$^1$ is methyl, and all remaining substituents have the significances given herein before.

A further embodiment of the present invention is (vi) a compound of formula I, or pharmaceutically acceptable salts, or enantiomers, or diastereomers thereof, wherein R$^2$ is pyridinyl substituted by two substituents independently selected from C$_{3-7}$cycloalkylC$_{1-6}$alkoxy, (C$_{1-6}$alkyl)$_2$amino, halogen, C$_{1-6}$alkoxy, C$_{1-6}$alkoxypyrrolidinyl, C$_{1-6}$alkylsulfonylpiperazinyl, oxopiperazinyl, pyrrolidinyl and tetrahydrofuranylC$_{1-6}$alkoxy; and all remaining substituents have the significances given herein before.

A further embodiment of the present invention is (vii) a compound of formula I, or pharmaceutically acceptable salts, or enantiomers, or diastereomers thereof, wherein R$^2$ is fluoro(methoxy)pyridinyl, difluoropyridinyl, fluoro(dimethylamino)pyridinyl, fluoro(pyrrolidinyl)pyridinyl, fluoro(methylsulfonylpiperazinyl)pyridinyl, fluoro(methoxypyrrolidinyl)pyridinyl, fluoro(oxopiperazinyl)pyridinyl, fluoro(cyclopropylmethoxy)pyridinyl, fluoro(tetrahydrofuranylmethoxy)pyridinyl, fluoro(tetrahydrofuranylmethoxy)pyridinyl or methoxy(methoxypyrrolidiny)pyridinyl; and all remaining substituents have the significances given herein before.

A further embodiment of the present invention is (viii) a compound of formula I, or pharmaceutically acceptable salts, or enantiomers, or diastereomers thereof, wherein R$^3$ is C$_{1-6}$alkylimidazolyl, thiazolyl or triazolyl; and all remaining substituents have the significances given herein before.

Another embodiment of the present invention is (ix) a compound of formula I, or pharmaceutically acceptable salts, or enantiomers, or diastereomers thereof, $R^3$ is methylimidazolyl, thiazolyl or triazolyl; and all remaining substituents have the significances given herein before.

Particular compounds of formula I according to the invention are the following:

6-(3,4-Difluoro-5-methoxy-phenyl)-2-(1-methylimidazol-2-yl)-7,8-dihydro-5H-pyrido[4,3-d]pyrimidine;

6-(6-Fluoro-4-methoxy-2-pyridyl)-5-methyl-2-(triazol-1-yl)-7,8-dihydro-5H-pyrido[4,3-d]pyrimidine;

6-(6-Fluoro-4-methoxy-2-pyridyl)-5-methyl-2-(triazol-2-yl)-7,8-dihydro-5H-pyrido[4,3-d]pyrimidine;

2-[6-(6-Fluoro-4-methoxy-2-pyridyl)-5-methyl-7,8-dihydro-5H-pyrido[4,3-d]pyrimidin-2-yl]oxazole;

4-[6-(6-Fluoro-4-methoxy-2-pyridyl)-5-methyl-7,8-dihydro-5H-pyrido[4,3-d]pyrimidin-2-yl]thiazole;

2-[6-(6-Fluoro-4-methoxy-2-pyridyl)-5-methyl-7,8-dihydro-5H-pyrido[4,3-d]pyrimidin-2-yl]thiazole;

6-(6-Fluoro-4-methoxy-2-pyridyl)-5-methyl-2-(1-methylimidazol-2-yl)-7,8-dihydro-5H-pyrido[4,3-d]pyrimidine;

6-(6-Fluoro-4-methoxy-2-pyridyl)-5-methyl-2-(1-methylimidazol-4-yl)-7,8-dihydro-5H-pyrido[4,3-d]pyrimidine;

6-(6-Fluoro-4-methoxy-2-pyridyl)-5-methyl-2-pyrazol-1-yl-7,8-dihydro-5H-pyrido[4,3-d]pyrimidine;

2-(1-Benzylimidazol-4-yl)-6-(6-fluoro-4-methoxy-2-pyridyl)-5-methyl-7,8-dihydro-5H-pyrido[4,3-d]pyrimidine;

2-Fluoro-N,N-dimethyl-6-(5-methyl-2-thiazol-4-yl-7,8-dihydro-5H-pyrido[4,3-d]pyrimidin-6-yl)pyridin-4-amine;

4-[6-Fluoro-4-(5-methyl-2-thiazol-4-yl-7,8-dihydro-5H-pyrido[4,3-d]pyrimidin-6-yl)-2-pyridyl]morpholine;

4-[2-Fluoro-6-(5-methyl-2-thiazol-4-yl-7,8-dihydro-5H-pyrido[4,3-d]pyrimidin-6-yl)-4-pyridyl]morpholine;

4-[4-Fluoro-6-(5-methyl-2-thiazol-4-yl-7,8-dihydro-5H-pyrido[4,3-d]pyrimidin-6-yl)-2-pyridyl]morpholine;

4-[6-(6-Fluoro-4-methoxy-2-pyridyl)-5-methyl-7,8-dihydro-5H-pyrido[4,3-d]pyrimidin-2-yl]-2-methyl-thiazole;

5-[6-(6-Fluoro-4-methoxy-2-pyridyl)-5-methyl-7,8-dihydro-5H-pyrido[4,3-d]pyrimidin-2-yl]-2-methyl-thiazole;

4-[6-(2-Fluoro-6-pyrrolidin-1-yl-4-pyridyl)-5-methyl-7,8-dihydro-5H-pyrido[4,3-d]pyrimidin-2-yl]thiazole;

4-[6-(6-Fluoro-4-pyrrolidin-1-yl-2-pyridyl)-5-methyl-7,8-dihydro-5H-pyrido[4,3-d]pyrimidin-2-yl]thiazole;

4-[6-(4-Fluoro-6-pyrrolidin-1-yl-2-pyridyl)-5-methyl-7,8-dihydro-5H-pyrido[4,3-d]pyrimidin-2-yl]thiazole;

4-[6-[2-Fluoro-6-(4-methylsulfonylpiperazin-1-yl)-4-pyridyl]-5-methyl-7,8-dihydro-5H-pyrido[4,3-d]pyrimidin-2-yl]thiazole;

4-[6-[6-Fluoro-4-(4-methylsulfonylpiperazin-1-yl)-2-pyridyl]-5-methyl-7,8-dihydro-5H-pyrido[4,3-d]pyrimidin-2-yl]thiazole;

4-[6-[4-Fluoro-6-(4-methylsulfonylpiperazin-1-yl)-2-pyridyl]-5-methyl-7,8-dihydro-5H-pyrido[4,3-d]pyrimidin-2-yl]thiazole;

4-[6-[2-Fluoro-6-(3-methoxypyrrolidin-1-yl)-4-pyridyl]-5-methyl-7,8-dihydro-5H-pyrido[4,3-d]pyrimidin-2-yl]thiazole;

4-[6-[6-Fluoro-4-(3-methoxypyrrolidin-1-yl)-2-pyridyl]-5-methyl-7,8-dihydro-5H-pyrido[4,3-d]pyrimidin-2-yl]thiazole;

4-[6-[4-Fluoro-6-(3-methoxypyrrolidin-1-yl)-2-pyridyl]-5-methyl-7,8-dihydro-5H-pyrido[4,3-d]pyrimidin-2-yl]thiazole;

6-(6-Fluoro-4-methoxy-2-pyridyl)-2-(1H-imidazol-2-yl)-5-methyl-7,8-dihydro-5H-pyrido[4,3-d]pyrimidine;

6-(6-Fluoro-4-methoxy-2-pyridyl)-5-methyl-2-(1H-pyrazol-3-yl)-7,8-dihydro-5H-pyrido[4,3-d]pyrimidine;

4-[6-Fluoro-4-(5-methyl-2-thiazol-4-yl-7,8-dihydro-5H-pyrido[4,3-d]pyrimidin-6-yl)-2-pyridyl]piperazin-2-one;

4-[2-Fluoro-6-(5-methyl-2-thiazol-4-yl-7,8-dihydro-5H-pyrido[4,3-d]pyrimidin-6-yl)-4-pyridyl]piperazin-2-one;

4-[4-Fluoro-6-(5-methyl-2-thiazol-4-yl-7,8-dihydro-5H-pyrido[4,3-d]pyrimidin-6-yl)-2-pyridyl]piperazin-2-one;

4-[6-[2-(Cyclopropylmethoxy)-6-fluoro-4-pyridyl]-5-methyl-7,8-dihydro-5H-pyrido[4,3-d]pyrimidin-2-yl]thiazole;

4-[6-[4-(Cyclopropylmethoxy)-6-fluoro-2-pyridyl]-5-methyl-7,8-dihydro-5H-pyrido[4,3-d]pyrimidin-2-yl]thiazole;

4-[6-[6-(Cyclopropylmethoxy)-4-fluoro-2-pyridyl]-5-methyl-7,8-dihydro-5H-pyrido[4,3-d]pyrimidin-2-yl]thiazole;

4-[6-[2-(2,2-Difluoroethoxy)-6-fluoro-4-pyridyl]-5-methyl-7,8-dihydro-5H-pyrido[4,3-d]pyrimidin-2-yl]thiazole;

4-[6-[4-(2,2-Difluoroethoxy)-6-fluoro-2-pyridyl]-5-methyl-7,8-dihydro-5H-pyrido[4,3-d]pyrimidin-2-yl]thiazole;

4-[6-[6-(2,2-Difluoroethoxy)-4-fluoro-2-pyridyl]-5-methyl-7,8-dihydro-5H-pyrido[4,3-d]pyrimidin-2-yl]thiazole;

4-[6-[2-Fluoro-6-(tetrahydrofuran-3-ylmethoxy)-4-pyridyl]-5-methyl-7,8-dihydro-5H-pyrido[4,3-d]pyrimidin-2-yl]thiazole;

4-[6-[6-Fluoro-4-(tetrahydrofuran-3-ylmethoxy)-2-pyridyl]-5-methyl-7,8-dihydro-5H-pyrido[4,3-d]pyrimidin-2-yl]thiazole;

4-[6-[4-Fluoro-6-(tetrahydrofuran-3-ylmethoxy)-2-pyridyl]-5-methyl-7,8-dihydro-5H-pyrido[4,3-d]pyrimidin-2-yl]thiazole;

1-[3-[[6-Fluoro-4-(5-methyl-2-thiazol-4-yl-7,8-dihydro-5H-pyrido[4,3-d]pyrimidin-6-yl)-2-pyridyl]oxy]propyl]pyrrolidin-2-one;

1-[3-[[2-Fluoro-6-(5-methyl-2-thiazol-4-yl-7,8-dihydro-5H-pyrido[4,3-d]pyrimidin-6-yl)-4-pyridyl]oxy]propyl]pyrrolidin-2-one;

4-[6-(6-Fluoro-4-methoxy-2-pyridyl)-5-methyl-7,8-dihydro-5H-pyrido[4,3-d]pyrimidin-2-yl]-5-methyl-thiazole; and 6-(6-Fluoro-4-methoxy-2-pyridyl)-5-methyl-2-(1H-1,2,4-triazol-5-yl)-7,8-dihydro-5H-pyrido[4,3-d]pyrimidine;

or pharmaceutically acceptable salts, or enantiomers, or diastereomers thereof.

More particularly, the invention relates to the following compounds of formula I:

4-[6-(6-Fluoro-4-methoxy-2-pyridyl)-5-methyl-7,8-dihydro-5H-pyrido[4,3-d]pyrimidin-2-yl]thiazole;

6-(6-Fluoro-4-methoxy-2-pyridyl)-5-methyl-2-(1-methylimidazol-4-yl)-7,8-dihydro-5H-pyrido[4,3-d]pyrimidine;

2-Fluoro-N,N-dimethyl-6-(5-methyl-2-thiazol-4-yl-7,8-dihydro-5H-pyrido[4,3-d]pyrimidin-6-yl)pyridin-4-amine;

4-[6-(6-Fluoro-4-pyrrolidin-1-yl-2-pyridyl)-5-methyl-7,8-dihydro-5H-pyrido[4,3-d]pyrimidin-2-yl]thiazole;

4-[6-[2-Fluoro-6-(4-methylsulfonylpiperazin-1-yl)-4-pyridyl]-5-methyl-7,8-dihydro-5H-pyrido[4,3-d]pyrimidin-2-yl]thiazole;

4-[6-[2-Fluoro-6-(3-methoxypyrrolidin-1-yl)-4-pyridyl]-5-methyl-7,8-dihydro-5H-pyrido[4,3-d]pyrimidin-2-yl]thiazole;

4-[6-[4-Fluoro-6-(3-methoxypyrrolidin-1-yl)-2-pyridyl]-5-methyl-7,8-dihydro-5H-pyrido[4,3-d]pyrimidin-2-yl]thiazole;

4-[2-Fluoro-6-(5-methyl-2-thiazol-4-yl-7,8-dihydro-5H-pyrido[4,3-d]pyrimidin-6-yl)-4-pyridyl]piperazin-2-one;

4-[6-[4-(Cyclopropylmethoxy)-6-fluoro-2-pyridyl]-5-methyl-7,8-dihydro-5H-pyrido[4,3-d]pyrimidin-2-yl]thiazole;

4-[6-[2-Fluoro-6-(tetrahydrofuran-3-ylmethoxy)-4-pyridyl]-5-methyl-7,8-dihydro-5H-pyrido[4,3-d]pyrimidin-2-yl]thiazole;

4-[6-[6-Fluoro-4-(tetrahydrofuran-3-ylmethoxy)-2-pyridyl]-5-methyl-7,8-dihydro-5H-pyrido[4,3-d]pyrimidin-2-yl]thiazole; and 6-(6-Fluoro-4-methoxy-2-pyridyl)-5-methyl-2-(1H-1,2,4-triazol-5-yl)-7,8-dihydro-5H-pyrido[4,3-d]pyrimidine;

or pharmaceutically acceptable salts, or enantiomers, or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$ and $R^3$ are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia (Scheme 1)

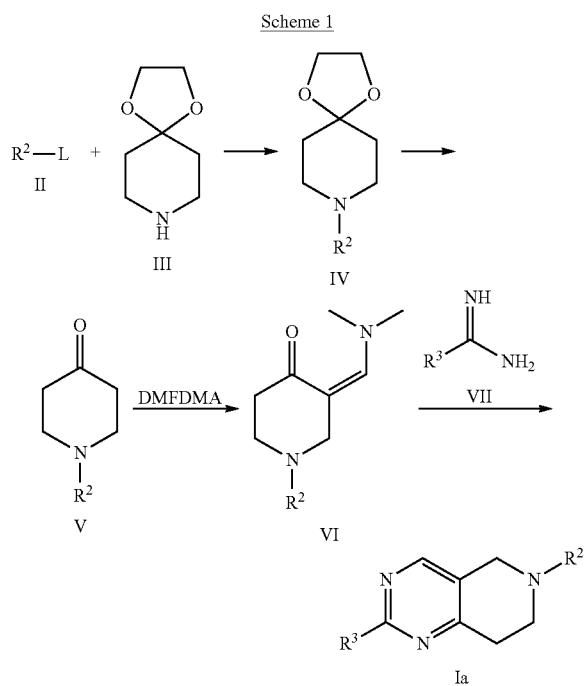

L is F, Cl, Br or I

The compound of formula Ia can be prepared according to Scheme 1.

Compound II is heated with compound III in the presence of a catalyst such as $Pd_2(dba)_3$ or $Pd(OAc)_2$, a ligand such as Ruphos, Sphos or BINAP, and a base such as $Cs_2CO_3$ or t-BuONa, in a suitable solvent such as 1,4-dioxane or toluene, to afford compound IV. Deprotection of compound IV under an acidic condition affords compound V. Reaction of compound V with DMFDMA in the absence or presence of a suitable solvent such as DMF or acetonitrile generates intermediate VI. Compound Ia can be obtained by cyclization of intermediate VI with compound VII in the presence of a base such as $K_2CO_3$, NaOMe or $Et_3N$, in a suitable solvent such as EtOH or MeOH.

General Synthetic Route for Compound Ic (Scheme 2)

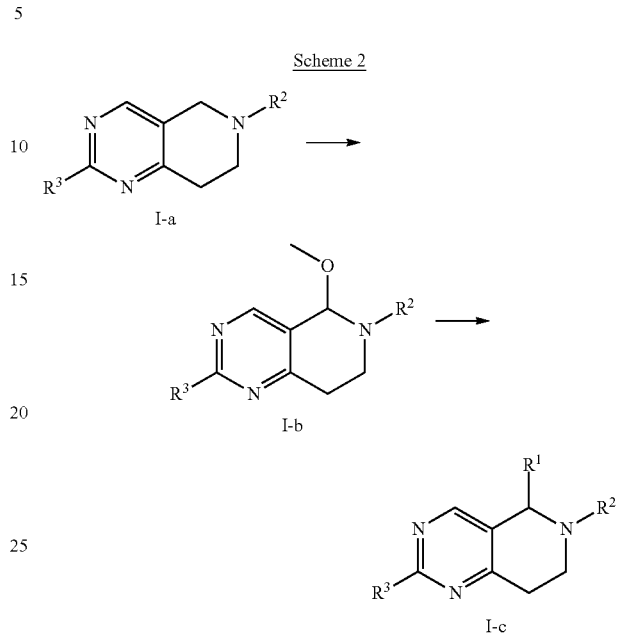

The compound of formula Ic can be prepared according to scheme 2.

Oxidation of compound Ia in the presence of MeOH produces intermediate Ib, the suitable oxidant is selected from $RuCl_3$ and $NaIO_4$. Compound Ic can be produced by reaction of intermediate Ib with a nucleophile such as Grignard reagent or dialkylzinc reagent, in the presence of a Lewis acid such as $BF_3·Et_2O$.

This invention also relates to a process for the preparation of a compound of formula I comprising one of the following steps:

(a) Cyclization a Compound of Formula (A)

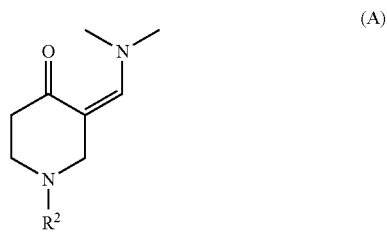

with a compound of formula (B)

in the presence of a base;

(b) Coupling of a Compound of Formula (C)

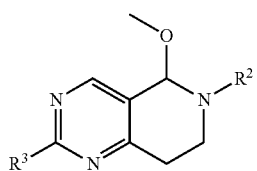

with a nucleophile reagent in the presence of a Lewis acid; wherein $R^1$, $R^2$ and $R^3$ are defined as above.

In step (a), the base can be for example $K_2CO_3$, NaOMe or $Et_3N$.

In step (b), the nucleophile reagent can be for example Grignard reagent or dialkylzinc reagent; the Lewis acid can be for example $BF_3.Et_2O$.

A compound of formula I when manufactured according to the above process is also an object of the invention.

The compound of this invention also shows good safety and PK profile.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |

-continued

|  | Per tablet |
|---|---|
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.
Abbreviations used herein are as follows:
μL: microliter
μm: micrometer
μM: micromoles per liter
$IC_{50}$: the half maximal inhibitory concentration
LC/MS: liquid chromatography/mass spectrometry
M: molarity
MHz: megahertz
min: minute
hr(s): hour(s)
mM: millimoles per liter
MS (ESI): mass spectroscopy (electron spray ionization)
nM: nanomoles per liter
NMR: nuclear magnetic resonance
obsd. observed
rt: room temperature
Pd/C: palladium on activated carbon
Pd(dppf)Cl$_2$: [1,1'-bis(diphenylphosphino)ferrocene]dichloropalladium(II)
Pd$_2$(dba)$_3$: tris(dibenzylideneacetone)dipalladium(0)
TFAA: trifluoroacetic anhydride
δ: chemical shift
BINAP: (2,2'-bis(diphenylphosphino)-1,1'-binaphthyl)
Sphos: 2-dicyclohexylphosphino-2',6'-dimethoxybiphenyl
Xphos: 2-dicyclohexylphosphino-2',4',6'-triisopropylbiphenyl
Xphos-Pd-G2: chloro(2-dicyclohexylphosphino-2',4',6'-triisopropyl-1,1'-biphenyl)[2-(2'-amino-1,1'-biphenyl)]palladium(II)
DMFDMA: N,N-dimethylformamide dimethyl acetal
t-BuONa: sodium tert-butoxide
NMP: N-methyl-2-pyrrolidone
MTBE: methyl tert-butyl ether General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

Chiral Separation was conducted on Thar 350 preparative SFC using ChiralPak AD-10u (200×50 mm I.D.) with mobile phase A for CO$_2$ and B for ethanol.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H$_2$O; B: 0.1% formic acid in acetonitrile;
Basic condition: A: 0.05% NH$_3$·H$_2$O in H$_2$O; B: acetonitrile;
Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty or CEM Discover.

NMR Spectra were obtained using Bruker Avance 400 MHz.

Optical rotation was measured on an AUTOPOL® V automatic polarimeter.

All reactions involving air-sensitive reagents were performed under an argon atmosphere. Reagents were used as received from commercial suppliers without further purification unless otherwise noted.

PREPARATIVE EXAMPLES

Example 1

6-(3,4-Difluoro-5-methoxy-phenyl)-2-(1-methylimidazol-2-yl)-7,8-dihydro-5H-pyrido[4,3-d]pyrimidine

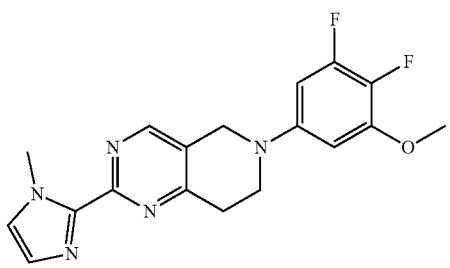 [SMILES: COc1cc(N2CCc3nc(-c4nccn4C)ncc3C2)cc(F)c1F]

Step 1: preparation of 1-methylimidazole-2-carbaldehyde oxime

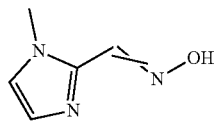

To a solution of 1-methyl-1H-imidazole-2-carbaldehyde (5.0 g, 46 mmol) in MeOH (50 mL) was added $K_2CO_3$ (6.9 g, 50 mmol) and $NH_2OH$ hydrochloride (3.55 g, 50 mmol) at 0° C. The resulting mixture was then warmed to rt and stirred for 12 hrs. The solid was filtered off and the filtrate was concentrated in vacuo. The residue was slurried in MTBE (50 mL) and the precipitate was collected by suction to afford 1-methylimidazole-2-carbaldehyde oxime (7.0 g, crude) as a white solid.

Step 2: preparation of 1-methylimidazole-2-carbonitrile

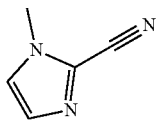

To a solution of 1-methylimidazole-2-carbaldehyde oxime (7.0 g, 60 mmol) in DCM (50 mL) was added TFAA (50 g, 242 mmol) slowly at 0° C. The mixture was stirred at rt for 12 hrs and then concentrated in vacuo. The residue was diluted with DCM (200 mL) and then washed with saturated aqueous $NaHCO_3$ (50 mL) and brine (50 mL). The organic phase was dried over anhydrous $Na_2SO_4$ and concentrated in vacuo to afford 1-methylimidazole-2-carbonitrile (5.0 g, crude) as a brown oil, which was used in the next step without any further purification.

Step 3: preparation of 1-methylimidazole-2-carboxamidine hydrochloride

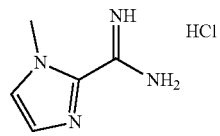

To a solution of 1-methylimidazole-2-carbonitrile (5.0 g, 47 mmol) in MeOH (50 mL) was added $CH_3ONa$ (1.3 g, 24 mmol). The resulting mixture was stirred at rt for 12 hrs. To the resulting solution was added $NH_4Cl$ (3.9 g, 73 mmol), and the resulting mixture was stirred at rt for another 3 hours and then filtered. The filtrate was concentrated in vacuo. The solid residue was recrystallized from MTBE (30 mL) to afford 1-methylimidazole-2-carboxamidine hydrochloride (5.0 g) as a white solid.

Step 4: preparation of 8-(3,4-difluoro-5-methoxy-phenyl)-1,4-dioxa-8-azaspiro[4.5]decane

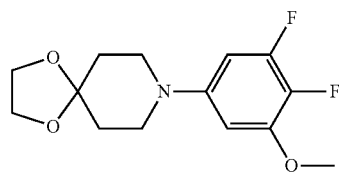 [SMILES: COc1cc(N2CCC3(CC2)OCCO3)cc(F)c1F]

A mixture of 5-bromo-1,2-difluoro-3-methoxy-benzene (1.0 g, 5.6 mmol), 1,4-dioxa-8-azaspiro[4.5]decane hydrochloride (1.4 g, 6.4 mmol), tert-BuONa (800 mg, 8.3 mmol), Ruphos (50 mg), $Pd_2(dba)_3$ (100 mg) in dioxane (10 mL) was heated to 100° C. and stirred for 12 hrs. After being cooled to rt, the mixture was filtered and the filtrate was concentrated in vacuo. The residue was diluted with DCM (100 mL), washed with water (30 mL) and brine (30 mL), then dried over anhydrous $Na_2SO_4$ and concentrated in vacuo to give 8-(3,4-difluoro-5-methoxy-phenyl)-1,4-dioxa-8-azaspiro[4.5]decane (2.4 g, crude) as a brown oil, which was used in the next step without any further purification.

Step 5: preparation of 1-(3,4-difluoro-5-methoxy-phenyl)piperidin-4-one

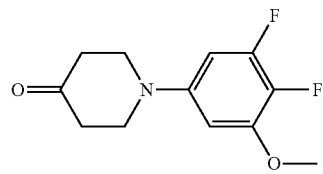 [SMILES: COc1cc(N2CCC(=O)CC2)cc(F)c1F]

A mixture of 8-(3,4-difluoro-5-methoxy-phenyl)-1,4-dioxa-8-azaspiro[4.5]decane (2.4 g, 1.67 mmol), $HCO_2H$ (10 mL) and $H_2O$ (10 mL) was heated at 90° C. with stirring for 2 hrs. After being cooled to rt, the resulting mixture was diluted with DCM (50 mL) and washed with aqueous saturated $NaHCO_3$ solution and brine, then dried over anhydrous $Na_2SO_4$ and concentrated in vacuo to give 1-(3,4- difluoro-5-methoxy-phenyl)piperidin-4-one (1.1 g, crude) as a red oil, which was used directly in the next step without any further purification.

Step 6: preparation of 6-(3,4-difluoro-5-methoxy-phenyl)-2-(1-methylimidazol-2-yl)-7,8-dihydro-5H-pyrido[4,3-d]pyrimidine

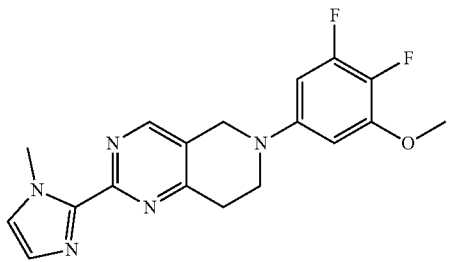 [SMILES: COc1cc(N2CCc3nc(-c4nccn4C)ncc3C2)cc(F)c1F]

A mixture of 1-(3,4-difluoro-5-methoxy-phenyl)piperidin-4-one (1.1 g, 4.6 mmol) and DMFDMA (12 mL) was heated at 120° C. with stirring for 4 hrs. The resulting mixture was concentrated in vacuo and the residue was dissolved in MeOH (10 mL). To the resulting solution was added K$_2$CO$_3$ (1.38 g, 10 mmol) and 1-methylimidazole-2-carboxamidine hydrochloride (540 mg, 3.36 mmol). The resulting mixture was heated at 70° C. with stirring for 12 hrs. The resulting reaction mixture was filtered and the filtrate was concentrated in vacuo. The residue was purified by prep-HPLC to give 6-(3,4-difluoro-5-methoxy-phenyl)-2-(1-methylimidazol-2-yl)-7,8-dihydro-5H-pyrido[4,3-d]pyrimidine (65 mg) a light yellow solid. $^1$H NMR (400 MHz, D$_2$O) δ ppm: 8.73 (s, 1 H), 7.59-7.57 (d, 2 H), 6.61-6.60 (d, 2 H), 4.40 (s, 2 H), 4.26 (s, 3 H), 3.87 (s, 3 H), 3.66 (s, 2 H), 3.17 (s, 2 H). MS obsd. (ESI$^+$) [(M+H)$^+$]: 358.

Example 2

6-(6-Fluoro-4-methoxy-2-pyridyl)-5-methyl-2-(triazol-1-yl)-7,8-dihydro-5H-pyrido[4,3-d]pyrimidine

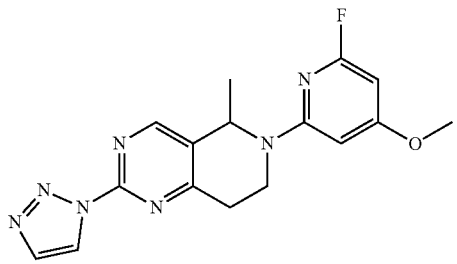 [SMILES: COc1cc(F)nc(N2CCc3nc(-n4ccnn4)ncc3C2C)c1]

Step 1: preparation of 6-benzyl-1,5,7,8-tetrahydro-pyrido[4,3-d]pyrimidine-2,4-dione

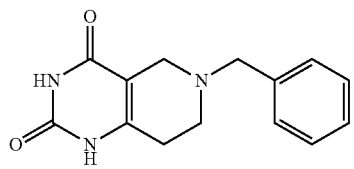 [SMILES: O=c1[nH]c2c(c(=O)[nH]1)CN(Cc1ccccc1)CC2]

A mixture of 1-benzyl-3-carbethoxy-4-piperidone hydrochloride (100.0 g, 0.34 mol, vendor: Acros Organics, CAS registry number: 1454-53-1), NaOMe (181.4 g, 3.36 mol) and urea (100.8 g, 1.68 mol) in EtOH (1.5 L) was heated at 80° C. with stirring for 16 hrs under nitrogen. The resulting mixture was cooled to rt and filtered. The collected solid was suspended in H$_2$O (1.0 L), then basified with aqueous NaOH (3.0 M) solution and filtered. The collected solid was dried in vacuo to give 6-benzyl-1,5,7,8-tetrahydropyrido[4,3-d]pyrimidine-2,4-dione (73.0 g) as a light yellow solid.

Step 2: preparation of 6-benzyl-2,4-dichloro-7,8-dihydro-5H-pyrido[4,3-d]pyrimidine

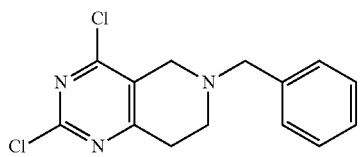 [SMILES: Clc1nc(Cl)c2c(n1)CCN(Cc1ccccc1)C2]

A mixture of 6-benzyl-1,5,7,8-tetrahydropyrido[4,3-d]pyrimidine-2,4-dione (73.0 g, 0.28 mol) and POCl$_3$ (421.54 g, 2.75 mol) was heated at 110° C. with stirring under nitrogen for 3 hrs. The resulting reaction mixture was cooled to rt and concentrated in vacuo. The residue was suspended in H$_2$O (1.0 L), then basified with cold aqueous NaOH (3.0 M) slowly until pH=9-10, and extracted with DCM (500 mL) for three times. The combined organic phase was dried over anhydrous Na$_2$SO$_4$ and concentrated in vacuo to give crude 6-benzyl-2,4-dichloro-7,8-dihydro-5H-pyrido[4,3-d]pyrimidine (54.0 g) as a yellow solid, which was used in the next step directly without any further purification.

Step 3: preparation of 6-benzyl-2-chloro-7,8-dihydro-5H-pyrido[4,3-d]pyrimidine

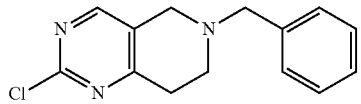 [SMILES: Clc1ncc2c(n1)CCN(Cc1ccccc1)C2]

A mixture of 6-benzyl-2,4-dichloro-7,8-dihydro-5H-pyrido[4,3-d]pyrimidine (58.3 g, 0.19 mol) and Zn powder (94.7 g, 0.99 mol) in EtOH (1.0 L) and NH$_4$OH (146 mL) was heated to 80° C. and stirred under nitrogen for 16 hrs. The reaction mixture was cooled to rt and filtered. The filtrate was concentrated in vacuo and the residue was purified by the flash column (eluting with PE/EA=5/1, v:v) to give 6-benzyl-2-chloro-7,8-dihydro-5H-pyrido[4,3-d]pyrimidine (18.9 g) as a colorless oil.

Step 4: preparation of 6-benzyl-2-(triazol-1-yl)-7,8-dihydro-5H-pyrido[4,3-d]pyrimidine and 6-benzyl-2-(triazol-2-yl)-7,8-dihydro-5H-pyrido[4,3-d]pyrimidine

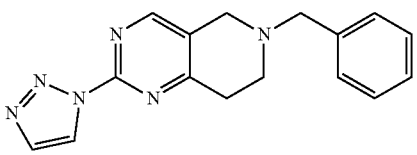

-continued

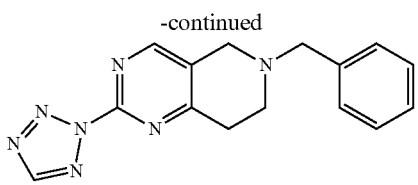

A mixture of 6-benzyl-2-chloro-7,8-dihydro-5H-pyrido[4,3-d]pyrimidine (5.0 g, 19.3 mmol), 1H-1,2,3-triazole (1.6 g, 23.2 mmol) and K$_2$CO$_3$ (4.0 g, 28.9 mmol) in NMP (50 mL) was heated to 80° C. and stirred under nitrogen for 4 hrs. The mixture was cooled to rt and diluted with H$_2$O (100 mL). The resulting mixture was extracted with EA (200 mL) for three times. The combined organic phase was dried over anhydrous Na$_2$SO$_4$, concentrated in vacuo. The residue was purified by the prep-HPLC to afford 6-benzyl-2-(triazol-1-yl)-7,8-dihydro-5H-pyrido[4,3-d]pyrimidine (1.0 g) as a light yellow solid and 6-benzyl-2-(triazol-2-yl)-7,8-dihydro-5H-pyrido[4,3-d]pyrimidine (2.5 g) as yellow solid.

Step 5: preparation of 2-(triazol-1-yl)-5,6,7,8-tetrahydropyrido[4,3-d]pyrimidine

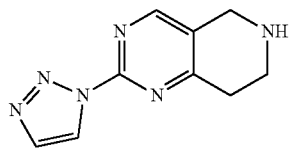 [SMILES: c1cn(-c2ncc3c(n2)CCNC3)nn1]

A mixture of 6-benzyl-2-(triazol-1-yl)-7,8-dihydro-5H-pyrido[4,3-d]pyrimidine (2.5 g, 8.55 mmol) and Pd/C (500 mg) in MeOH (50 mL) was stirred under hydrogen (45 psi) at rt for 24 hrs. The catalyst was then filtered off and the filtrate was concentrated in vacuo. The residue was purified by column chromatography (eluting with DCM/MeOH=20/1, v:v) to give 2-(triazol-1-yl)-5,6,7,8-tetrahydropyrido[4,3-d]pyrimidine (1.26 g) as a yellow solid.

Step 6: Preparation of 2,6-difluoro-4-methoxy-pyridine

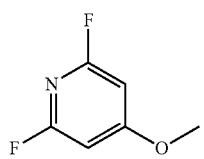

A stirred solution of 2,4,6-trifluoropyridine (10.0 g, 0.075 mol) in MeOH (100 mL) was cooled to 0° C. and to the solution was added NaOMe (6.5 g, 0.12 mol) portion wise. The resulting mixture was heated to 50° C. and stirred under nitrogen for 24 hrs, then cooled to rt and concentrated in vacuo. The residue was purified by column chromatography (eluting with PE/EA=20/1, v:v) to give 2,6-difluoro-4-methoxy-pyridine (5.5 g) as a colorless liquid.

Step 7: preparation of 6-(6-fluoro-4-methoxy-2-pyridyl)-2-(triazol-1-yl)-7,8-dihydro-5H-pyrido[4,3-d]pyrimidine

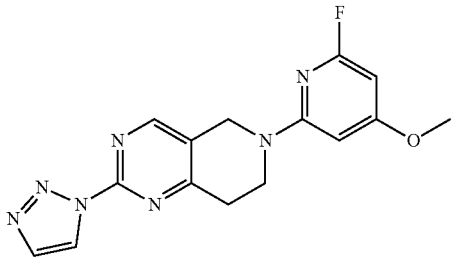

A mixture of 2-(triazol-1-yl)-5,6,7,8-tetrahydropyrido[4,3-d]pyrimidine (500 mg, 2.47 mmol), 2,6-difluoro-4-methoxy-pyridine (540 mg, 3.71 mmol) and K$_2$CO$_3$ (1.0 g, 7.42 mmol) in NMP (10 mL) was stirred at 140° C. under nitrogen for 2 hrs. The resulting reaction mixture was cooled to rt, diluted with H$_2$O (20 mL) and extracted with EA (30 mL) for three times. The combined organic phase was washed with brine, dried over anhydrous Na$_2$SO$_4$ and concentrated in vacuo. The residue was purified by column chromatography (eluting with DCM/MeOH=5/1, v:v) to give 6-(6-fluoro-4-methoxy-2-pyridyl)-2-(triazol-1-yl)-7,8-dihydro-5H-pyrido[4,3-d]pyrimidine (250 mg) as light yellow solid.

Step 8: preparation of 6-(6-fluoro-4-methoxy-2-pyridyl)-5-methoxy-2-(triazol-1-yl)-7,8-dihydro-5H-pyrido[4,3-d]pyrimidine

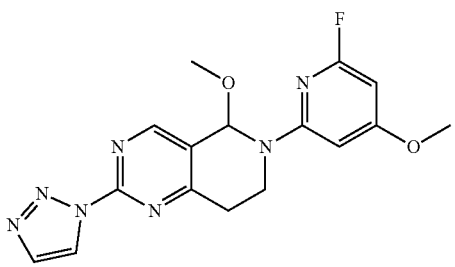 [SMILES: COc1cc(F)nc(N2CCc3nc(-n4ccnn4)ncc3C2OC)c1]

To a stirred solution of 6-(6-fluoro-4-methoxy-2-pyridyl)-2-(triazol-1-yl)-7,8-dihydro-5H-pyrido[4,3-d]pyrimidine (150 mg, 0.46 mmol) in THF/MeOH (2 mL/2 mL) was added RuCl$_3$ hydrate (10 mg, 0.04 mmol) at −70° C. The resulting mixture was stirred for 10 min and then to the resulting reaction mixture was added a solution of NaIO$_4$ (294 mg, 1.38 mmol) in H$_2$O (2 mL) drop wise at −70° C. The resulting mixture was warmed to rt and stirred for 8 hrs, then diluted with aqueous saturated Na$_2$SO$_3$ solution and extracted with DCM (20 mL) for three times. The combined organic phase was dried over anhydrous Na$_2$SO$_4$ and concentrated in vacuo to give 6-(6-fluoro-4-methoxy-2-pyridyl)-5-methoxy-2-(triazol-1-yl)-7,8-dihydro-5H-pyrido[4,3-d]pyrimidine (90 mg, crude) which was used directly in the next step.

Step 9: preparation of 6-(6-fluoro-4-methoxy-2-pyridyl)-5-methyl-2-(triazol-1-yl)-7,8-dihydro-5H-pyrido[4,3-d]pyrimidine

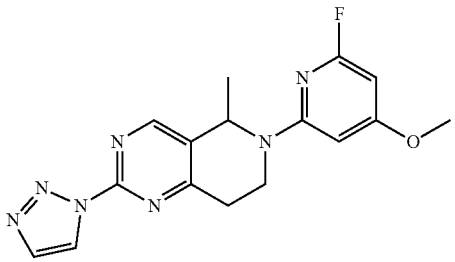 [SMILES: COc1cc(F)nc(N2CCc3nc(-n4ccnn4)ncc3C2C)c1]

To a stirred solution of 6-(6-fluoro-4-methoxy-2-pyridyl)-5-methoxy-2-(triazol-1-yl)-7,8-dihydro-5H-pyrido[4,3-d]pyrimidine (90 mg, 0.08 mmol) in THF (2 mL) was added $BF_3.Et_2O$ (107 mg, 0.75 mmol). The resulting mixture was stirred for 10 mins at −60° C. and then to the resulting reaction mixture was added a solution of $CH_3MgBr$ (0.25 mL, 0.75 mmol) in $Et_2O$ slowly at −60° C. The resulting mixture was warmed to −20° C. and stirred for 1 hr, then diluted with aqueous saturated $NH_4Cl$ (10 mL) solution and extracted with EA (10 mL) for three times. The combined organic phase was dried over anhydrous $Na_2SO_4$ and concentrated in vacuo. The residue was purified by prep-HPLC to give 6-(6-fluoro-4-methoxy-2-pyridyl)-5-methyl-2-(triazol-1-yl)-7,8-dihydro-5H-pyrido[4,3-d]pyrimidine (7 mg) as a white solid. $^1$H NMR (400 MHz, Methanol-$d_4$) δ ppm: 8.83 (d, 2 H), 7.94 (s, 1 H), 6.24 (s, 1 H), 5.89 (s, 1 H), 5.72 (q, 1 H), 4.52 (dd, 1 H), 3.87 (s, 3 H), 3.50 (ddd, 1 H), 3.04-3.23 (m, 2 H), 1.58 (d, 3 H). MS obsd. (ESI$^+$) [(M+H)$^+$]: 342.

Example 3

6-(6-Fluoro-4-methoxy-2-pyridyl)-5-methyl-2-(triazol-2-yl)-7,8-dihydro-5H-pyrido[4,3-d]pyrimidine

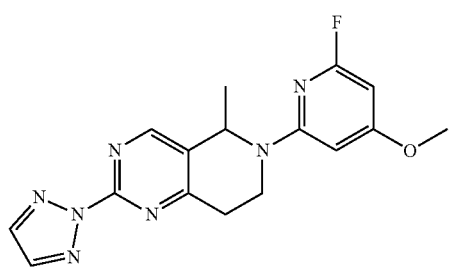 [SMILES: COc1cc(F)nc(N2CCc3nc(-n4nccn4)ncc3C2C)c1]

Step 1: preparation of 2-(triazol-2-yl)-5,6,7,8-tetrahydropyrido[4,3-d]pyrimidine

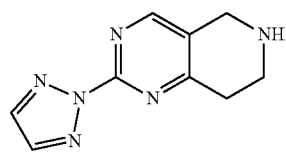 [SMILES: c1cnn(-c2ncc3c(n2)CCNC3)n1]

A mixture of 6-benzyl-2-(triazol-2-yl)-7,8-dihydro-5H-pyrido[4,3-d]pyrimidine (1.1 g, 8.55 mmol, one of the products of step 4 in Example 2) and Pd/C (200 mg, 10 wt. %) in MeOH (20 mL) was stirred under hydrogen (45 psi) at rt for 24 hrs. The catalyst was filtered off and the filtrate was concentrated in vacuo. The residue was purified by column chromatography (eluting with DCM/MeOH=20/1, v:v) to give 2-(triazol-2-yl)-5,6,7,8-tetrahydropyrido[4,3-d]pyrimidine (364 mg) as a yellow solid.

Step 2: preparation of 6-(6-fluoro-4-methoxy-2-pyridyl)-2-(triazol-2-yl)-7,8-dihydro-5H-pyrido[4,3-d]pyrimidine

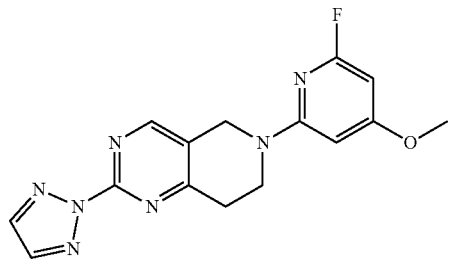 [SMILES: COc1cc(F)nc(N2CCc3nc(-n4nccn4)ncc3C2)c1]

A mixture of 2-(triazol-2-yl)-5,6,7,8-tetrahydropyrido[4,3-d]pyrimidine (364 mg, 1.8 mmol), 2,6-difluoro-4-methoxy-pyridine (784 mg, 5.4 mmol) and $K_2CO_3$ (746 mg, 5.4 mmol) in NMP (5 mL) was stirred at 140° C. under nitrogen for 2 hrs. After being cooled to rt, the reaction mixture was diluted with $H_2O$ (20 mL) and extracted with EA (30 mL) for three times. The combined organic phase was washed with brine, dried over anhydrous $Na_2SO_4$ and concentrated in vacuo. The residue was purified by column chromatography (eluting with DCM/MeOH=50/1, v:v) to give 6-(6-fluoro-4-methoxy-2-pyridyl)-2-(triazol-2-yl)-7,8-dihydro-5H-pyrido[4,3-d]pyrimidine (323 mg) as a yellow solid.

Step 3: preparation of 6-(6-fluoro-4-methoxy-2-pyridyl)-5-methoxy-2-(triazol-2-yl)-7,8-dihydro-5H-pyrido[4,3-d]pyrimidine

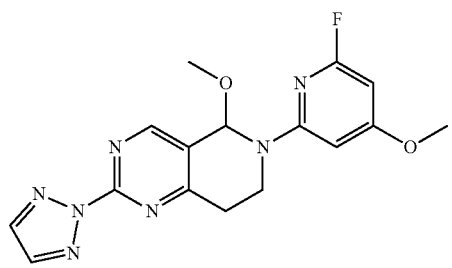 [SMILES: COc1cc(F)nc(N2CCc3nc(-n4nccn4)ncc3C2OC)c1]

To a stirred solution of 6-(6-fluoro-4-methoxy-2-pyridyl)-2-(triazol-2-yl)-7,8-dihydro-5H-pyrido[4,3-d]pyrimidine (323 mg, 0.99 mmol) in THF/MeOH/DCM (4 mL/4 mL/2 mL) was added $RuCl_3$ hydrate (22 mg, 0.10 mmol) at −70° C. The mixture was stirred for 10 mins at −70° C. followed by the addition of a solution of $NaIO_4$ (634 mg, 2.96 mmol) in $H_2O$ (6 mL) drop wise at −70° C. The reaction mixture was warmed to rt and stirred for 20 hrs, diluted with aqueous saturated $Na_2SO_3$ solution and extracted with DCM (20 mL)

for three times. The combined organic phase was dried over anhydrous Na₂SO₄ and concentrated in vacuo to give crude 6-(6-fluoro-4-methoxy-2-pyridyl)-5-methoxy-2-(triazol-2-yl)-7,8-dihydro-5H-pyrido[4,3-d]pyrimidine (120 mg) which was used directly in the next step.

Step 4: preparation of 6-(6-fluoro-4-methoxy-2-pyridyl)-5-methyl-2-(triazol-2-yl)-7,8-dihydro-5H-pyrido[4,3-d]pyrimidine

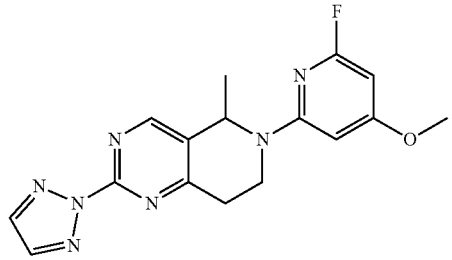

To a stirred solution of 6-(6-fluoro-4-methoxy-2-pyridyl)-5-methoxy-2-(triazol-2-yl)-7,8-dihydro-5H-pyrido[4,3-d]pyrimidine (120 mg, 0.34 mmol) in THF (2 mL) was added BF₃.Et₂O (143 mg, 1.00 mmol) at −70° C. The resulting mixture was stirred at −70° C. and then to the reaction mixture was added a solution of CH₃MgBr (0.34 mL, 1.00 mmol) in Et₂O slowly at −70° C. The reaction mixture was warmed to −20° C. and stirred for 1 hr, then diluted with aqueous saturated NH₄Cl solution and extracted with EA (10 mL) for three times. The combined organic phase was dried over anhydrous Na₂SO₄ and concentrated in vacuo. The residue was purified by the prep-HPLC to give 6-(6-fluoro-4-methoxy-2-pyridyl)-5-methyl-2-(triazol-2-yl)-7,8-dihydro-5H-pyrido[4,3-d]pyrimidine (9 mg) as a white solid. ¹H NMR (400 MHz, Methanol-d₄) δ ppm: 8.79 (s, 1 H), 8.11 (s, 2 H), 6.24 (s, 1 H), 5.88 (d, 1 H), 5.71 (q, 1 H), 4.51 (dd, 1 H), 3.86 (s, 3 H), 3.43-3.54 (m, 1 H), 3.04-3.22 (m, 2 H), 1.57 (d, 3 H). MS obsd. (ESI⁺) [(M+H)⁺]: 342.

Example 4

2-[6-(6-Fluoro-4-methoxy-2-pyridyl)-5-methyl-7,8-dihydro-5H-pyrido[4,3-d]pyrimidin-2-yl]oxazole

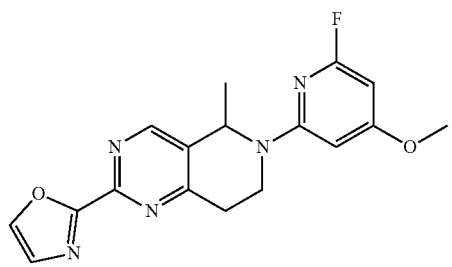 [SMILES: COc1cc(F)nc(N2CCc3nc(-c4ncco4)ncc3C2C)c1]

Step 1: preparation of tert-butyl 2-methoxy-7,8-dihydro-5H-pyrido[4,3-d]pyrimidine-6-carboxylate

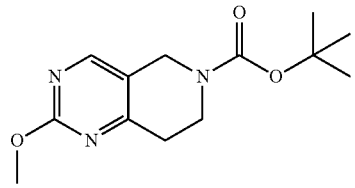 [SMILES: COc1ncc2c(n1)CCN(C(=O)OC(C)(C)C)C2]

A mixture of 1-boc-4-piperidone (200.0 g, 1.00 mol) and DMFDMA (598.0 g, 5.02 mol) was heated at 120° C. and stirred under nitrogen for 12 hrs. The mixture was concentrated in vacuo and the residue was dissolved in MeOH (6.0 L). To the resulting solution was added O-methylisourea sulfate (319.4 g, 1.86 mol) and K₂CO₃ (699.4 g, 5.06 mol). The resulting reaction mixture was heated at 70° C. and stirred under nitrogen for 6 hrs. After being cooled to rt, the resulting mixture was filtered and the filtrate was concentrated in vacuo. The residue was purified by flash column (eluting with DCM/MeOH=50/1, v:v) to afford tert-butyl 2-methoxy-7,8-dihydro-5H-pyrido[4,3-d]pyrimidine-6-carboxylate (117.0 g) as a yellow oil.

Step 2: preparation of 2-methoxy-5,6,7,8-tetrahydropyrido[4,3-d]pyrimidine

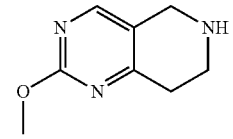

To a stirred solution of tert-butyl 2-methoxy-7,8-dihydro-5H-pyrido[4,3-d]pyrimidine-6-carboxylate (58.5 g, 0.22 mol) in 1,4-dioxane (450 mL) was added a solution of HCl in 1,4-dioxane (220 mL, 4.0 M) slowly at rt. The resulting mixture was stirred for 12 hrs and then concentrated in vacuo. The residue was dissolved in MeOH (150 mL), basified with basic resin and filtered. The filtrate was concentrated in vacuo to give crude 2-methoxy-5,6,7,8-tetrahydropyrido[4,3-d]pyrimidine (36.0 g) which was used directly in the next step without any further purification.

Step 3: preparation of 6-(6-fluoro-4-methoxy-2-pyridyl)-2-methoxy-7,8-dihydro-5H-pyrido[4,3-d]pyrimidine

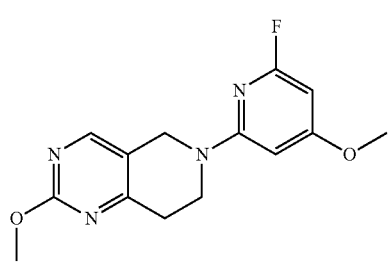 [SMILES: COc1cc(F)nc(N2CCc3nc(OC)ncc3C2)c1]

A mixture of 2-methoxy-5,6,7,8-tetrahydropyrido[4,3-d] pyrimidine (36.5 g, 0.22 mol), 2,6-difluoro-4-methoxy-pyridine (41.7 g, 0.29 mol) and K$_2$CO$_3$ (61.0 g, 0.44 mol) in NMP (400 mL) was heated at 140° C. under nitrogen and stirred for 2 hrs. After being cooled to rt, the reaction mixture was diluted with H$_2$O (800 mL) and extracted with EA (400 mL) for three times. The combined organic phase was washed with brine (200 mL), dried over anhydrous Na$_2$SO$_4$ and concentrated in vacuo. The residue was purified by column chromatography (eluting with PE/EA=1/1, v:v) to give 6-(6-fluoro-4-methoxy-2-pyridyl)-2-methoxy-7,8-dihydro-5H-pyrido[4,3-d]pyrimidine (60.0 g) as a yellow solid.

Step 4: preparation of 6-(6-fluoro-4-methoxy-2-pyridyl)-2,5-dimethoxy-7,8-dihydro-5H-pyrido[4,3-d]pyrimidine

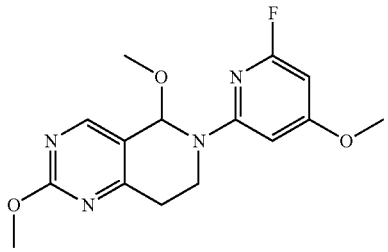 [SMILES: COc1cc(F)nc(N2CCc3nc(OC)ncc3C2OC)c1]

To a stirred solution of 6-(6-fluoro-4-methoxy-2-pyridyl)-2-methoxy-7,8-dihydro-5H-pyrido[4,3-d]pyrimidine (10.0 g, 0.034 mol) in THF/MeOH/DCM (80 mL/80 mL/40 mL) was added RuCl$_3$ hydrate (1.54 g, 0.006 mol) and H$_2$O$_2$ (39 g, 0.344 mol) at −70° C. slowly. The resulting mixture was warmed to rt and stirred for 48 hrs, then diluted with aqueous saturated Na$_2$SO$_3$ solution and filtered. The filtrate was extracted with DCM (500 mL) for three times. The combined organic phase was dried over anhydrous Na$_2$SO$_4$ and concentrated in vacuo to give crude 6-(6-fluoro-4-methoxy-2-pyridyl)-2,5-dimethoxy-7,8-dihydro-5H-pyrido[4,3-d]pyrimidine (14.5 g) which was used directly in the next step without any further purification.

Step 5: preparation of 6-(6-fluoro-4-methoxy-2-pyridyl)-2-methoxy-5-methyl-7,8-dihydro-5H-pyrido[4,3-d]pyrimidine

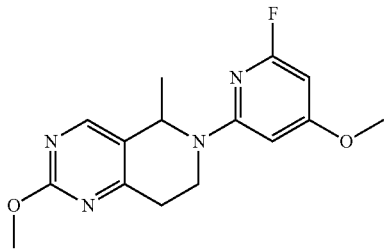 [SMILES: COc1cc(F)nc(N2CCc3nc(OC)ncc3C2C)c1]

To a stirred solution of 6-(6-fluoro-4-methoxy-2-pyridyl)-2,5-dimethoxy-7,8-dihydro-5H-pyrido[4,3-d]pyrimidine (50.5 g, 0.16 mol) in THF (1.0 L), which was cooled to −70° C., was added BF$_3$.Et$_2$O (67.1 g, 0.47 mol). The resulting mixture was stirred at −70° C. for 10 min and then to the reaction mixture was added a solution of CH$_3$MgBr (158 mL, 0.47 mol) in Et$_2$O slowly at −70° C. After being stirred at −20° C. for 1 hr, the resulting mixture was diluted with aqueous saturated NH$_4$Cl (100 mL) and extracted with EA (500 mL) for three times. The combined organic phase was dried over anhydrous Na$_2$SO$_4$ and concentrated in vacuo. The residue was purified column chromatography (eluting with PE/EA=2/1, v:v) to give 6-(6-fluoro-4-methoxy-2-pyridyl)-2-methoxy-5-methyl-7,8-dihydro-5H-pyrido[4,3-d]pyrimidine (15.1 g) as yellow solid.

Step 6: preparation of 6-(6-fluoro-4-methoxy-2-pyridyl)-5-methyl-7,8-dihydro-5H-pyrido[4,3-d]pyrimidin-2-ol

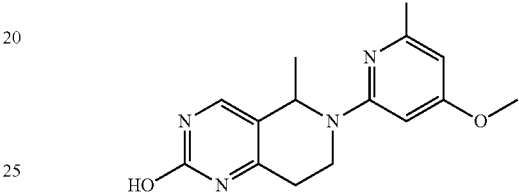

To a stirred solution of 6-(6-fluoro-4-methoxy-2-pyridyl)-2-methoxy-5-methyl-7,8-dihydro-5H-pyrido[4,3-d]pyrimidine (10.6 g, 0.035 mol) in CH$_3$CN (300 mL) was added NaI (15.6 g, 0.104 mol) and TMSCl (11.3 g, 0.104 mol) slowly at rt. The resulting mixture was stirred at 40° C. for 12 hrs and concentrated in vacuo. The residue was dissolved in DCM/MeOH (500 mL, 10:1, v:v) and washed with aqueous saturated Na$_2$SO$_3$ solution (40 mL), aqueous saturated NaHCO$_3$ solution (50 mL) and brine (50 mL) successively. The organic phase was dried over anhydrous Na$_2$SO$_4$ and concentrated in vacuo to give crude 6-(6-fluoro-4-methoxy-2-pyridyl)-5-methyl-7,8-dihydro-5H-pyrido[4,3-d]pyrimidin-2-ol (9.2 g) which was used directly in the next step without any further purification.

Step 7: preparation of 2-chloro-6-(6-fluoro-4-methoxy-2-pyridyl)-5-methyl-7,8-dihydro-5H-pyrido[4,3-d]pyrimidine

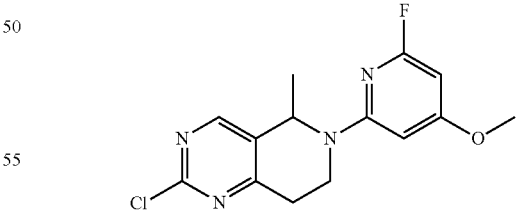

A mixture of 6-(6-fluoro-4-methoxy-2-pyridyl)-5-methyl-7,8-dihydro-5H-pyrido[4,3-d]pyrimidin-2-ol (9.2 g, 0.03 mol) and POCl$_3$ (115.83 g) was stirred at 90° C. under nitrogen for 10 hrs. After being cooled to rt, the reaction mixture was poured into a stirred mixture of NH$_4$OH (500 mL) and DCM (1.0 L) at 0° C. slowly. The organic phase was separated, washed with brine (200 mL), dried over anhydrous Na$_2$SO$_4$ and concentrated in vacuo. The residue was purified by column chromatography (eluting with PE/EA=5/1, v:v) to give 2-chloro-6-(6-fluoro-4-methoxy-2-pyridyl)-5-methyl-7,8-dihydro-5H-pyrido[4,3-d]pyrimidine (4.4 g) as an yellow solid.

Step 8: preparation of 2-[6-(6-fluoro-4-methoxy-2-pyridyl)-5-methyl-7,8-dihydro-5H-pyrido[4,3-d]pyrimidin-2-yl]oxazole

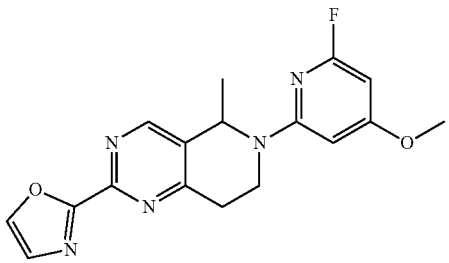 [SMILES: COc1cc(F)nc(N2CCc3nc(-c4ncco4)ncc3C2C)c1]

A flask containing a mixture of 2-chloro-6-(6-fluoro-4-methoxy-2-pyridyl)-5-methyl-7,8-dihydro-5H-pyrido[4,3-d]pyrimidine (100 mg, 0.32 mmol), 2-(tributylstannyl)oxazole (348 mg, 0.97 mmol) and Pd(PPh$_3$)$_2$Cl$_2$ (23 mg, 0.03 mmol) in 1,4-dioxane (4 mL) was degassed and charged with N$_2$. The resulting mixture was heated at 110° C. and stirred under nitrogen for 12 hrs. After being cooled to rt, the reaction mixture was concentrated in vacuo and the residue was purified by prep-HPLC to afford 2-[6-(6-fluoro-4-methoxy-2-pyridyl)-5-methyl-7,8-dihydro-5H-pyrido[4,3-d]pyrimidin-2-yl]oxazole (19 mg) as a white solid. $^1$H NMR (400 MHz, Methanol-d$_4$) δ ppm: 8.80 (s, 1 H), 8.16 (s, 1 H), 7.46 (s, 1 H), 6.23 (s, 1 H), 5.87 (d, 1 H), 5.69 (q, 1 H), 4.50 (dd, 1 H), 3.86 (s, 3 H), 3.42-3.56 (m, 1 H), 3.01-3.21 (m, 2 H), 1.56 (d, 3 H). MS obsd. (ESI$^+$) [(M+H)$^+$]: 342.

Example 5

4-[6-(6-Fluoro-4-methoxy-2-pyridyl)-5-methyl-7,8-dihydro-5H-pyrido[4,3-d]pyrimidin-2-yl]thiazole

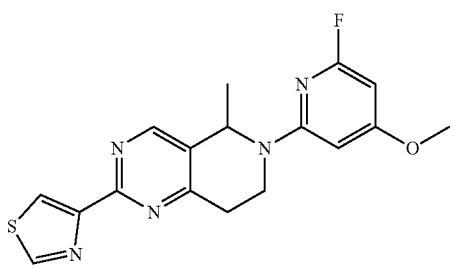 [SMILES: COc1cc(F)nc(N2CCc3nc(-c4cscn4)ncc3C2C)c1]

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), 4-(tributylstannyl) thiazole (242 mg, 0.65 mmol) and Pd(PPh$_3$)$_2$Cl$_2$ (23 mg, 0.03 mmol) in 1,4-dioxane (5 mL) was degassed and charged with N$_2$. The resulting mixture was heated at 120° C. and stirred under nitrogen for 12 hrs. After being cooled to rt, the reaction mixture was concentrated in vacuo. The residue was purified by prep-HPLC to afford 4-[6-(6-fluoro-4-methoxy-2-pyridyl)-5-methyl-7,8-dihydro-5H-pyrido[4,3-d]pyrimidin-2-yl]thiazole (27 mg) as a white solid. $^1$H NMR (400 MHz, Methanol-d$_4$) δ ppm: 9.12 (d, 1 H), 8.72 (s, 1 H), 8.49 (d, 1 H), 6.22 (s, 1 H), 5.86 (d, 1 H), 5.63 (q, 1 H), 4.42-4.53 (m, 1 H), 3.86 (s, 3 H), 3.41-3.53 (m, 1 H), 2.97-3.17 (m, 2 H), 1.55 (d, 3 H). MS obsd. (ESI$^+$) [(M+H)$^+$]: 358.

Example 6

2-[6-(6-Fluoro-4-methoxy-2-pyridyl)-5-methyl-7,8-dihydro-5H-pyrido[4,3-d]pyrimidin-2-yl]thiazole

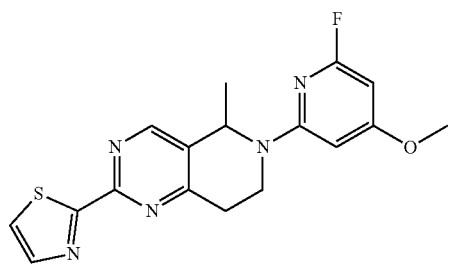

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), 2-(tributylstannyl) thiazole (364 mg, 0.97 mmol) and Xphos-Pd-G2 (25 mg, 0.03 mmol, CAS registry NO: 1310584-14-5) in 1,4-dioxane (4 mL) was degassed and charged with N$_2$. After being heated at 120° C. and stirred under nitrogen for 12 hrs, the resulting mixture was cooled to rt and concentrated in vacuo. The residue was purified by prep-HPLC to afford 2-[6-(6-fluoro-4-methoxy-2-pyridyl)-5-methyl-7,8-dihydro-5H-pyrido[4,3-d]pyrimidin-2-yl]thiazole (28 mg) as a white solid. $^1$H NMR (400 MHz, Methanol-d$_4$) δ ppm: 8.75 (s, 1 H), 8.02 (s, 1 H), 7.79 (s, 1 H), 6.22 (s, 1 H), 5.87 (d, 1 H), 5.66 (q, 1 H), 4.43-4.54 (m, 1 H), 3.86 (s, 3 H), 3.42-3.54 (m, 1 H), 2.99-3.20 (m, 2 H), 1.56 (d, 3 H). MS obsd. (ESI$^+$) [(M+H)$^+$]: 358.

Example 7

6-(6-Fluoro-4-methoxy-2-pyridyl)-5-methyl-2-(1-methylimidazol-2-yl)-7,8-dihydro-5H-pyrido[4,3-d]pyrimidine

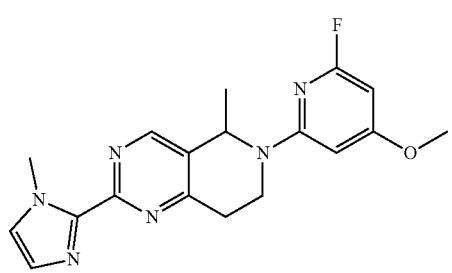 [SMILES: COc1cc(F)nc(N2CCc3nc(-c4nccn4C)ncc3C2C)c1]

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), 1-methyl-2-(tributylstannyl) imidazole (360 mg, 0.97 mmol) and Xphos-Pd-G2 (25 mg, 0.03 mmol, CAS registry NO: 1310584-14-5) in 1,4-dioxane (5 mL) was degassed and charged with N$_2$. After being heated at 110° C. and stirred under nitrogen for 12 hrs, the resulting mixture was cooled to rt and concentrated in vacuo. The residue was purified by prep-HPLC to afford 6-(6-fluoro-4-methoxy-2-pyridyl)-5-methyl-2-(1-methylimidazol-2-yl)-7,8-dihydro-5H-pyrido[4,3-d]pyrimidine (14 mg) as a white solid. ¹H NMR (400 MHz, DMSO-d₆) δ ppm: 8.73 (s, 1 H), 7.80 (s, 1 H), 7.63-7.73 (m, 1 H), 6.29 (s, 1 H), 5.97 (d, 1 H), 5.57 (q, 1 H), 4.35-4.45 (m, 1 H), 4.00 (s, 3 H), 3.84 (s, 3 H), 3.43-3.44 (m, 1 H), 2.84-3.04 (m, 2 H), 1.44 (d, 3 H). MS obsd. (ESI⁺) [(M+H)⁺]: 355.

Example 8

6-(6-Fluoro-4-methoxy-2-pyridyl)-5-methyl-2-(1-methylimidazol-4-yl)-7,8-dihydro-5H-pyrido[4,3-d]pyrimidine

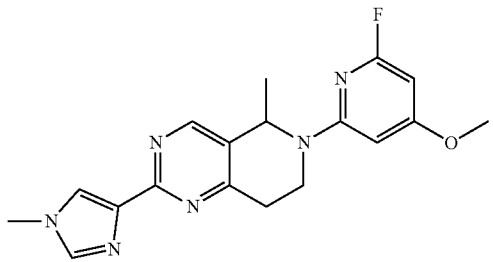

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), tributyl-(1-methylimidazol-4-yl)stannane (360 mg, 0.97 mmol) and precatalyst Xphos-Pd-G2 (25 mg, 0.03 mmol, CAS registry NO: 1310584-14-5) in dioxane (5 mL was degassed and charged with N₂. After being heated at 120° C. and stirred under nitrogen for 12 hrs, the resulting mixture was cooled to rt and concentrated in vacuo. The residue was purified by prep-HPLC to give 6-(6-fluoro-4-methoxy-2-pyridyl)-5-methyl-2-(1-methylimidazol-4-yl)-7,8-dihydro-5H-pyrido[4,3-d]pyrimidine (44 mg) as a yellow oil. ¹H NMR (400 MHz, CDCl₃) δ ppm: 8.49 (s, 1 H), 7.73 (s, 1 H), 7.69 (br s, 1 H), 6.00 (s, 1 H), 5.80 (d, 1 H), 5.54 (br d, 1 H), 4.37 (br d, 1 H), 3.85 (s, 3 H), 3.80 (s, 3 H), 3.36-3.48 (m, 1 H), 3.00-3.18 (m, 2 H), 1.50 (d, 3 H). MS obsd. (ESI⁺) [(M+H)⁺]: 355.

Example 9

6-(6-Fluoro-4-methoxy-2-pyridyl)-5-methyl-2-pyrazol-1-yl-7,8-dihydro-5H-pyrido[4,3-d]pyrimidine

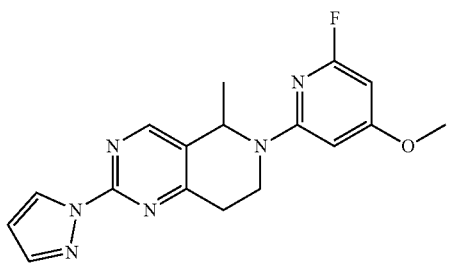 [SMILES: COc1cc(F)nc(N2CCc3nc(-n4cccn4)ncc3C2C)c1]

Step 1: preparation of 6-benzyl-2-pyrazol-1-yl-7,8-dihydro-5H-pyrido[4,3-d]pyrimidine

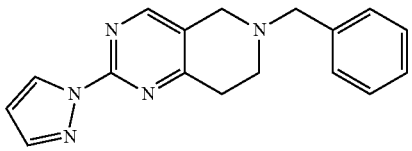 [SMILES: c1ccc(CN2CCc3nc(-n4cccn4)ncc3C2)cc1]

A mixture of 6-benzyl-2-chloro-7,8-dihydro-5H-pyrido[4,3-d]pyrimidine (2.4 g, 9.44 mmol, product of step 3 in example 2), pyrazole (771 mg, 11.32 mmol) and Cs₂CO₃ (4.6 g, 14.15 mmol) in CH₃CN (50 mL) was stirred at 80° C. for 12 hrs. After being cooled to rt, the reaction mixture was filtered and the filtrate was concentrated in vacuo. The residue was purified by column chromatography (eluting with DCM/MeOH=50/1, v:v) to afford 6-benzyl-2-pyrazol-1-yl-7,8-dihydro-5H-pyrido[4,3-d]pyrimidine (1.7 g) as a light yellow solid.

Step 2: preparation of 2-pyrazol-1-yl-5,6,7,8-tetrahydropyrido[4,3-d]pyrimidine

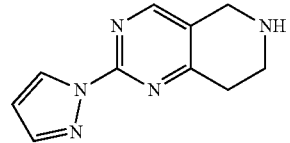

A mixture of 6-benzyl-2-pyrazol-1-yl-7,8-dihydro-5H-pyrido[4,3-d]pyrimidine (1.7 g, 5.83 mmol) and Pd/C (500 mg, 10 wt. %) in MeOH (35 mL) was stirred under hydrogen (45 psi) at rt for 16 hrs. The catalyst was filtered off and the filtrate was concentrated in vacuo. The residue was purified by column chromatography (eluting with DCM/MeOH=20/1, v:v) to give 2-pyrazol-1-yl-5,6,7,8-tetrahydropyrido[4,3-d]pyrimidine (800 mg) as a yellow solid.

Step 3: preparation of 6-(6-fluoro-4-methoxy-2-pyridyl)-2-pyrazol-1-yl-7,8-dihydro-5H-pyrido[4,3-d]pyrimidine

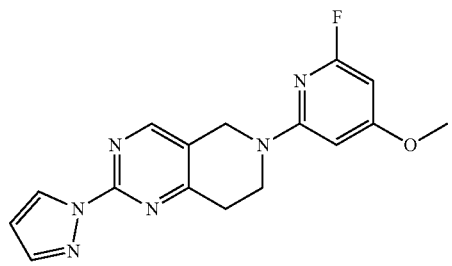 [SMILES: COc1cc(F)nc(N2CCc3nc(-n4cccn4)ncc3C2)c1]

A mixture of 2-pyrazol-1-yl-5,6,7,8-tetrahydropyrido[4,3-d]pyrimidine (800 mg, 3.98 mmol), 2,6-difluoro-4-methoxy-pyridine (865 mg, 5.96 mmol, the product of step 6 in Example 2) and K₂CO₃ (1.65 g, 11.93 mmol) in NMP (15 mL) was stirred at 140° C. under nitrogen for 2 hrs. After being cooled to rt, the reaction mixture was diluted with H₂O (30 mL) and extracted with EA (30 mL) for three times. The combined organic phase was washed with brine, dried over anhydrous Na₂SO₄ and concentrated in vacuo. The residue was purified by column chromatography (eluting with PE/EA=1/2, v:v) to give 6-(6-fluoro-4-methoxy-2-pyridyl)-2-pyrazol-1-yl-7,8-dihydro-5H-pyrido[4,3-d]pyrimidine (630 mg) as light yellow solid. ¹H NMR (400 MHz, CDCl₃) δ ppm: 8.59 (d, 1 H), 8.55 (s, 1 H), 7.82 (s, 1 H), 6.46-6.53 (m, 1 H), 6.00-6.05 (m, 1 H), 5.86 (d, 1 H), 4.72 (s, 2 H), 3.93 (t, 2 H), 3.86 (s, 3 H), 3.17 (t, 2 H). MS obsd. (ESI⁺) [(M+H)⁺]: 327.

Step 4: preparation of 6-(6-fluoro-4-methoxy-2-pyridyl)-5-methoxy-2-pyrazol-1-yl-7,8-dihydro-5H-pyrido[4,3-d]pyrimidine

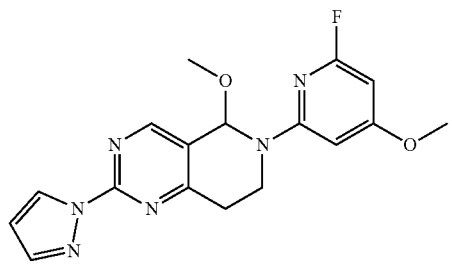

To a stirred mixture of 6-(6-fluoro-4-methoxy-2-pyridyl)-2-pyrazol-1-yl-7,8-dihydro-5H-pyrido[4,3-d]pyrimidine (630 mg, 1.93 mmol) in THF/MeOH/DCM (5 mL/5 mL/5 mL) was added RuCl₃ hydrate (87 mg, 0.39 mmol) and H₂O₂ (1.1 g, 9.65 mmol) at −70° C. slowly. The mixture was then warmed to rt and stirred for 24 hrs. The reaction was quenched with aqueous saturated Na₂SO₃ solution and the resulting mixture was extracted with DCM (20 mL) for three times. The combined organic phase was dried over anhydrous Na₂SO₄ and concentrated in vacuo to give crude 6-(6-fluoro-4-methoxy-2-pyridyl)-5-methoxy-2-pyrazol-1-yl-7,8-dihydro-5H-pyrido[4,3-d]pyrimidine (340 mg) which was used directly in the next step.

Step 5: preparation of 6-(6-fluoro-4-methoxy-2-pyridyl)-5-methyl-2-pyrazol-1-yl-7,8-dihydro-5H-pyrido[4,3-d]pyrimidine

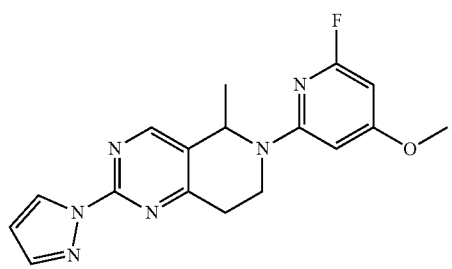 [SMILES: COc1cc(F)nc(N2CCc3nc(-n4cccn4)ncc3C2C)c1]

To a stirred solution of crude 6-(6-fluoro-4-methoxy-2-pyridyl)-5-methoxy-2-pyrazol-1-yl-7,8-dihydro-5H-pyrido[4,3-d]pyrimidine (340 mg, 0.95 mmol) in THF (7 mL) was added BF₃.Et₂O (406 mg, 2.86 mmol) at −70° C. The mixture was stirred for 10 mins at −70° C. and to the reaction mixture was added a solution of CH₃MgBr (3.0 mL, 2.86 mmol) in Et₂O slowly. After being warmed to −20° C. and stirred for 1 hr, the resulting mixture wad diluted with aqueous saturated NH₄Cl solution (10 mL) and extracted with EA (10 mL) for three times. The combined organic phase was dried over anhydrous Na₂SO₄ and concentrated in vacuo. The residue was purified by prep-HPLC to give 6-(6-fluoro-4-methoxy-2-pyridyl)-5-methyl-2-pyrazol-1-yl-7,8-dihydro-5H-pyrido[4,3-d]pyrimidine (17 mg) as a white solid. ¹H NMR (400 MHz, Methanol-d₄) δ ppm: 8.66-8.70 (m, 2 H), 7.83 (d, 1 H), 6.58 (dd, 1 H), 6.22 (s, 1 H), 5.87 (d, 1 H), 5.64 (q, 1H), 4.49 (dd, 1 H), 3.86 (s, 3 H), 3.41-3.54 (m, 1 H), 2.97-3.16 (m, 2 H), 1.54 (d, 3 H). MS obsd. (ESI⁺) [(M+H)⁺]: 341.

Example 10

2-(1-Benzylimidazol-4-yl)-6-(6-fluoro-4-methoxy-2-pyridyl)-5-methyl-7,8-dihydro-5H-pyrido[4,3-d]pyrimidine

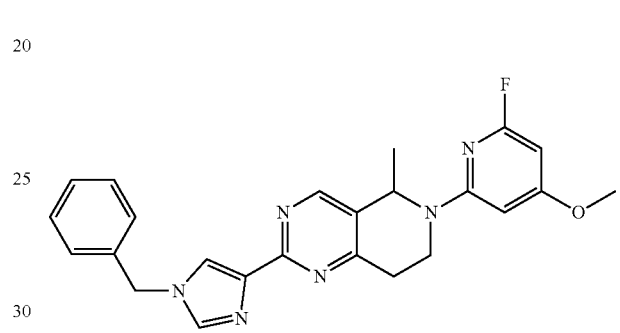

Step 1: preparation of 1-benzyl-4-iodo-imidazole

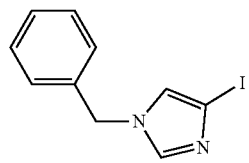 [SMILES: Ic1cn(Cc2ccccc2)cn1]

A mixture of 4-iodoimidazole (2.5 g, 12.89 mmol), Cs₂CO₃ (6.3 g, 19.33 mmol) and BnBr (2.6 g, 15.47 mmol) in CH₃CN (50 mL) was stirred at 80° C. for 12 hrs. After being cooled to rt, the solid was filtered and the filtrate was concentrated in vacuo. The residue was purified by prep-HPLC to give 1-benzyl-4-iodo-imidazole (2.68 g) as a white solid.

Step 2: preparation of (1-benzylimidazol-4-yl)-tributyl-stannane

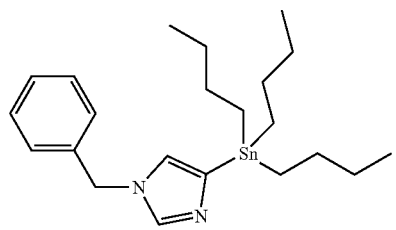 [SMILES: CCC[CH2][Sn]([CH2]CCC)([CH2]CCC)[c]1cn(Cc2ccccc2)cn1]

To a stirred solution of 1-benzyl-4-iodo-imidazole (500 mg, 1.76 mmol) in THF (10 mL) was added a solution of EtMgBr (0.7 mL, 2.11 mmol) in Et$_2$O slowly at rt. The reaction mixture was stirred for 1 hr and then to the reaction mixture was added n-Bu$_3$SnCl (1.24 g, 3.81 mmol) slowly. The reaction mixture was then stirred at rt for15 hrs. After the reaction was quenched with aqueous saturated NH$_4$Cl solution (5 mL), the resulting mixture was extracted with EA (30 mL) for three times. The combined organic phase was washed with brine (20 mL), dried over anhydrous Na$_2$SO$_4$ and concentrated in vacuo to give (1-benzylimidazol-4-yl)-tributyl-stannane (580 mg) as a crude product which was used directly in the next step.

Step 3: preparation of 2-(1-benzylimidazol-4-yl)-6-(6-fluoro-4-methoxy-2-pyridyl)-5-methyl-7,8-dihydro-5H-pyrido[4,3-d]pyrimidine

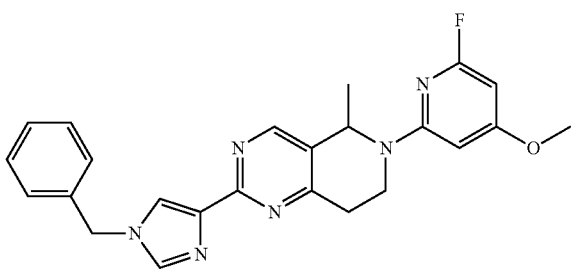 [SMILES: COc1cc(F)nc(N2CCc3nc(-c4cn(Cc5ccccc5)cn4)ncc3C2C)c1]

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), (1-benzylimidazol-4-yl)-tributyl-stannane (436 mg, 0.97 mmol) and Xphos-Pd-G2 Precatalyst (26 mg, 0.03 mmol, CAS registry NO: 1310584-14-5) in 1,4-dioxane (5 mL) was degassed and charged with N2. After being heated at 110° C. and stirred under nitrogen for 12 hrs, the resulting mixture was cooled to rt and concentrated in vacuo. The residue was purified by prep-HPLC to afford 2-(1-benzylimidazol-4-yl)-6-(6-fluoro-4-methoxy-2-pyridyl)-5-methyl-7,8-dihydro-5H-pyrido[4,3-d]pyrimidine (41 mg) as a yellow solid. $^1$H NMR (400 MHz, Methanol-d$_4$) δ ppm: 8.39 (s, 1 H), 7.90-8.09 (m, 2 H), 7.30-7.50 (m, 5 H), 6.17 (s, 1 H), 5.87 (s, 1 H), 5.55 (q, 1 H), 5.31 (s, 2 H), 4.38 (br d, 1H), 3.85 (s, 3 H), 3.37-3.49 (m, 1 H), 2.90-3.11 (m, 2 H) 1.40 (br s, 3 H). MS obsd. (ESI$^+$) [(M+H)$^+$]: 431.

Example 11

2-Fluoro-N,N-dimethyl-6-(5-methyl-2-thiazol-4-yl-7,8-dihydro-5H-pyrido[4,3-d]pyrimidin-6-yl)pyridin-4-amine

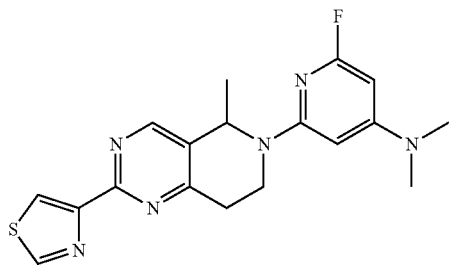 [SMILES: CC1c2cnc(-c3cscn3)nc2CCN1c1cc(N(C)C)cc(F)n1]

Step 1: preparation of thiazole-4-carboxamide

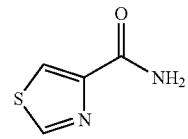

A mixture of thiazole-4-carboxylic acid (10.0 g, 77.4 mmol) and SOCl$_2$ (100 mL) was stirred for 5 hrs at 60° C. The resulting reaction mixture was then cooled and concentrated in vacuo and the residue was dissolved in THF (100 mL). To the solution was added ammonium hydroxide (18.1 mL, 465 mmol) slowly at 0° C. The resulting mixture was stirred for one hour at rt, then diluted with water (100 mL) and extracted in DCM (50 mL) for three times. The combined organic layer was dried over anhydrous Na$_2$SO$_4$ and concentrated in vacuo to give crude thiazole-4-carboxamide (10.3 g) as yellow solid, which was used in the next step.

Step 2: preparation of thiazole-4-carbonitrile

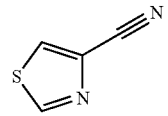

To a solution of thiazole-4-carboxamide (10.0 g, 67.1 mmol) in THF (150 mL) were slowly added triethylamine (42.1 mL, 302 mmol) and TFAA (19 mL, 134 mmol) at 0° C. successively. After being slowly warmed to rt and stirred for 18 hrs, the reaction mixture was diluted with H$_2$O (100 mL) and extracted in DCM (50 mL) for three times. The combined organic phase was concentrated in vacuo and the residue was purified by column chromatography (eluting with PE/EA=5/1, v:v) to give thiazole-4-carbonitrile (7.6 g) as yellow oil.

Step 3: preparation of thiazole-4-carboxamidine hydrochloride

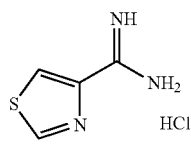

To a solution of thiazole-4-carbonitrile (7.6 g, 64.2 mmol) in anhydrous MeOH (50 mL) was added sodium methoxide (1.73 g, 32.1 mmol) and the resulting mixture was stirred for 16 hrs at rt. To the resulting mixture was added ammonium chloride (4.46 g, 83.4 mmol).After being stirred for 3 hrs at 80° C., the resulting mixture was cooled to rt and filtered. The filtrate was concentrated in vacuo to give crude thiazole-4-carboxamidine hydrochloride (10.4 g), which was directly used in the next step.

Step 4: preparation of benzyl 2-methyl-4-oxo-2,3-dihydropyridine-1-carboxylate

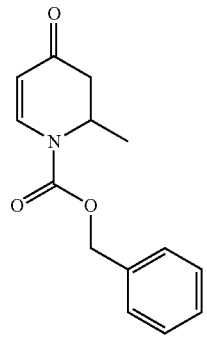 [SMILES: CC1CC(=O)C=CN1C(=O)OCc1ccccc1]

To a stirred solution of 4-methoxypyridine (50.0 g, 458 mmol) in anhydrous THF (500 mL) was added a solution of benzyl chloroformate (50.0 g, 458 mmol) in anhydrous THF (400 mL) at −25° C. After being stirred for 1 hr at the same temperature, the reaction mixture was cooled to −40° C., followed by drop-wise addition of methylmagnesium bromide (3.0 M in diethyl ether, 183 mL, 550 mmol). The cooling bath was removed and the resulting mixture was stirred at rt for 0.5 hr and then poured into 10% aqueous HCl (1 L). The resulting mixture was stirred at rt for 10 mins, and then extracted with EA (2 L) twice. The organic layers were combined and washed sequentially with saturated aqueous NaHCO₃ (1 L) and brine (1 L), dried over anhydrous Na₂SO₄ and concentrated in vacuo. The residue was purified by column chromatography (eluting with PE/EA=10/1, v:v) to give benzyl 2-methyl-4-oxo-2,3-dihydropyridine-1-carboxylate (105 g) as a colorless oil.

Step 5: preparation of O1-benzyl O3-ethyl 2-methyl-4-oxo-2,3-dihydropyridine-1,3-dicarboxylate

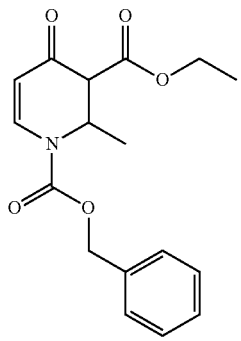 [SMILES: CCOC(=O)C1C(=O)C=CN(C(=O)OCc2ccccc2)C1C]

To a solution of benzyl 2-methyl-4-oxo-2,3-dihydropyridine-1-carboxylate (100.0 g, 400 mmol) in THF (1 L) was added lithium bis(trimethylsilyl)amide (1.0 M in THF, 960 mL, 960 mmol) drop-wise at −70° C. The mixture was stirred at this temperature for 1 hr. And then to the resulting mixture was added ethyl chloroformate (55.4 g, 440 mmol). After being stirred at −70° C. for additional 3 hrs, the resulting reaction mixture was diluted with saturated aqueous NH₄Cl (300 mL), and then extracted with EA (3 L). The organic layer was washed sequentially with water (1 L) and brine (1 L), then dried over anhydrous Na₂SO₄ and concentrated in vacuo to give O1-benzyl O3-ethyl 2-methyl-4-oxo-2,3-dihydropyridine-1,3-dicarboxylate (110 g, crude) as a yellow oil.

Step 6: preparation of O1-benzyl O3-ethyl 2-methyl-4-oxo-piperidine-1,3-dicarboxylate

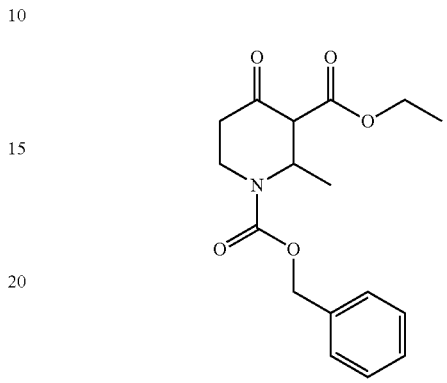

To a solution of O1-benzyl O3-ethyl 2-methyl-4-oxo-2,3-dihydropyridine-1,3-dicarboxylate (110 g, 347 mmol) in acetic acid (1 L) was added Zn (113 g, 1733 mmol) portion-wise. After being heated at 75° C. with stiffing for 3 hrs, the reaction mixtures were filtered and the filtrate was concentrated in vacuo. The residue was diluted with EA (3 L), washed sequentially with water (1 L), aqueous NaHCO₃ (500 mL) and brine (1 L), and then concentrated in vacuo. The residue was purified by column chromatography to give O1-benzyl O3-ethyl 2-methyl-4-oxo-piperidine-1,3-dicarboxylate (53 g) as a yellow oil.

Step 7: preparation of benzyl 4-hydroxy-5-methyl-2-thiazol-4-yl-7,8-dihydro-5H-pyrido[4,3-d]pyrimidine-6-carboxylate

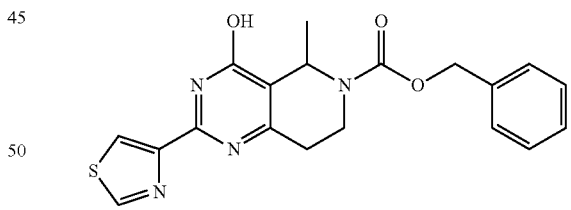

To a solution crude of thiazole-4-carboximidamide hydrochloride (7 g) in trifluoroethanol (100 mL) was added O1-benzyl O3-ethyl 2-methyl-4-oxo-piperidine-1,3-dicarboxylate (8.87 g, 27.8 mmol) and potassium carbonate (9.61 g, 69.5 mmol). The reaction mixture was stirred for 16 hrs at 65° C. After being cooled to rt, the reaction mixture was filtered and the filtrate was washed with brine and extracted in EA (100 mL) for three times. The combined organic layer was dried over anhydrous Na₂SO₄ and concentrated in vacuo. The residue was purified by column chromatography (eluting with DCM/MeOH=20/1, v:v) to give benzyl 4-hydroxy-5-methyl-2-thiazol-4-yl-7,8-dihydro-5H-pyrido[4,3-d]pyrimidine-6-carboxylate (8.8 g) as yellow solid.

Step 8: preparation of benzyl 4-chloro-5-methyl-2-thiazol-4-yl-7,8-dihydro-5H-pyrido[4,3-d]pyrimidine-6-carboxylate

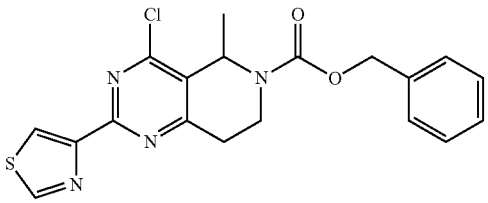 [SMILES: CC1c2c(O)nc(-c3cscn3)nc2CCN1C(=O)OCc1ccccc1]

To a solution of benzyl 4-hydroxy-5-methyl-2-thiazol-4-yl-7,8-dihydro-5H-pyrido[4,3-d]pyrimidine-6-carboxylate (8.8 g, 19.6 mmol) in acetonitrile (100 mL) was added POCl$_3$ (4.56 mL, 48.9 mmol). After being stirred for 2 hrs at 60° C., the resulting mixture was cooled to rt and concentrated in vacuo to give crude benzyl 4-chloro-5-methyl-2-thiazol-4-yl-7,8-dihydro-5H-pyrido[4,3-d]pyrimidine-6-carboxylate (8.2 g) which was directly used in the next step.

Step 9: preparation of benzyl 5-methyl-2-thiazol-4-yl-7,8-dihydro-5H-pyrido[4,3-d]pyrimidine-6-carboxylate

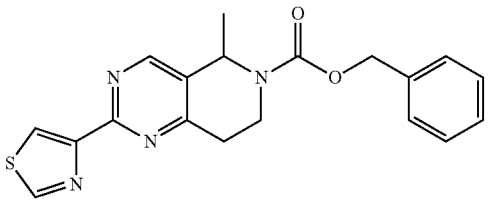 [SMILES: CC1c2cnc(-c3cscn3)nc2CCN1C(=O)OCc1ccccc1]

To a solution of benzyl 4-chloro-5-methyl-2-thiazol-4-yl-7,8-dihydro-5H-pyrido[4,3-d]pyrimidine-6-carboxylate (3.0 g) in a mixture of EtOH (40 mL), water (10 mL) and ammonium hydroxide (10 mL) was added Pd/C (6.0 g, 10 wt. %). The reaction mixture was stirred for 20 hrs at rt under atmosphere of hydrogen. The catalyst was filtered off and the filtrate was concentrated in vacuo to give crude 5-methyl-2-thiazol-4-yl-7,8-dihydro-5H-pyrido[4,3-d]pyrimidine-6-carboxylate (2.5 g) which was used in next step directly.

Step 10: preparation of 4-(5-methyl-5,6,7,8-tetrahydropyrido[4,3-d]pyrimidin-2-yl)thiazole

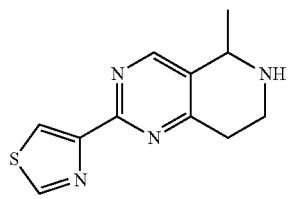 [SMILES: CC1NCCc2nc(-c3cscn3)ncc21]

A suspension of benzyl 5-methyl-2-thiazol-4-yl-7,8-dihydro-5H-pyrido[4,3-d]pyrimidine-6-carboxylate (2.5 g) in hydrochloric acid (15 mL) was stirred for 1 hr at 80° C. After being cooled to rt, the reaction mixture was basified with saturated aqueous NaHCO$_3$ solution and extracted with a mixture of chloroform and isopropanol (v:v=3:1, 50 mL) for three times. The combined extracts were dried over anhydrous Na$_2$SO$_4$ and concentrated in vacuo to give crude 4-(5-methyl-5,6,7,8-tetrahydropyrido[4,3-d]pyrimidin-2-yl)thiazole (1.2 g) which was used in next step directly.

Step 11: preparation of 4-[6-(6-fluoro-4-iodo-2-pyridyl)-5-methyl-7,8-dihydro-5H-pyrido[4,3-d]pyrimidin-2-yl]thiazole

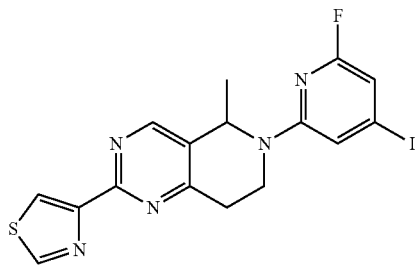 [SMILES: CC1c2cnc(-c3cscn3)nc2CCN1c1cc(I)cc(F)n1]

To a solution of 4-(5-methyl-5,6,7,8-tetrahydropyrido[4,3-d]pyrimidin-2-yl)thiazole (300 mg, 1.29 mmol) in DMSO (5 mL) was added 2,6-difluoro-4-iodopyridine (373 mg, 1.55 mmol) and NaHCO$_3$ (542 mg, 6.45 mmol) and the resulting mixture was stirred for 18 hrs at 80° C. After being cooled to rt, the resulting reaction mixture was filtered and the filtrate was diluted with brine and extracted in DCM (30 mL) for three times. The combined organic layer was dried over anhydrous Na$_2$SO$_4$ and concentrated in vacuo. The residue was purified by column chromatography (eluting with DCM/MeOH=20/1, v:v) to give 4-[6-(6-fluoro-4-iodo-2-pyridyl)-5-methyl-7,8-dihydro-5H-pyrido[4,3-d]pyrimidin-2-yl]thiazole (520 mg) as yellow solid.

Step 12: preparation of 2-fluoro-N,N-dimethyl-6-(5-methyl-2-thiazol-4-yl-7,8-dihydro-5H-pyrido[4,3-d]pyrimidin-6-yl)pyridin-4-amine

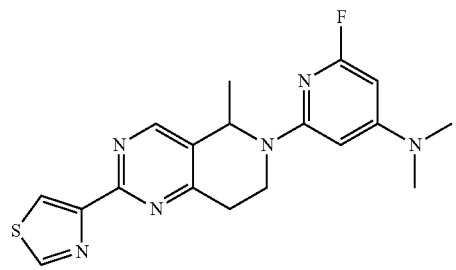 [SMILES: CC1c2cnc(-c3cscn3)nc2CCN1c1cc(N(C)C)cc(F)n1]

To a solution of 4-[6-(6-fluoro-4-iodo-2-pyridyl)-5-methyl-7,8-dihydro-5H-pyrido[4,3-d]pyrimidin-2-yl]thiazole (100 mg, 221 µmol) in dioxane (5 mL) was added dimethylamine hydrochloride (54 mg, 662 µmol), cesium carbonate (359 mg, 1.1 mmol), Xantphos (25.5 mg, 44.1 µmol) and Pd(OAc)$_2$ (4.95 mg, 22.1 µmol). The resulting mixture was stirred for 20 hrs at 100° C. under atmosphere of argon. After being cooled to rt, the resulting reaction mixture was filtered and the filtrate was concentrated in vacuo. The residue was purified by prep-HPLC to give 2-fluoro-N,N-dimethyl-6-(5-methyl-2-thiazol-4-yl-7,8-dihydro-5H-pyrido[4,3-d]pyrimidin-6-yl)pyridin-4-amine (14 mg) as pale yellow solid. $^1$H NMR (400 MHz, DMSO-d$_6$) δ ppm: 9.20 (d, 1H), 8.80 (s, 1H), 8.50 (d, 1H), 5.84 (s, 1H), 5.66 (s, 1H), 5.64-5.59 (m, 1H), 4.46-4.38 (m, 1H), 3.42-3.34 (m, 1H), 3.02-2.93 (m, 8H), 1.45 (d, 3H). MS obsd. (ESI$^+$) [(M+H)$^+$]: 371.

Example 12, 13 and 14

4-[6-Fluoro-4-(5-methyl-2-thiazol-4-yl-7,8-dihydro-5H-pyrido[4,3-d]pyrimidin-6-yl)-2-pyridyl]morpholine and 4-[2-fluoro-6-(5-methyl-2-thiazol-4-yl-7,8-dihydro-5H-pyrido[4,3-d]pyrimidin-6-yl)-4-pyridyl]morpholine and 4-[4-fluoro-6-(5-methyl-2-thiazol-4-yl-7,8-dihydro-5H-pyrido[4,3-d]pyrimidin-6-yl)-2-pyridyl]morpholine Example 12

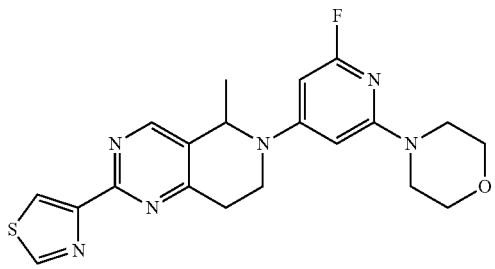

Example 13

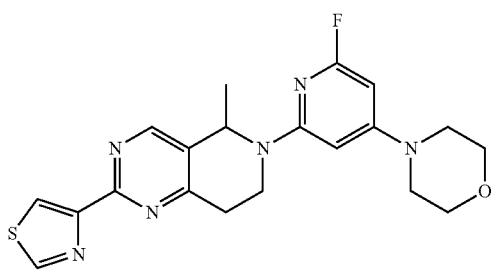

Example 14

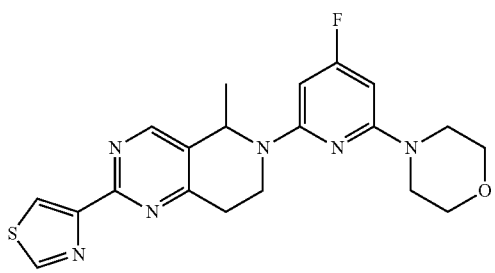

To a solution of 4-(5-methyl-5,6,7,8-tetrahydropyrido[4,3-d]pyrimidin-2-yl)thiazole (the product of step 10 in Example 11, 200 mg, 861 μmol) in DMSO (2 mL) was added DIPEA (3 mL) and 2,4,6-trifluoropyridine (149 mg, 1.12 mmol). The resulting mixture was stirred for 2 hrs at 150° C. under microwave irradiation. After the reaction mixture being cooled to rt, to the resulting mixture was added morpholine (225 mg, 2.58 mmol). The resulting mixture was stirred for another 18 hrs at 130° C., then cooled to rt and concentrated in vacuo. The residue was purified by prep-HPLC to give 4-[6-fluoro-4-(5-methyl-2-thiazol-4-yl-7,8-dihydro-5H-pyrido[4,3-d]pyrimidin-6-yl)-2-pyridyl]morpholine (57 mg) as light yellow solid and 4-[2-fluoro-6-(5-methyl-2-thiazol-4-yl-7,8-dihydro-5H-pyrido[4,3-d]pyrimidin-6-yl)-4-pyridyl]morpholine (40 mg) as light yellow solid and 4-[4-fluoro-6-(5-methyl-2-thiazol-4-yl-7,8-dihydro-5H-pyrido[4,3-d]pyrimidin-6-yl)-2-pyridyl]morpholine (19 mg) as light yellow solid.

Example 12: 4-[6-fluoro-4-(5-methyl-2-thiazol-4-yl-7,8-dihydro-5H-pyrido[4,3-d]pyrimidin-6-yl)-2-pyridyl]morpholine, $^1$H NMR (400 MHz, DMSO-d$_6$) δ ppm: 9.21 (d, 1 H), 8.73 (s, 1 H), 8.51 (d, 1H), 6.07 (s, 1H), 6.02 (s, 1H), 5.41-5.31 (m, 1H), 4.17-4.09 (m, 1H), 3.71-3.63 (m, 4H), 3.53-3.44 (m, 1H), 3.43-3.36 (m, 4H), 3.11-2.92 (m, 2H), 1.47 (d, 3H). MS obsd. (ESI$^+$) [(M+H)$^+$]: 413.

Example 13: 4-[2-fluoro-6-(5-methyl-2-thiazol-4-yl-7,8-dihydro-5H-pyrido[4,3-d]pyrimidin-6-yl)-4-pyridyl]morpholine, $^1$H NMR (400 MHz, DMSO-d$_6$) δ ppm: 9.20 (d, 1H), 8.79 (s, 1H), 8.50 (d, 1H), 6.11 (s, 1H), 5.89 (s, 1H), 5.68-5.58 (m, 1H), 4.51-4.36 (m, 1 H), 3.73-3.68 (m, 4 H), 3.43-3.35 (m, 1H), 3.30-3.25 (m, 4H), 3.05-2.90 (m, 2H), 1.45 (d, 3H). (ESI$^+$) [(M+H)$^+$]: 413.

Example 14: 4-[4-fluoro-6-(5-methyl-2-thiazol-4-yl-7,8-dihydro-5H-pyrido[4,3-d]pyrimidin-6-yl)-2-pyridyl]morpholine, $^1$H NMR (400 MHz, DMSO-d$_6$) δ ppm: 9.20 (d, 1H), 8.78 (s, 1H), 8.50 (d, 1H), 6.16-6.06 (m, 1H), 5.97-5.90 (m, 1H), 5.67-5.59 (m, 1H), 4.50-4.41 (m, 1H), 3.74-3.64 (m, 4H), 3.47-3.41 (m, 4H), 3.40-3.34 (m, 1H), 3.07-2.89 (m, 2H), 1.46 (d, 3H). (ESI$^+$) [(M+H)$^+$]: 413.

Example 15 and 16

4-[6-(6-Fluoro-4-methoxy-2-pyridyl)-5-methyl-7,8-dihydro-5H-pyrido[4,3-d]pyrimidin-2-yl]-2-methyl-thiazole and 5-[6-(6-fluoro-4-methoxy-2-pyridyl)-5-methyl-7,8-dihydro-5H-pyrido[4,3-d]pyrimidin-2-yl]-2-methyl-thiazole Example 15

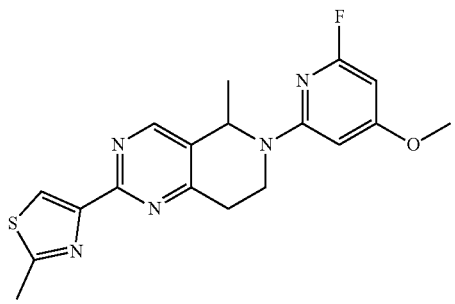

Example 16

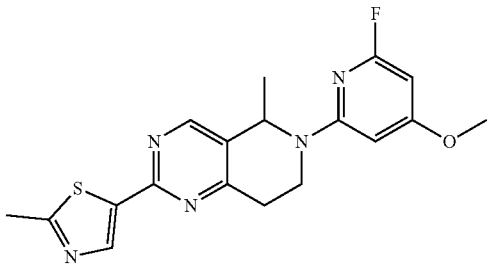

Step 1: preparation of tributyl-(2-methylthiazol-4-yl)stannane

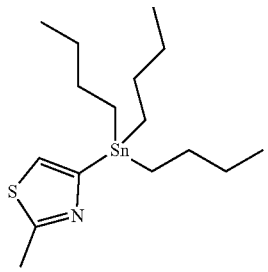 [SMILES: CCC[CH2][Sn]([CH2]CCC)([CH2]CCC)[c]1csc(C)n1]

To a stirred solution of 4-bromo-2-methylthiazole (200 mg, 1.12 mmol) in THF (4 mL) was added n-BuLi (0.5 mL, 1.35 mmol, in hexane) slowly at −70° C., and the reaction mixture was stirred for 1 hr at −70° C. To the resulting mixture was added a solution of n-Bu₃SnCl (590 mg, 1.81 mmol) in THF (2 mL) slowly. After being stirred at −70° C. for additional 1 hr, the resulting mixture was diluted with aqueous saturated HN₄Cl (2 mL) solution and extracted with EA (20 mL) for three times. The combined organic phase was dried over anhydrous Na₂SO₄, concentrated in vacuo to give crude tributyl-(2-methylthiazol-4-yl)stannane (380 mg) which was used directly in the next step.

Step 2: preparation of 4-[6-(6-fluoro-4-methoxy-2-pyridyl)-5-methyl-7,8-dihydro-5H-pyrido[4,3-d]pyrimidin-2-yl]-2-methyl-thiazole and 5-[6-(6-fluoro-4-methoxy-2-pyridyl)-5-methyl-7,8-dihydro-5H-pyrido[4,3-d]pyrimidin-2-yl]-2-methyl-thiazole Example 15

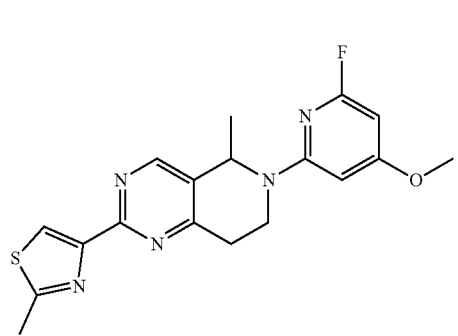

Example 16

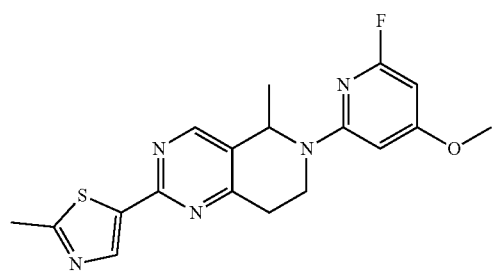

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), tributyl-(2-methylthiazol-4-yl)stannane (crude 377 mg, 0.97 mmol) and Xphos-Pd-G2 (51 mg, 0.06 mmol, CAS registry NO: 1310584-14-5) in 1,4-dioxane (5 mL) was heated at 120° C. and stirred under nitrogen for 12 hrs. After being cooled to rt, the reaction mixture was concentrated in vacuo and the residue was purified by prep-HPLC to afford 4-[6-(6-fluoro-4-methoxy-2-pyridyl)-5-methyl-7,8-dihydro-5H-pyrido[4,3-d]pyrimidin-2-yl]-2-methyl-thiazole (5 mg) as light yellow solid and 5-[6-(6-fluoro-4-methoxy-2-pyridyl)-5-methyl-7,8-dihydro-5H-pyrido[4,3-d]pyrimidin-2-yl]-2-methyl-thiazole (22 mg) as light yellow solid.

Example 15: 4-[6-(6-fluoro-4-methoxy-2-pyridyl)-5-methyl-7,8-dihydro-5H-pyrido[4,3-d]pyrimidin-2-yl]-2-methyl-thiazole, ¹H NMR (400 MHz, Methanol-d₄) δ ppm: 8.70 (s, 1H), 8.26 (s, 1 H), 6.22 (s, 1 H), 5.86 (d, 1 H), 5.62 (q, 1 H), 4.42-4.54 (m, 1 H), 3.86 (s, 3 H), 3.40-3.55 (m, 1H), 2.97-3.16 (m, 2H), 2.79 (s, 3H), 1.54 (d, 3 H). MS obsd. (ESI⁺) [(M+H)⁺]: 372.

Example 16: 5-[6-(6-fluoro-4-methoxy-2-pyridyl)-5-methyl-7,8-dihydro-5H-pyrido[4,3-d]pyrimidin-2-yl]-2-methyl-thiazole. ¹H NMR (400 MHz, Methanol-d₄) δ ppm: 8.62 (s, 1 H), 8.36 (s, 1 H), 6.20 (s, 1 H), 5.86 (d, 1 H), 5.59 (q, 1 H), 4.46 (br dd, 1 H), 3.86 (s, 3 H), 3.39-3.54 (m, 1 H), 2.90-3.13 (m, 2 H), 2.74 (s, 3 H), 1.52 (d, 3 H). MS obsd. (ESI⁺) [(M+H)⁺]: 372.

Example 17, 18 and 19

4-[6-(2-Fluoro-6-pyrrolidin-1-yl-4-pyridyl)-5-methyl-7,8-dihydro-5H-pyrido[4,3-d]pyrimidin-2-yl]thiazole and 4-[6-(6-fluoro-4-pyrrolidin-1-yl-2-pyridyl)-5-methyl-7,8-dihydro-5H-pyrido[4,3-d]pyrimidin-2-yl]thiazole and 4-[6-(4-fluoro-6-pyrrolidin-1-yl-2-pyridyl)-5-methyl-7,8-dihydro-5H-pyrido[4,3-d]pyrimidin-2-yl]thiazole Example 17

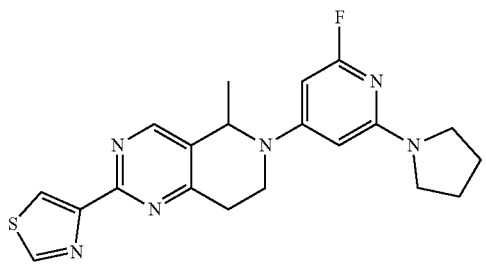

Example 18

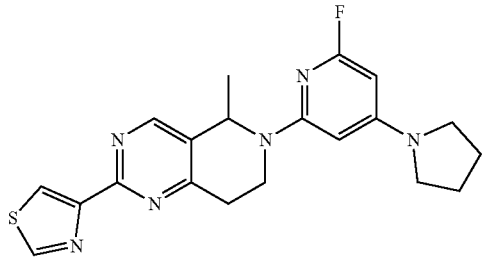

Example 19

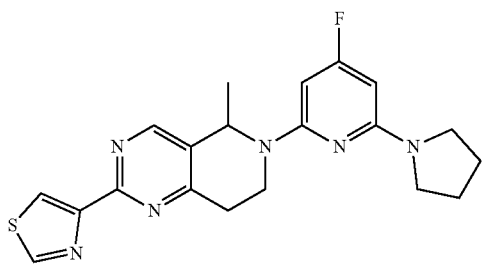

To a solution of 4-(5-methyl-5,6,7,8-tetrahydropyrido[4,3-d]pyrimidin-2-yl)thiazole (the product of step 10 in Example 11, 200 mg, 861 μmol) in DMSO (2 mL) was added DIPEA (3 mL) and 2,4,6-trifluoropyridine (149 mg, 1.12 mmol). The mixture was stirred for 2 hrs at 150° C. under microwave irradiation and cooled to rt. Then to the cooled mixture was added pyrrolidine (122 mg, 1.72 mmol). The resulting mixture was stirred for another 18 hrs at 130° C., then cooled to rt and concentrated in vacuo. The residue was purified by prep-HPLC to give 4-[6-(2-fluoro-6-pyrrolidin-1-yl-4-pyridyl)-5-methyl-7,8-dihydro-5H-pyrido[4,3-d]pyrimidin-2-yl]thiazole (60 mg) as light yellow solid and 4-[6-(6-fluoro-4-pyrrolidin-1-yl-2-pyridyl)-5-methyl-7,8-dihydro-5H-pyrido[4,3-d]pyrimidin-2-yl]thiazole (50 mg) as light yellow solid and 4-[6-(4-fluoro-6-pyrrolidin-1-yl-2-pyridyl)-5-methyl-7,8-dihydro-5H-pyrido[4,3-d]pyrimidin-2-yl]thiazole (14 mg) as light yellow solid.

Example 17: 4-[6-(2-fluoro-6-pyrrolidin-1-yl-4-pyridyl)-5-methyl-7,8-dihydro-5H-pyrido[4,3-d]pyrimidin-2-yl]thiazole, $^1$H NMR (400 MHz, DMSO-d$_6$) δ ppm: 9.21 (d, 1H), 8.76 (s, 1H), 8.51 (d, 1H), 5.89 (s, 1H), 5.67 (s, 1H), 5.38-5.28 (m, 1H), 4.14-4.00 (m, 1H), 3.55-3.44 (m, 1H), 3.34-3.27 (m, 4H), 3.12-2.90 (m, 2H), 1.96-1.87 (m, 4H), 1.47 (d, 3H). MS obsd. (ESI$^+$) [(M+H)$^+$]: 397.

Example 18: 4-[6-(6-fluoro-4-pyrrolidin-1-yl-2-pyridyl)-5-methyl-7,8-dihydro-5H-pyrido[4,3-d]pyrimidin-2-yl]thiazole, $^1$H NMR (400 MHz, DMSO-d$_6$) δ ppm: 9.21 (d, 1H), 8.80 (s, 1H), 8.50 (d, 1H), 5.72 (s, 1H), 5.65-5.54(m, 1H), 5.52 (s, 1H), 4.48-4.36 (m, 1H), 3.42-3.35 (m, 1H), 3.29-3.22 (m, 4H), 3.07-2.89 (m, 2H), 2.01-1.86 (m, 4H), 1.45 (d, 3H). MS obsd. (ESI$^+$) [(M+H)$^+$]: 397.

Example 19: 4-[6-(4-fluoro-6-pyrrolidin-1-yl-2-pyridyl)-5-methyl-7,8-dihydro-5H-pyrido[4,3-d]pyrimidin-2-yl]thiazole, $^1$H NMR (400 MHz, DMSO-d$_6$) δ ppm: 9.20 (d, 1H), 8.78 (s, 1H), 8.49 (d, 1H), 5.96-5.91 (m, 1H), 5.72-5.60 (m, 1H), 5.58-5.43 (m, 1H), 4.49-4.45 (m, 1H), 3.42-3.34 (m, 5H), 3.07-2.89 (m, 2H), 1.99-1.87 (m, 4H), 1.47 (d, 3H). MS obsd. (ESI$^+$) [(M+H)$^+$]: 397.

Example 20, 21 and 22

4-[6-[2-Fluoro-6-(4-methylsulfonylpiperazin-1-yl)-4-pyridyl]-5-methyl-7,8-dihydro-5H-pyrido[4,3-d]pyrimidin-2-yl]thiazole and 4-[6-[6-fluoro-4-(4-methylsulfonylpiperazin-1-yl)-2-pyridyl]-5-methyl-7,8-dihydro-5H-pyrido[4,3-d]pyrimidin-2-yl]thiazole and 4-[6-[4-fluoro-6-(4-methylsulfonylpiperazin-1-yl)-2-pyridyl]-5-methyl-7,8-dihydro-5H-pyrido[4,3-d]pyrimidin-2-yl]thiazole Example 20

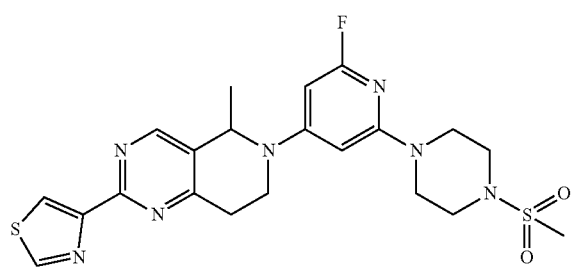

Example 21

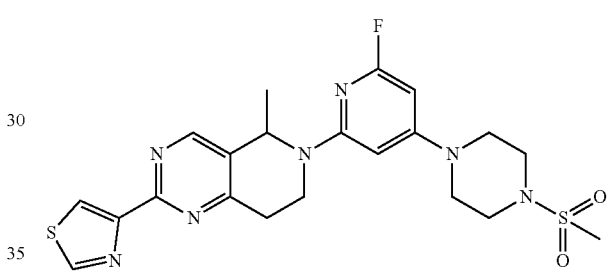

Example 22

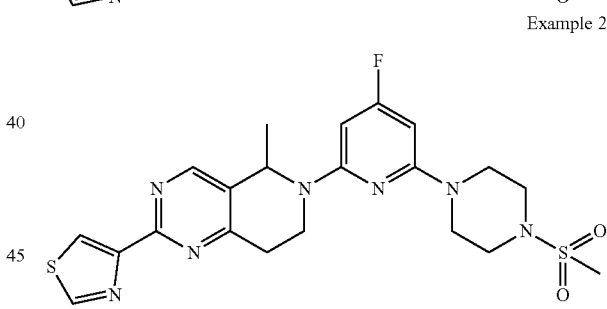

To a solution of 4-(5-methyl-5,6,7,8-tetrahydropyrido[4,3-d]pyrimidin-2-yl)thiazole (the product of step 10 in Example 11, 200 mg, 861 μmol) in DMSO (2 mL) was added DIPEA (3 mL) and 2,4,6-trifluoropyridine (149 mg, 1.12 mmol). The mixture was stirred for 2 hrs at 150° C. under microwave irradiation, and cooled to rt. Then to the cooled mixture was added 1-(methylsulfonyl)piperazine (283 mg, 1.72 mmol). The resulting mixture was stirred for another 18 hrs at 130° C., then cooled to rt and concentrated in vacuo. The residue was purified by prep-HPLC to give 4-[6-[2-fluoro-6-(4-methylsulfonylpiperazin-1-yl)-4-pyridyl]-5-methyl-7,8-dihydro-5H-pyrido[4,3-d]pyrimidin-2-yl]thiazole(67 mg) as light yellow solid and 4-[6-[6-fluoro-4-(4-methylsulfonylpiperazin-1-yl)-2-pyridyl]-5-methyl-7,8-dihydro-5H-pyrido[4,3-d]pyrimidin-2-yl]thiazole(59 mg) as light yellow solid and 4-[6-[4-fluoro-6-(4-methylsulfonylpiperazin-1-yl)-2-pyridyl]-5-methyl-7,8-dihydro-5H-pyrido[4,3-d]pyrimidin-2-yl]thiazole (16 mg) as light yellow solid.

Example 20: 4-[6-[2-fluoro-6-(4-methylsulfonylpiperazin-1-yl)-4-pyridyl]-5-methyl-7,8-dihydro-5H-pyrido[4,3-d]pyrimidin-2-yl]thiazole, $^1$H NMR (400 MHz, DMSO-d$_6$) δ ppm: 9.21 (d, 1H), 8.74 (s, 1H), 8.51 (d, 1H), 6.14 (s, 1H), 6.03 (s, 1H), 5.43-5.33 (m, 1H), 4.19-4.08 (m, 1H), 3.64-3.54 (m, 4H), 3.54-3.43 (m, 1H), 3.21-3.13 (m, 4H), 3.11-2.94 (m, 2H), 2.90 (s, 3H), 1.47 (d, 3H). MS obsd. (ESI$^+$) [(M+H)$^+$]: 490.

Example 21: 4-[6-[6-fluoro-4-(4-methylsulfonylpiperazin-1-yl)-2-pyridyl]-5-methyl-7,8-dihydro-5H-pyrido[4,3-d]pyrimidin-2-yl]thiazole, $^1$H NMR (400 MHz, DMSO-d$_6$) δ ppm: 9.21 (d, 1H), 8.80 (s, 1H), 8.50 (d, 1H), 6.16 (s, 1H), 5.94 (s, 1H), 5.69-5.60 (m, 1H), 4.50-4.40 (m, 1H), 3.57-3.48 (m, 4H), 3.45-3.38 (m, 1H), 3.24-3.17 (m, 4H), 3.07-2.95 (m, 2H), 2.92 (s, 3H), 1.46 (d, 3H). MS obsd. (ESI$^+$) [(M+H)$^+$]: 490.

Example 22: 4-[6-[4-fluoro-6-(4-methylsulfonylpiperazin-1-yl)-2-pyridyl]-5-methyl-7,8-dihydro-5H-pyrido[4,3-d]pyrimidin-2-yl]thiazole, $^1$H NMR (400 MHz, DMSO-d$_6$) δ ppm: 9.20 (d, 1H), 8.78 (s, 1H), 8.50 (d, 1H), 6.16-6.07 (m, 1H), 6.04-5.97 (m, 1H), 5.68-5.58 (m, 1H), 4.52-4.42 (m, 1H), 3.66-3.58 (m, 4H), 3.45-3.36 (m, 1H), 3.21-3.15 (m, 4H), 3.05-2.94 (m, 2H), 2.90 (s, 3H), 1.47 (d, 3H). MS obsd. (ESI$^+$) [(M+H)$^+$]: 490.

Example 23, 24 and 25

4-[6-[2-Fluoro-6-(3-methoxypyrrolidin-1-yl)-4-pyridyl]-5-methyl-7,8-dihydro-5H-pyrido[4,3-d]pyrimidin-2-yl]thiazole and 4-[6-[6-fluoro-4-(3-methoxypyrrolidin-1-yl)-2-pyridyl]-5-methyl-7,8-dihydro-5H-pyrido[4,3-d]pyrimidin-2-yl]thiazole and 4-[6-[4-fluoro-6-(3-methoxypyrrolidin-1-yl)-2-pyridyl]-5-methyl-7,8-dihydro-5H-pyrido[4,3-d]pyrimidin-2-yl]thiazole Example 23

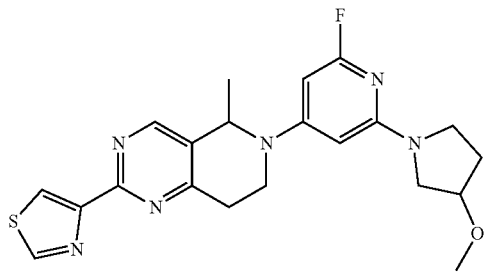

Example 24

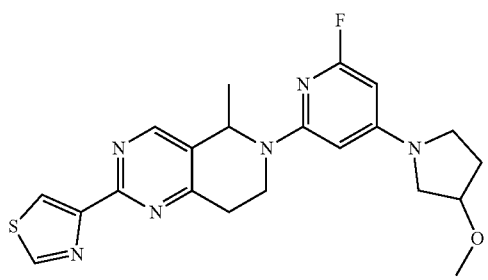

Example 25

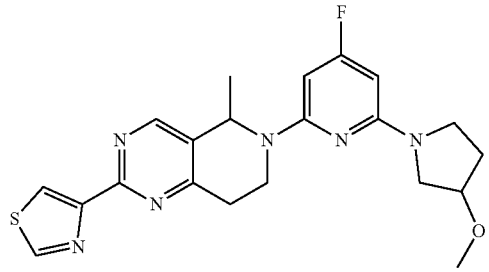

To a solution of 4-(5-methyl-5,6,7,8-tetrahydropyrido[4,3-d]pyrimidin-2-yl)thiazole (the product of step 10 in Example 11, 200 mg, 861 µmol) in DMSO (2 mL) was added DIPEA (3 mL) and 2,4,6-trifluoropyridine (149 mg, 1.12 mmol). The mixture was stirred for 2 hrs at 150° C. under microwave irradiation and cooled to rt. Then to the resulting mixture was added 3-methoxypyrrolidine hydrochloride (237 mg, 1.72 mmol). After being stirred for another 18 hrs at 130° C., the reaction mixture was then cooled to rt and concentrated in vacuo. The residue was purified by prep-HPLC to give 4-[6-[2-fluoro-6-(3-methoxypyrrolidin-1-yl)-4-pyridyl]-5-methyl-7,8-dihydro-5H-pyrido[4,3-d]pyrimidin-2-yl]thiazole (65 mg) as light yellow solid and 4-[6-[6-fluoro-4-(3-methoxypyrrolidin-1-yl)-2-pyridyl]-5-methyl-7,8-dihydro-5H-pyrido[4,3-d]pyrimidin-2-yl]thiazole (54 mg) as light yellow solid and 4-[6-[4-fluoro-6-(3-methoxypyrrolidin-1-yl)-2-pyridyl]-5-methyl-7,8-dihydro-5H-pyrido[4,3-d]pyrimidin-2-yl]thiazole (17 mg) as light yellow solid.

Example 23: 4-[6-[2-fluoro-6-(3-methoxypyrrolidin-1-yl)-4-pyridyl]-5-methyl-7,8-dihydro-5H-pyrido[4,3-d]pyrimidin-2-yl]thiazole, $^1$H NMR (400 MHz, DMSO-d$_6$) δ ppm: 9.21 (d, 1H), 8.75 (s, 1H), 8.51 (d, 1H), 5.91 (s, 1H), 5.69 (s, 1H), 5.39-5.27 (m, 1H), 4.12-3.99 (m, 2H), 3.53-3.40 (m, 4H), 3.26 (d, 3H), 3.11-2.92 (m, 2H), 2.06-1.99 (m, 2H), 1.47 (dd, 3H). MS obsd. (ESI$^+$) [(M+H)$^+$]: 427.

Example 24: 4-[6-[6-fluoro-4-(3-methoxypyrrolidin-1-yl)-2-pyridyl]-5-methyl-7,8-dihydro-5H-pyrido[4,3-d]pyrimidin-2-yl]thiazole, $^1$H NMR (400 MHz, DMSO-d$_6$) δ ppm: 9.21 (d, 1H), 8.80 (s, 1H), 8.50 (d, 1H), 5.73 (s, 1H), 5.65-5.57 (m, 1H), 5.53 (s, 1H), 4.47-4.36 (m, 1H), 4.13-4.03 (m, 1H), 3.48-3.34 (m, 4H), 3.27 (d, 3H), 3.10-2.88 (m, 2H), 2.09-2.02 (m, 2H), 1.45 (dd, 3H). MS obsd. (ESI$^+$) [(M+H)$^+$]: 427.

Example 25: 4-[6-[4-fluoro-6-(3-methoxypyrrolidin-1-yl)-2-pyridyl]-5-methyl-7,8-dihydro-5H-pyrido[4,3-d]pyrimidin-2-yl]thiazole, $^1$H NMR (400 MHz, DMSO-d$_6$) δ ppm: 9.20 (d, 1H), 8.78 (s, 1H), 8.50 (d, 1H), 6.01-5.94 (m, 1H), 5.71-5.61 (m, 1H), 5.58-5.51 (m, 1H), 4.51-4.42 (m, 1H), 4.08-4.00 (m, 1H), 3.51-3.35 (m, 4H), 3.26 (d, 3H), 3.06-2.88 (m, 2H), 2.07-1.97 (m, 2H), 1.47 (d, 3H). MS obsd. (ESI$^+$) [(M+H)$^+$]: 427.

Example 26

6-(6-Fluoro-4-methoxy-2-pyridyl)-2-(1H-imidazol-2-yl)-5-methyl-7,8-dihydro-5H-pyrido[4,3-d]pyrimidine

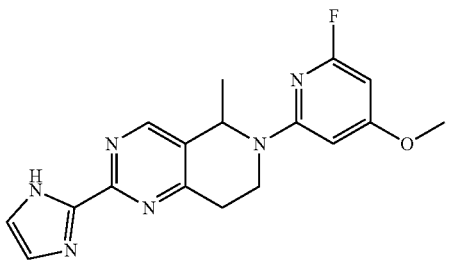 [SMILES: COc1cc(F)nc(N2CCc3nc(-c4ncc[nH]4)ncc3C2C)c1]

Step 1: preparation of 6-(6-fluoro-4-methoxy-2-pyridyl)-5-methyl-7,8-dihydro-5H-pyrido[4,3-d]pyrimidine-2-carbonitrile

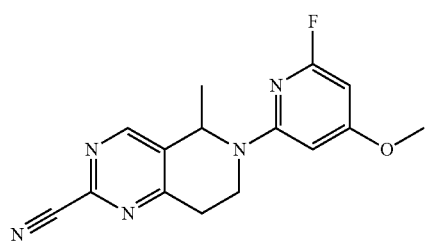 [SMILES: COc1cc(F)nc(N2CCc3nc(C#N)ncc3C2C)c1]

A mixture of 2-chloro-6-(6-fluoro-4-methoxy-2-pyridyl)-5-methyl-7,8-dihydro-5H-pyrido[4,3-d]pyrimidine (the product of step 7 in Example 4, 200 mg, 0.65 mmol), Zn(CN)$_2$ (380 mg, 3.24 mmol), Xphos (62 mg, 0.13 mmol) and allylpalladium(II) chloride dimer (24 mg, 0.06 mmol, CAS registry NO: 12012-95-2) in DMA (4 mL) was heated at 150° C. in microwave reactor for 1 hr. After being cooled to rt, the reaction mixture was diluted with H$_2$O (10 mL) and extracted with EA (20 mL) for three times. The combined organic phase was washed with brine (10 mL), dried over anhydrous Na$_2$SO$_4$ and concentrated in vacuo to give 6-(6-fluoro-4-methoxy-2-pyridyl)-5-methyl-7,8-dihydro-5H-pyrido[4,3-d]pyrimidine-2-carbonitrile (190 mg), which was used directly in the next step.

Step 2: preparation of 6-(6-fluoro-4-methoxy-2-pyridyl)-2-(1H-imidazol-2-yl)-5-methyl-7,8-dihydro-5H-pyrido[4,3-d]pyrimidine

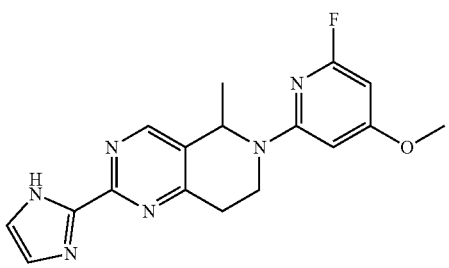 [SMILES: COc1cc(F)nc(N2CCc3nc(-c4ncc[nH]4)ncc3C2C)c1]

To a stirred solution of NaOMe (3 mg, 0.06 mmol) in MeOH (2 mL) was added a solution of 6-(6-fluoro-4-methoxy-2-pyridyl)-5-methyl-7,8-dihydro-5H-pyrido[4,3-d]pyrimidine-2-carbonitrile (190 mg, 0.63 mmol) in MeOH (2 mL) slowly at rt, and the mixture was stirred for 1 hr. To the resulting solution was then added AcOH (0.2 mL) and 2,2-dimethoxyethanamine (133 mg, 1.27 mmol). After being stirred at rt for another 1 hr, the resulting mixture was acidified with concentrated hydrochloric acid to pH=1 and then heated at 70° C. with stifling under nitrogen for 14 hrs. After being cooled to rt, the resulting reaction mixture was diluted with H$_2$O (10 mL) and extracted with EA (20 mL) for three times. The combined organic phase was washed with brine (10 mL), dried over anhydrous Na$_2$SO$_4$ and concentrated in vacuo. The residue was purified by prep-HPLC to afford 6-(6-fluoro-4-methoxy-2-pyridyl)-2-(1H-imidazol-2-yl)-5-methyl-7,8-dihydro-5H-pyrido[4,3-d]pyrimidine (26.5 mg) as a white solid. $^1$H NMR (400 MHz, Methanol-d$_4$) δ ppm: 8.71 (br s, 1 H), 7.28 (br s, 2 H), 6.22 (s, 1 H), 5.87 (s, 1 H), 5.54-5.74 (m, 1 H), 4.48 (br d, 1 H), 3.86 (s, 3 H), 3.47 (br t, 1 H), 2.95-3.18 (m, 2 H), 1.54 (br d, 3 H). MS obsd. (ESI$^+$) [(M+H)$^+$]: 341.

Example 27

6-(6-Fluoro-4-methoxy-2-pyridyl)-5-methyl-2-(1H-pyrazol-3-yl)-7,8-dihydro-5H-pyrido[4,3-d]pyrimidine

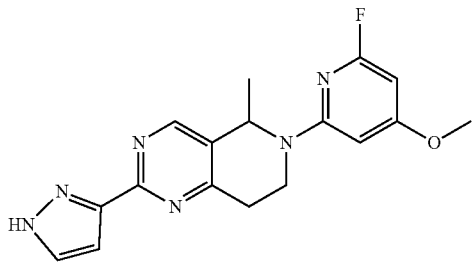 [SMILES: COc1cc(F)nc(N2CCc3nc(-c4cc[nH]n4)ncc3C2C)c1]

A mixture of 2-chloro-6-(6-fluoro-4-methoxy-2-pyridyl)-5-methyl-7,8-dihydro-5H-pyrido[4,3-d]pyrimidine (the product of step 7 in Example 4, 100 mg, 0.32 mmol), 3-(4,4,5,5-tetramethyl-1,3,2-dioxaborolan-2-yl)-1H-pyrazole (126 mg, 0.65 mmol), K$_2$CO$_3$ (134 mg, 0.97 mmol) and Pd(dppf)Cl$_2$ (71 mg, 0.10 mmol) in 1,4-dioxane and H$_2$O (3 mL/0.3 mL) was heated at 120° C. with stirring in microwave reactor for 2 hrs. After being cooled to rt, the reaction mixture was concentrated in vacuo and the residue was purified by prep-HPLC to give 6-(6-fluoro-4-methoxy-2-pyridyl)-5-methyl-2-(1H-pyrazol-3-yl)-7,8-dihydro-5H-pyrido[4,3-d]pyrimidine (5 mg) as a white solid. $^1$H NMR (400 MHz, Methanol-d$_4$) δ ppm: 8.69 (s, 1 H), 7.69 (br s, 1 H), 7.03 (d, 1 H), 6.22 (s, 1 H), 5.87 (d, 1 H), 5.61 (q, 1 H), 4.43-4.53 (m, 1 H), 3.86 (s, 3 H), 3.42-3.52 (m, 1 H), 2.97-3.17 (m, 2 H), 1.54 (d, 3 H). MS obsd. (ESI$^+$) [(M+H)$^+$]: 341.

Example 28, 29 and 30

4-[6-Fluoro-4-(5-methyl-2-thiazol-4-yl-7,8-dihydro-5H-pyrido[4,3-d]pyrimidin-6-yl)-2-pyridyl]piperazin-2-one and 4-[2-fluoro-6-(5-methyl-2-thiazol-4-yl-7,8-dihydro-5H-pyrido[4,3-d]pyrimidin-6-yl)-4-pyridyl]piperazin-2-one and 4-[4-fluoro-6-(5-methyl-2-thiazol-4-yl-7,8-dihydro-5H-pyrido[4,3-d]pyrimidin-6-yl)-2-pyridyl]piperazin-2-one Example 28

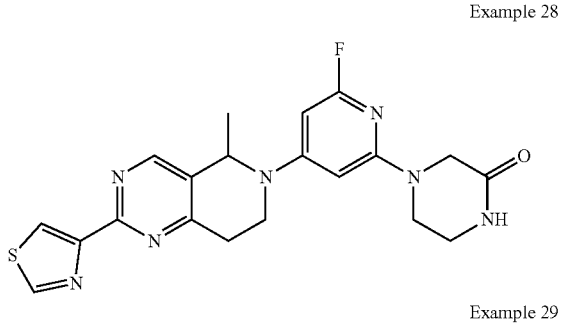

Example 29

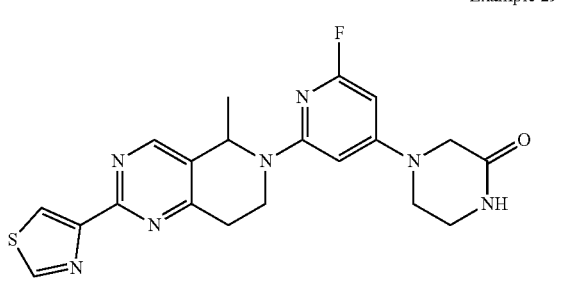

Example 30

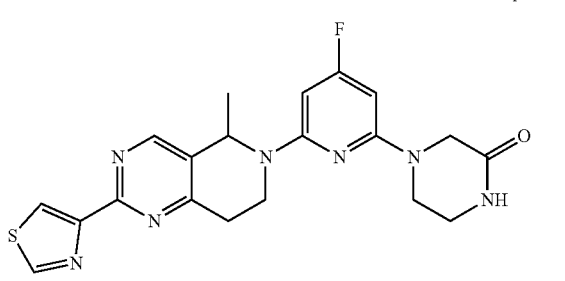

To a solution of 4-(5-methyl-5,6,7,8-tetrahydropyrido[4,3-d]pyrimidin-2-yl)thiazole (product of step 10 in Example 11, 200 mg, 861 μmol) in DMSO (2 mL) was added DIPEA (3 mL) and 2,4,6-trifluoropyridine (149 mg, 1.12 mmol). The resulting mixture was stirred for 2 hrs at 150° C. under microwave irradiation and cooled to rt. Then to the cooled mixture was added piperazin-2-one (172 mg, 1.72 mmol). After being stirred for another 18 hrs at 130° C., the resulting reaction mixture was then cooled to rt and concentrated in vacuo. The residue was purified by prep-HPLC to give 4-[6-fluoro-4-(5-methyl-2-thiazol-4-yl-7,8-dihydro-5H-pyrido[4,3-d]pyrimidin-6-yl)-2-pyridyl]piperazin-2-one (55 mg) as light yellow solid and 4-[2-fluoro-6-(5-methyl-2-thiazol-4-yl-7,8-dihydro-5H-pyrido[4,3-d]pyrimidin-6-yl)-4-pyridyl]piperazin-2-one (40 mg) as light yellow solid and 4-[4-fluoro-6-(5-methyl-2-thiazol-4-yl-7,8-dihydro-5H-pyrido[4,3-d]pyrimidin-6-yl)-2-pyridyl]piperazin-2-one (15 mg) as light yellow solid.

Example 28: 4-[6-fluoro-4-(5-methyl-2-thiazol-4-yl-7,8-dihydro-5H-pyrido[4,3-d]pyrimidin-6-yl)-2-pyridyl]piperazin-2-one, $^1$H NMR (400 MHz, DMSO-$d_6$) δ ppm: 9.21 (d, 1H), 8.74 (s, 1H), 8.51 (d, 1H), 8.09 (s, 1H), 6.02 (s, 2H), 5.44-5.36(m,1H), 4.21-4.11(m, 1H), 3.96 (s, 2H), 3.74-3.62 (m, 2H), 3.55-3.44 (m, 1H), 3.29-3.24 (m, 2H), 3.10-2.91 (m, 2H), 1.48 (d, 3H). MS obsd. (ESI$^+$) [(M+H)$^+$]: 426.

Example 29: 4-[2-fluoro-6-(5-methyl-2-thiazol-4-yl-7,8-dihydro-5H-pyrido[4,3-d]pyrimidin-6-yl)-4-pyridyl]piperazin-2-one, $^1$H NMR (400 MHz, DMSO-$d_6$) δ ppm: 9.20 (d, 1H), 8.79 (s, 1H), 8.50 (d, 1H), 8.18 (s, 1H), 6.04 (s, 1H), 5.87 (s, 1H), 5.69-5.61(m, 1H), 4.54-4.44 (m, 1H), 3.91 (s, 2H), 3.59-3.50 (m, 2H), 3.42-3.37 (m, 1H), 3.32-3.26 (m, 2H), 3.06-2.90 (m, 2H), 1.46 (d, 3H). MS obsd. (ESI$^+$) [(M+H)$^+$]: 426.

Example 30: 4-[4-fluoro-6-(5-methyl-2-thiazol-4-yl-7,8-dihydro-5H-pyrido[4,3-d]pyrimidin-6-yl)-2-pyridyl]piperazin-2-one, $^1$H NMR (400 MHz, DMSO-$d_6$) δ ppm: 9.20 (d, 1H), 8.79 (s, 1H), 8.50 (d, 1H), 8.08 (s, 1H), 6.15-6.07 (m, 1H), 5.97-5.90 (m, 1H), 5.67-5.57(m, 1H),4.53-4.40(m, 1H), 3.99 (s, 2H), 3.73-3.66 (m, 2H), 3.45-3.36 (m, 1H), 3.30-3.25 (m, 2H), 3.06-2.91 (m, 2H), 1.47 (d, 3H). MS obsd. (ESI$^+$) [(M+H)$^+$]: 426.

Example 31, 32 and 33

4-[6-[2-(Cyclopropylmethoxy)-6-fluoro-4-pyridyl]-5-methyl-7,8-dihydro-5H-pyrido[4,3-d]pyrimidin-2-yl]thiazole and 4-[6-[4-(cyclopropylmethoxy)-6-fluoro-2-pyridyl]-5-methyl-7,8-dihydro-5H-pyrido[4,3-d]pyrimidin-2-yl]thiazole and 4-[6-[6-(cyclopropylmethoxy)-4-fluoro-2-pyridyl]-5-methyl-7,8-dihydro-5H-pyrido[4,3-d]pyrimidin-2-yl]thiazole Example 31

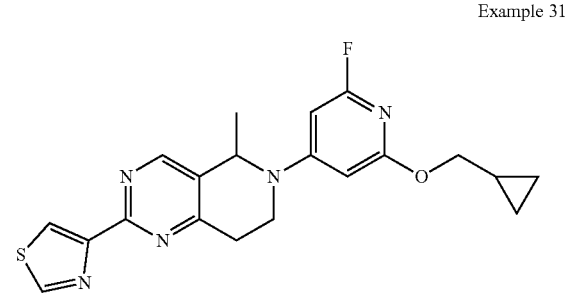

Example 32

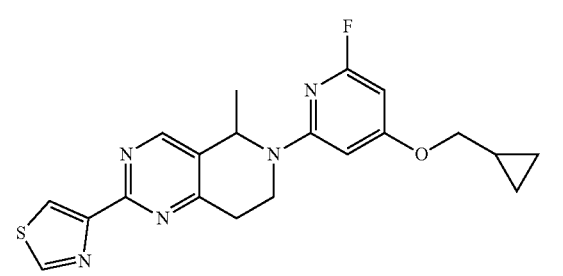

Example 33

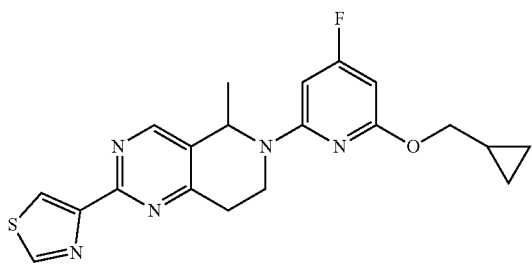

Step 1: preparation of 4-[6-(2,6-difluoro-4-pyridyl)-5-methyl-7,8-dihydro-5H-pyrido[4,3-d]pyrimidin-2-yl]thiazole and 4-[6-(4,6-difluoro-2-pyridyl)-5-methyl-7,8-dihydro-5H-pyrido[4,3-d]pyrimidin-2-yl]thiazole

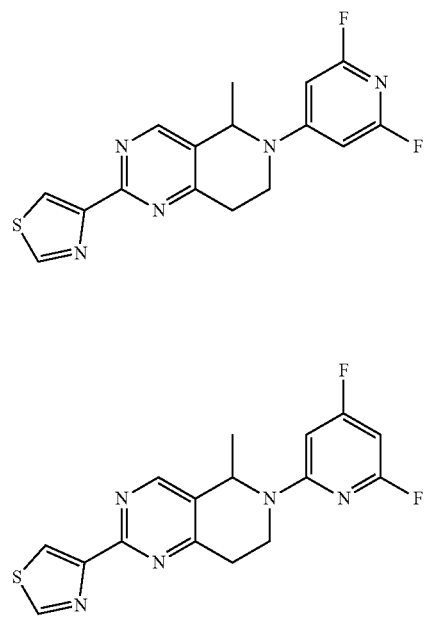

To a solution of 4-(5-methyl-5,6,7,8-tetrahydropyrido[4,3-d]pyrimidin-2-yl)thiazole (the product of step 10 in Example 11, 900 mg, 3.87 mmol) in DMSO (10 mL) was added DIPEA (15 mL) and 2,4,6-trifluoropyridine (670 mg, 5.04 mmol). After being stirred for 18 hrs at 130° C., the resulting reaction mixture was cooled to rt, then diluted with brine (20 mL) and extracted in DCM (20 mL) for three times. The combined organic layer was dried over anhydrous Na$_2$SO$_4$ and concentrated in vacuo. The residue was purified by column chromatography (eluting with DCM/MeOH=20/1, v:v) to give a mixture of 4-[6-(2,6-difluoro-4-pyridyl)-5-methyl-7,8-dihydro-5H-pyrido[4,3-d]pyrimidin-2-yl]thiazole and 4-[6-(4,6-difluoro-2-pyridyl)-5-methyl-7,8-dihydro-5H-pyrido[4,3-d]pyrimidin-2-yl]thiazole (0.9 g) as yellow solid.

Step 2: preparation of 4-[6-[2-(cyclopropylmethoxy)-6-fluoro-4-pyridyl]-5-methyl-7,8-dihydro-5H-pyrido[4,3-d]pyrimidin-2-yl]thiazole and 4-[6-[4-(cyclopropylmethoxy)-6-fluoro-2-pyridyl]-5-methyl-7,8-dihydro-5H-pyrido[4,3-d]pyrimidin-2-yl]thiazole and 4-[6-[6-(cyclopropylmethoxy)-4-fluoro-2-pyridyl]-5-methyl-7,8-dihydro-5H-pyrido[4,3-d]pyrimidin-2-yl]thiazole Example 31

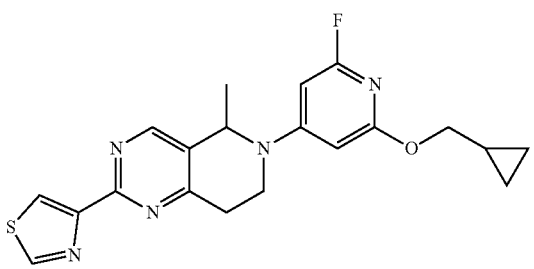

Example 32

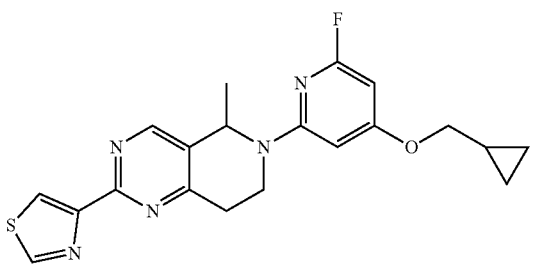

Examle 33

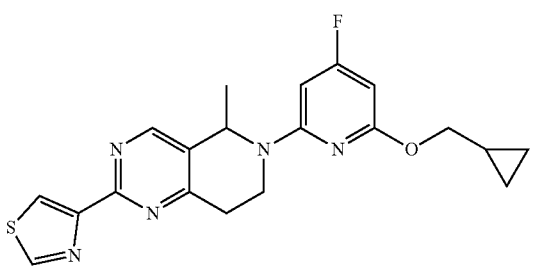

To a solution of cyclopropylmethanol (92.9 mg, 1.29 mmol) in DMF (3 mL) was added sodium hydride (68.8 mg, 60 wt. %, 1.72 mmol) at 0° C. and the mixture was stirred for 1 hr at 0° C. Then to the resulting mixture was added a mixture of 4-[6-(2,6-difluoro-4-pyridyl)-5-methyl-7,8-dihydro-5H-pyrido[4,3-d]pyrimidin-2-yl]thiazole and 4-[6-(4,6-difluoro-2-pyridyl)-5-methyl-7,8-dihydro-5H-pyrido[4,3-d]pyrimidin-2-yl]thiazole (320 mg). After being slowly warmed to 80° C. and stirred for 16 hrs at 80° C., the resulting reaction mixture was cooled to rt, then diluted with water (10 mL) and extracted in DCM (20 mL) for three times. The combined organic layer was concentrated in vacuo and the residue was purified by prep-HPLC to give 4-[6-[2-(cyclopropylmethoxy)-6-fluoro-4-pyridyl]-5-methyl-7,8-dihydro-5H-pyrido[4,3-d]pyrimidin-2-yl]thiazole (14 mg) as light yellow solid and 4-[6-[4-(cyclopropylmethoxy)-6-fluoro-2-pyridyl]-5-methyl-7,8-dihydro-5H-pyrido[4,3-d]pyrimidin-2-yl]thiazole (20 mg) as light yellow solid and 4-[6-[6-(cyclopropylmethoxy)-4-fluoro-2-pyridyl]-5-methyl-7,8-dihydro-5H-pyrido[4,3-d]pyrimidin-2-yl]thiazole (6 mg) as light yellow solid.

Example 31: 4-[6-[2-(cyclopropylmethoxy)-6-fluoro-4-pyridyl]-5-methyl-7,8-dihydro-5H-pyrido[4,3-d]pyrimidin-2-yl]thiazole, ¹H NMR (400 MHz, Methanol-d₄) δ ppm: 9.02 (d, 1H), 8.62 (s, 1H), 8.40 (d, 1H), 6.10 (t, 1H), 6.06 (d, 1H), 5.20-5.12 (m, 1H), 4.02-3.95 (m, 1H), 3.91 (d, 2H), 3.53-3.44 (m, 1H), 3.09-2.94 (m, 2H), 1.46 (d, 3H), 1.20-1.08 (m, 1H), 0.51-0.45 (m, 2H), 0.25-0.20 (m, 2H). MS obsd. (ESI⁺) [(M+H)⁺]: 398.

Example 32: 4-[6-[4-(cyclopropylmethoxy)-6-fluoro-2-pyridyl]-5-methyl-7,8-dihydro-5H-pyrido[4,3-d]pyrimidin-2-yl]thiazole, ¹H NMR (400 MHz, Methanol-d₄) δ ppm: 9.02 (d, 1H), 8.61 (s, 1H), 8.38 (d, 1H), 6.10 (s, 1H), 5.74 (d, 1H), 5.55-5.48 (m, 1H), 4.41-4.34 (m, 1H), 3.80 (d, 2H), 3.42-3.32 (m, 1H), 3.05-2.92 (m, 2H), 1.44 (d, 3H), 1.22-1.13 (m, 1H), 0.58-0.48 (m, 2H), 0.30-0.22 (m, 2H). MS obsd. (ESI⁺) [(M+H)⁺]: 398.

Example 33: 4-[6-[6-(cyclopropylmethoxy)-4-fluoro-2-pyridyl]-5-methyl-7,8-dihydro-5H-pyrido[4,3-d]pyrimidin-2-yl]thiazole, ¹H NMR (400 MHz, Methanol-d₄) δ ppm: 9.02 (d, 1H), 8.63 (s, 1H), 8.38 (d, 1H), 6.11-6.05(m, 1H), 5.72-5.66 (m, 1H), 5.57-5.50 (m, 1H), 4.46-4.34 (m, 1H), 4.09-3.97 (m, 2H), 3.44-3.34 (m, 1H), 3.06-2.90 (m, 2H), 1.46 (d, 3H), 1.22-1.15 (m, 1H), 0.54-0.44 (m, 2H), 0.30-0.21 (m, 2H). MS obsd. (ESI⁺) [(M+H)⁺]: 398.

Example 34, 35 and 36

4-[6-[2-(2,2-Difluoroethoxy)-6-fluoro-4-pyridyl]-5-methyl-7,8-dihydro-5H-pyrido[4,3-d]pyrimidin-2-yl]thiazole and 4-[6-[4-(2,2-difluoroethoxy)-6-fluoro-2-pyridyl]-5-methyl-7,8-dihydro-5H-pyrido[4,3-d]pyrimidin-2-yl]thiazole and 4-[6-[6-(2,2-difluoroethoxy)-4-fluoro-2-pyridyl]-5-methyl-7,8-dihydro-5H-pyrido[4,3-d]pyrimidin-2-yl]thiazole Example 34

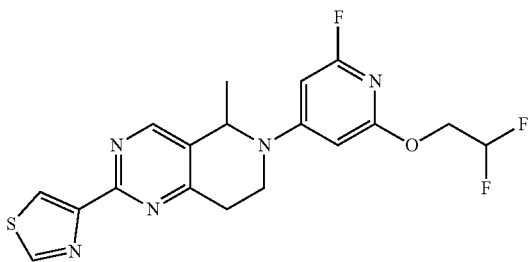

Example 35

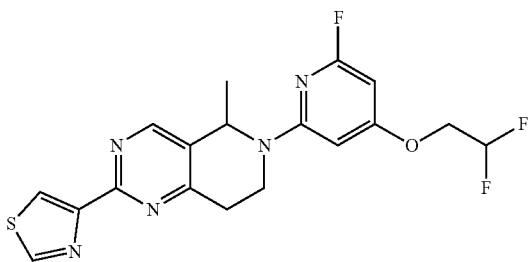

Example 36

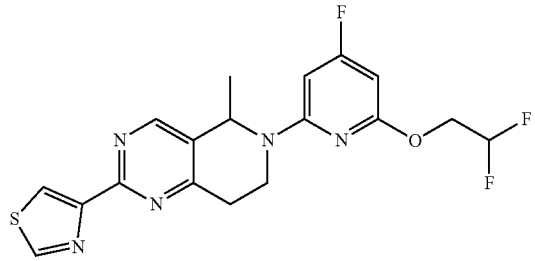

To a solution of 2,2-difluoroethanol (118.7 mg, 1.45 mmol) in DMF (3 mL) was added sodium hydride (57.9 mg, 60 wt. %, 1.45 mmol) at 0° C. and the mixture was stirred for 1 hr at 0° C. Then to the resulting mixture was added a mixture of 4-[6-(2,6-difluoro-4-pyridyl)-5-methyl-7,8-dihydro-5H-pyrido[4,3-d]pyrimidin-2-yl]thiazole and 4-[6-(4,6-difluoro-2-pyridyl)-5-methyl-7,8-dihydro-5H-pyrido[4,3-d]pyrimidin-2-yl]thiazole (250 mg, the product of step 1 in Example 31, 32 and 33). After being slowly warmed to 80° C. and stirred for 16 hrs, the resulting mixture was cooled to rt, then diluted with water (10 mL) and extracted in DCM (20 mL) for three times. The combined organic layer was concentrated in vacuo and the residue was purified by prep-HPLC to give 4-[6-[2-(2,2-difluoroethoxy)-6-fluoro-4-pyridyl]-5-methyl-7,8-dihydro-5H-pyrido[4,3-d]pyrimidin-2-yl]thiazole (44 mg) as light yellow solid and 4-[6-[4-(2,2-difluoroethoxy)-6-fluoro-2-pyridyl]-5-methyl-7,8-dihydro-5H-pyrido[4,3-d]pyrimidin-2-yl]thiazole(27 mg) as light yellow solid and 4-[6-[6-(2,2-difluoroethoxy)-4-fluoro-2-pyridyl]-5-methyl-7,8-dihydro-5H-pyrido[4,3-d]pyrimidin-2-yl]thiazole (4 mg) as light yellow solid.

Example 34: 4-[6-[2-(2,2-difluoroethoxy)-6-fluoro-4-pyridyl]-5-methyl-7,8-dihydro-5H-pyrido[4,3-d]pyrimidin-2-yl]thiazole, ¹H NMR (400 MHz, Methanol-d₄) δ ppm: 9.14 (d, 1H), 8.73 (s, 1H), 8.51 (d, 1H), 6.32-6.26 (m, 2.3H), 6.16 (t, 0.5H), 6.03 (t, 0.2H), 5.32-5.23 (m, 1H), 4.50-4.36 (m, 2H), 4.15-4.06 (m, 1H), 3.66-3.55 (m, 1H), 3.23-3.05 (m, 2H), 1.58 (d, 3H). MS obsd. (ESI⁺) [(M+H)⁺]: 398.

Example 35: 4-[6-[4-(2,2-difluoroethoxy)-6-fluoro-2-pyridyl]-5-methyl-7,8-dihydro-5H-pyrido[4,3-d]pyrimidin-2-yl]thiazole, ¹H NMR (400 MHz, Methanol-d₄) δ ppm: 9.14 (d, 1H), 8.73 (s, 1H), 8.50 (d, 1H), 6.35 (t, 0.3H), 6.31 (s, 1H), 6.21 (t, 0.5H), 6.07 (t, 0.3H), 5.94 (d, 1H), 5.70-5.61(m, 1H), 4.56-4.48 (m, 1H), 4.41-4.30 (m, 2H), 3.55-3.45 (m, 1H), 3.18-3.02 (m, 2H), 1.57 (d, 3H). MS obsd. (ESI⁺) [(M+H)⁺]: 398.

Example 36: 4-[6-[6-(2,2-difluoroethoxy)-4-fluoro-2-pyridyl]-5-methyl-7,8-dihydro-5H-pyrido[4,3-d]pyrimidin-2-yl]thiazole, ¹H NMR (400 MHz, Methanol-d₄) δ ppm: 9.14 (d, 1H), 8.77 (s, 1H), 8.52 (d, 1H), 6.34 (t, 0.3H), 6.32-6.27(m, 1H), 6.20 (t, 0.5H), 6.06 (t, 0.2H), 5.93-5.88 (m, 1H), 5.70-5.62 (m, 1H), 4.63-4.48 (m, 3H), 3.60-3.48(m, 1H), 3.19-3.05 (m, 2H), 1.60 (d, 3H). MS obsd. (ESI⁺) [(M+H)⁺]: 398.

Example 37, 38 and 39

4-[6-[2-Fluoro-6-(tetrahydrofuran-3-ylmethoxy)-4-pyridyl]-5-methyl-7,8-dihydro-5H-pyrido[4,3-d]pyrimidin-2-yl]thiazole and 4-[6-[6-fluoro-4-(tetrahydrofuran-3-ylmethoxy)-2-pyridyl]-5-methyl-7,8-dihydro-5H-pyrido[4,3-d]pyrimidin-2-yl]thiazole and 4-[6-[4-fluoro-6-(tetrahydrofuran-3-ylmethoxy)-2-pyridyl]-5-methyl-7,8-dihydro-5H-pyrido[4,3-d]pyrimidin-2-yl]thiazole Example 37

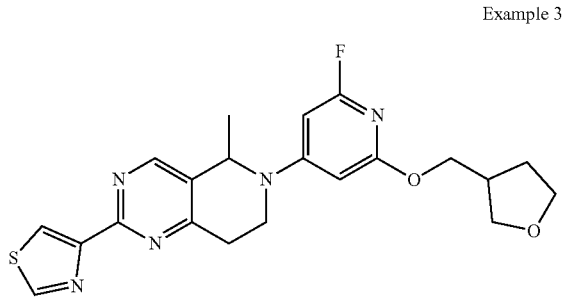

Example 38

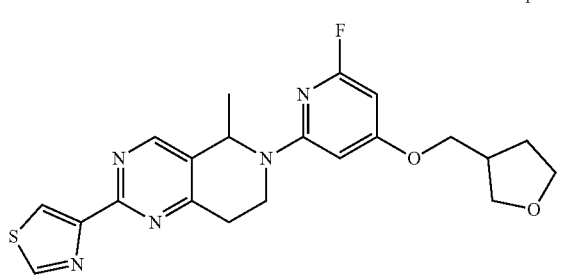

Example 39

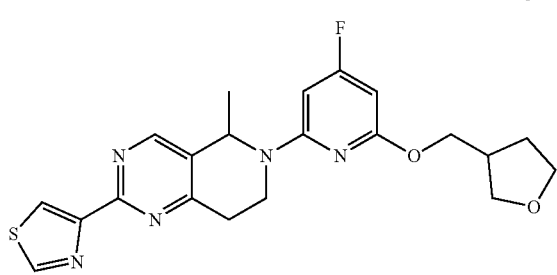

To a solution of (tetrahydrofuran-3-yl)methanol (147.6 mg, 1.45 mmol) in DMF (3 mL) was added sodium hydride (57.9 mg, 60 wt. %, 1.45 mmol) at 0° C. and the resulting mixture was stirred for 1 hr at 0° C. Then to the suspension was added a mixture of 4-[6-(2,6-difluoro-4-pyridyl)-5-methyl-7,8-dihydro-5H-pyrido[4,3-d]pyrimidin-2-yl]thiazole and 4-[6-(4,6-difluoro-2-pyridyl)-5-methyl-7,8-dihydro-5H-pyrido[4,3-d]pyrimidin-2-yl]thiazole (250 mg, the product of step 1 in Example 31, 32 and 33). After being slowly warmed to 80° C. and stirred for 16 hrs, the resulting mixture was cooled to rt, then diluted with water (10 mL) and extracted in DCM (20 mL) for three times. The combined organic layer was concentrated in vacuo and the residue was purified by prep-HPLC to give 4-[6-[2-fluoro-6-(tetrahydrofuran-3-ylmethoxy)-4-pyridyl]-5-methyl-7,8-dihydro-5H-pyrido[4,3-d]pyrimidin-2-yl]thiazole (32 mg) as light yellow solid and 4-[6-[6-fluoro-4-(tetrahydrofuran-3-ylmethoxy)-2-pyridyl]-5-methyl-7,8-dihydro-5H-pyrido[4,3-d]pyrimidin-2-yl]thiazole (34 mg) as light yellow solid and 4-[6-[4-fluoro-6-(tetrahydrofuran-3-ylmethoxy)-2-pyridyl]-5-methyl-7,8-dihydro-5H-pyrido[4,3-d]pyrimidin-2-yl]thiazole (7 mg) as light yellow solid.

Example 37: 4-[6-[2-fluoro-6-(tetrahydrofuran-3-ylmethoxy)-4-pyridyl]-5-methyl-7,8-dihydro-5H-pyrido[4,3-d]pyrimidin-2-yl]thiazole, $^1$H NMR (400 MHz, DMSO-$d_6$) δ ppm: 9.21 (d, 1H), 8.73 (s, 1H), 8.51 (d, 1H), 6.33 (s, 1H), 6.21 (s, 1H), 5.41-5.29 (m, 1H), 4.17-4.01 (m, 3H), 3.81-3.72 (m, 2H), 3.69-3.61 (m, 1H), 3.56-3.47 (m, 2H), 3.12-2.91 (m, 2H), 2.69-2.56 (m, 1H), 2.06-1.95 (m, 1H), 1.69-1.58 (m, 1H), 1.47 (d, 3H). MS obsd. (ESI$^+$) [(M+H)$^+$]: 428.

Example 38: 4-[6-[6-fluoro-4-(tetrahydrofuran-3-ylmethoxy)-2-pyridyl]-5-methyl-7,8-dihydro-5H-pyrido[4,3-d]pyrimidin-2-yl]thiazole, $^1$H NMR (400 MHz, DMSO-$d_6$) δ ppm: 9.20 (d, 1H), 8.80 (s, 1H), 8.50 (d, 1H), 6.32 (s, 1H), 5.98 (d, 1H), 5.66-5.58 (m, 1H), 4.48-4.39 (m, 1H), 4.09-3.96 (m, 2H), 3.83-3.75 (m, 2H), 3.70-3.63 (m, 1H), 3.55-3.49 (m, 1H), 3.46-3.38 (m, 1H), 3.08-2.90 (m, 2H), 2.72-2.60 (m, 1H), 2.09-1.97 (m, 1H), 1.70-1.59(m, 1H), 1.47 (d, 3H). MS obsd. (ESI$^+$) [(M+H)$^+$]: 428.

Example 39: 4-[6-[4-fluoro-6-(tetrahydrofuran-3-ylmethoxy)-2-pyridyl]-5-methyl-7,8-dihydro-5H-pyrido[4,3-d]pyrimidin-2-yl]thiazole, $^1$H NMR (400 MHz, DMSO-$d_6$) δ ppm: 9.21 (d, 1H), 8.80 (s, 1H), 8.50 (d, 1H), 6.39-6.33 (m, 1H), 5.95-5.88 (m, 1H), 5.67-5.58 (m, 1H), 4.52-4.44 (m, 1H), 4.29-4.14 (m, 2H), 3.82-3.75 (m, 2H), 3.70-3.61 (m, 1H), 3.56-3.49 (m, 1H), 3.48-3.40 (m, 1H), 3.07-2.93 (m, 2H), 2.70-2.59(m, 1H), 2.05-1.98 (m, 1H), 1.71-1.63 (m, 1H), 1.49 (d, 3H). MS obsd. (ESI$^+$) [(M+H)$^+$]: 428.

Example 40 and 41

1-[3-[[6-Fluoro-4-(5-methyl-2-thiazol-4-yl-7,8-dihydro-5H-pyrido[4,3-d]pyrimidin-6-yl)-2-pyridyl]oxy]propyl]pyrrolidin-2-one and 1-[3-[[2-fluoro-6-(5-methyl-2-thiazol-4-yl-7,8-dihydro-5H-pyrido[4,3-d]pyrimidin-6-yl)-4-pyridyl]oxy]propyl]pyrrolidin-2-one Example 40

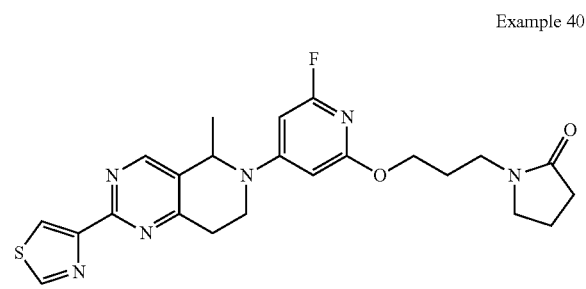

Example 41

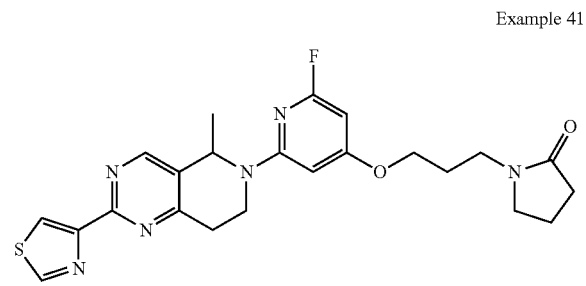

To a solution of 1-(3-hydroxypropyl)pyrrolidin-2-one (207.3 mg,1.45 mmol) in DMF (3 mL) was added sodium hydride (57.9 mg, 60 wt. %, 1.45 mmol) at 0° C. and the resulting mixture was stirred for 1 hr at 0° C. Then to the suspension was added a mixture of 4-[6-(2,6-difluoro-4-pyridyl)-5-methyl-7,8-dihydro-5H-pyrido[4,3-d]pyrimidin-2-yl]thiazole and 4-[6-(4,6-difluoro-2-pyridyl)-5-methyl-7,8-dihydro-5H-pyrido[4,3-d]pyrimidin-2-yl]thiazole (250 mg, the product of step 1 in Example 31, 32 and 33). The resulting mixture was slowly warmed to 80° C. and stirred for 16 hrs. After being cooled to rt, the resulting reaction mixture was diluted with water (10 mL) and extracted in DCM (20 mL) for three times. The combined organic layer was concentrated in vacuo and the residue was purified by prep-HPLC to give 1-[3-[[6-fluoro-4-(5-methyl-2-thiazol-4-yl-7,8-dihydro-5H-pyrido[4,3-d]pyrimidin-6-yl)-2-pyridyl]oxy]propyl]pyrrolidin-2-one (3 mg) as light yellow solid and 1-[3-[[2-fluoro-6-(5-methyl-2-thiazol-4-yl-7,8-dihydro-5H-pyrido[4,3-d]pyrimidin-6-yl)-4-pyridyl]oxy]propyl]pyrrolidin-2-one (5 mg) as light yellow solid.

Example 40: 1-[3-[[6-fluoro-4-(5-methyl-2-thiazol-4-yl-7,8-dihydro-5H-pyrido[4,3-d]pyrimidin-6-yl)-2-pyridyl]oxy]propyl]pyrrolidin-2-one, $^1$H NMR (400 MHz, Methanol-$d_4$) δ ppm: 9.03 (d, 1H), 8.63 (s, 1H), 8.41 (d, 1H), 6.12 (s, 1H), 6.08 (s, 1H), 5.20-5.14 (m, 1H), 4.10 (t, 2H), 4.04-3.97 (m, 1H), 3.54-3.33 (m, 5H), 3.08-2.95 (m, 2H), 2.28 (t, 2H), 1.99-1.85 (m, 4H), 1.47 (d, 3H). MS obsd. (ESI$^+$) [(M+H)$^+$]: 469.

Example 41: 1-[3-[[2-fluoro-6-(5-methyl-2-thiazol-4-yl-7,8-dihydro-5H-pyrido[4,3-d]pyrimidin-6-yl)-4-pyridyl]oxy]propyl]pyrrolidin-2-one, $^1$H NMR (400 MHz, Methanol-$d_4$) δ ppm: 9.02 (d, 1H), 8.62 (s, 1H), 8.39 (d, 1H), 6.12 (s, 1H), 5.77 (d, 1H), 5.57-5.48 (m, 1H), 4.42-4.35 (m, 1H), 3.99 (t, 2H), 3.45-3.34 (m, 5H), 3.06-2.92 (m, 2H), 2.27 (t, 2H), 2.01-1.87 (m, 4H), 1.45 (d, 3H). MS obsd. (ESI$^+$) [(M+H)$^+$]: 469.

Example 42

4-[6-(6-Fluoro-4-methoxy-2-pyridyl)-5-methyl-7,8-dihydro-5H-pyrido[4,3-d]pyrimidin-2-yl]-5-methyl-thiazole

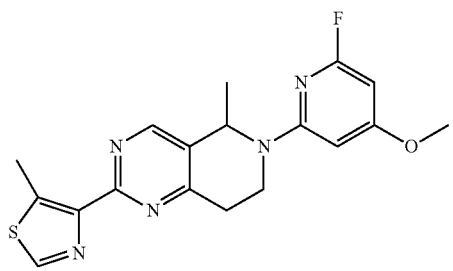 [SMILES: COc1cc(F)nc(N2CCc3nc(-c4ncsc4C)ncc3C2C)c1]

Step 1: preparation of tert-butyl-dimethyl-(5-methylthiazol-2-yl)silane

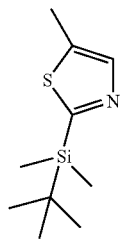

To a stirred solution of 2-bromo-5-methylthiazole (1.00 g, 5.62 mmol) in THF (20 mL) was added n-butyllithium solution (2.7 mL, 6.74 mmol, hexane solution) slowly at −70° C. and the mixture was stirred for 0.5 hr at −70° C. Then to the resulting mixture was added tert-butyldimethylchlorosilane (1.02 g, 6.74 mmol) slowly. After being warmed to 20° C. and stirred for another 2 hrs, the reaction mixture was diluted with saturated NH$_4$Cl solution and extracted with EA (30 mL) for three times. The combined organic phase was washed with brine (20 mL), then dried over anhydrous Na$_2$SO$_4$, concentrated in vacuo and purified by the flash column chromatography (eluting with PE:EA=50:1, v:v) to give tert-butyl-dimethyl-(5-methylthiazol-2-yl)silane (1.10 g) as a yellow liquid.

Step 2: preparation of tert-butyl-(4-iodo-5-methyl-thiazol-2-yl)-dimethyl-silane

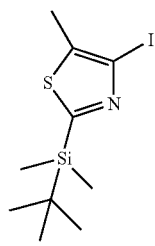

To a stirred solution of tert-butyl-dimethyl-(5-methylthiazol-2-yl)silane (680 mg, 3.19 mmol) in THF (10 mL) was added n-butyllithium solution (3.2 mL, 7.97 mmol, hexane solution) at −20° C. and the mixture was stirred for 0.5 hr. Then to the resulting mixture was added a solution of iodine (1.20 g, 4.78 mmol) in THF (5 mL) at 0° C. After being warmed to 20° C. and stirred for 2 hrs, the resulting reaction mixture was diluted with saturated aqueous NH$_4$Cl and extracted with EA (20 mL) for three times. The combined organic phase was dried over anhydrous Na$_2$SO$_4$, concentrated in vacuo. The residue was purified by flash column chromatography (eluting with PE:EA=100:1, v:v) to afford tert-butyl-(4-iodo-5-methyl-thiazol-2-yl)-dimethyl-silane (470 mg) as a yellow liquid.

Step 3: preparation of tert-butyl-dimethyl-(5-methyl-4-tributylstannyl-thiazol-2-yl)silane

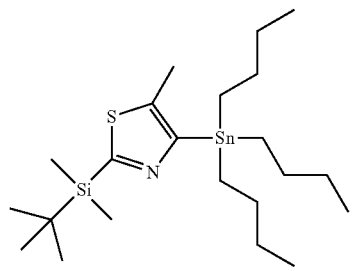 [SMILES: CCC[CH2][Sn]([CH2]CCC)([CH2]CCC)[c]1nc([Si](C)(C)C(C)(C)C)sc1C]

To a stirred solution of tert-butyl-(4-iodo-5-methyl-thiazol-2-yl)-dimethyl-silane (100 mg, 0.29 mmol) in THF (2 mL) was added ethylmagnesium bromide (0.15 mL, 0.44 mmol) at rt and the mixture was stirred for 2 hrs. Then n-Bu$_3$SnCl (530 mg, 1.63 mmol) was added slowly and the reaction was stirred at 20° C. for 16 hrs. The reaction was quenched with saturated NH$_4$Cl solution and extracted with EA (5 mL) for three times. The combined organic phase was dried over anhydrous Na$_2$SO$_4$ and concentrated in vacuo to give crude tert-butyl-dimethyl-(5-methyl-4-tributylstannyl-thiazol-2-yl)silane (110 mg) which was used directly in the next step.

Step 4: preparation of 4-[6-(6-fluoro-4-methoxy-2-pyridyl)-5-methyl-7,8-dihydro-5H-pyrido[4,3-d]pyrimidin-2-yl]-5-methyl-thiazole

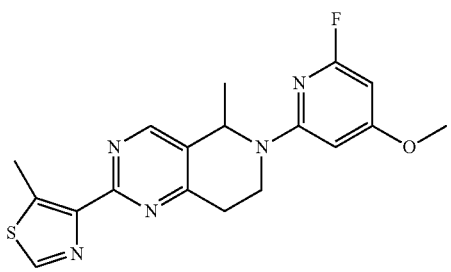 [SMILES: COc1cc(F)nc(N2CCc3nc(-c4ncsc4C)ncc3C2C)c1]

A mixture of 2-chloro-6-(6-fluoro-4-methoxy-2-pyridyl)-5-methyl-7,8-dihydro-5H-pyrido[4,3-d]pyrimidine (100 mg, 0.32 mmol, the product of step 7 in Example 4), tert-butyl-dimethyl-(5-methyl-4-tributylstannyl-thiazol-2-yl)silane (488 mg, 0.97 mmol) and Xphos-pd-G2 (25 mg, 0.03 mmol, CAS registry NO: 1310584-14-5) in 1,4-dioxane (5 mL) was heated with stirring under nitrogen at 120° C. for 12 hrs. The resulting reaction mixture was cooled to rt and concentrated in vacuo. The residue was purified by prep-HPLC to afford 4-[6-(6-fluoro-4-methoxy-2-pyridyl)-5-methyl-7,8-dihydro-5H-pyrido[4,3-d]pyrimidin-2-yl]-5-methyl-thiazole (8.6 mg, yield: 7%) as a white solid. $^1$H NMR (400 MHz, Methanol-d$_4$) δ ppm: 8.85 (s, 1H), 8.74 (s, 1 H), 6.22 (s, 1 H), 5.86 (s, 1 H), 5.63 (br d, 1 H), 4.42-4.54 (m, 1 H), 3.86 (s, 3 H), 3.43-3.54 (m, 1 H), 2.98-3.20 (m, 2 H), 2.89 (s, 3 H), 1.55 (d, 3 H). MS obsd. (ESI$^+$) [(M+H)$^+$]: 372.

Example 43

6-(6-Fluoro-4-methoxy-2-pyridyl)-5-methyl-2-(1H-1,2,4-triazol-5-yl)-7,8-dihydro-5H-pyrido[4,3-d]pyrimidine

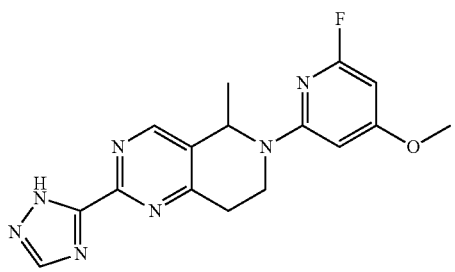 [SMILES: COc1cc(F)nc(N2CCc3nc(-c4ncn[nH]4)ncc3C2C)c1]

Step 1: preparation of N-amino-6-(6-fluoro-4-methoxy-2-pyridyl)-5-methyl-7,8-dihydro-5H-pyrido[4,3-d]pyrimidine-2-carboxamidine

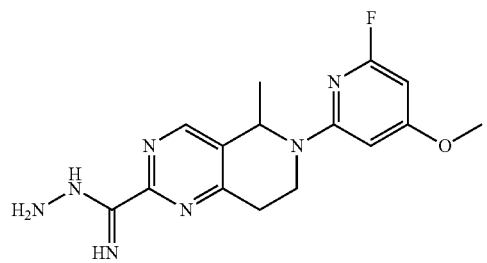 [SMILES: COc1cc(F)nc(N2CCc3nc(C(=N)NN)ncc3C2C)c1]

A mixture of 6-(6-fluoro-4-methoxy-2-pyridyl)-5-methyl-7,8-dihydro-5H-pyrido[4,3-d]pyrimidine-2-carbonitrile (the product of step 1 in Example 26, 50 mg, 0.17 mmol) and NH$_2$NH$_2$ hydrate (13 mg, 0.25 mmol) in EtOH (1 mL) was heated with stirring at 80° C. for 3 hrs. The resulting mixture was concentrated in vacuo to give crude N-amino-6-(6-fluoro-4-methoxy-2-pyridyl)-5-methyl-7,8-dihydro-5H-pyrido[4,3-d]pyrimidine-2-carboxamidine (50 mg) as a yellow solid, which was used directly in the next step.

Step 2: preparation of 6-(6-fluoro-4-methoxy-2-pyridyl)-5-methyl-2-(1H-1,2,4-triazol-5-yl)-7,8-dihydro-5H-pyrido[4,3-d]pyrimidine

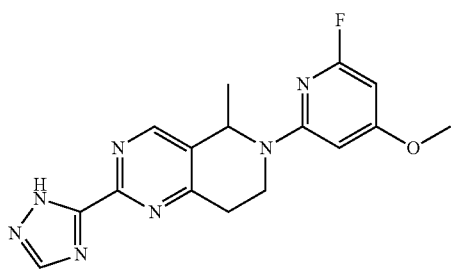 [SMILES: COc1cc(F)nc(N2CCc3nc(-c4ncn[nH]4)ncc3C2C)c1]

A mixture of crude N-amino-6-(6-fluoro-4-methoxy-2-pyridyl)-5-methyl-7,8-dihydro-5H-pyrido[4,3-d]pyrimidine-2-carboxamidine (50 mg, 0.15 mmol), triethyl orthoformate (112 mg, 0.75 mmol) in AcOH (0.5 mL) was heated with stirring at 100° C. for 1 hr. The resulting mixture was diluted with EA (100 mL), washed with aqueous $NaHCO_3$ (30 mL) and brine (30 mL), dried over $Na_2SO_4$ and concentrated in vacuo. The residue was purified by prep-HPLC to give 6-(6-fluoro-4-methoxy-2-pyridyl)-5-methyl-2-(1H-1,2,4-triazol-5-yl)-7,8-dihydro-5H-pyrido[4,3-d]pyrimidine (11.8 mg) as a white solid. $^1$H NMR (400 MHz, $CDCl_3$) δ ppm: 8.69 (s, 1 H) 8.25 (s, 1 H) 6.00 (s, 1 H) 5.83 (d, 1 H) 5.66 (q, 1 H) 4.30-4.42 (m, 1 H) 3.86 (s, 3 H) 3.40-3.54 (m, 1 H) 3.07-3.28 (m, 2 H) 1.57 (d, 3 H). MS obsd. ($ESI^+$) [$(M+H)^+$]: 342.

BIOLOGICAL EXAMPLES

Example 44 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 µL/well culture supernatant was used and HBsAg was quantified using HBsAg chemiluminescence immunoassay (CLIA) kit (Autobio Diagnostics Co., Zhengzhou, China, Catalog number: CL0310-2), 50 µL of the supernatant was transferred to the CLIA assay plate and 50 µL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration at which HBsAg secretion was reduced by 50% compared to the no drug control.

The compounds according to formula I were tested for their capacity to inhibit HBsAg as described herein. The Examples were tested in the above assay and found to have $IC_{50}$ below 50 µM. Particular compounds of formula I were found to have $IC_{50}$ below 0.50 µM. More Particular compounds of formula I were found to have $IC_{50}$ below 0.100 µM. Results of HBsAg assay are given in Table 1.

TABLE 1

Activity data in HBsAg assay

| Example No. | $IC_{50}$ (µM) |
|---|---|
| 1 | 1.155 |
| 2 | 22.882 |
| 3 | 0.666 |
| 4 | 0.316 |
| 5 | 0.023 |
| 6 | 0.118 |
| 7 | 16.685 |
| 8 | 0.029 |
| 9 | 0.095 |
| 10 | 0.421 |
| 11 | 0.026 |
| 12 | 0.036 |
| 13 | 0.033 |
| 14 | 0.074 |
| 15 | 1.522 |
| 16 | 25.751 |
| 17 | 0.017 |
| 18 | 0.016 |
| 19 | 0.175 |
| 20 | 0.013 |
| 21 | 0.016 |
| 22 | 0.066 |
| 23 | 0.035 |
| 24 | 0.023 |
| 25 | 0.06 |
| 26 | 0.031 |
| 27 | 0.23 |
| 28 | 0.042 |
| 29 | 0.034 |
| 30 | 0.021 |
| 31 | 0.117 |
| 32 | 0.039 |
| 33 | 0.212 |
| 34 | 0.14 |
| 35 | 0.039 |
| 36 | 0.112 |
| 37 | 0.07 |
| 38 | 0.02 |
| 39 | 0.139 |
| 40 | 0.222 |
| 41 | 0.102 |
| 42 | 0.282 |
| 43 | 0.008 |

HBV DNA Assay

The assay employs real-time qPCR (TaqMan) to directly measure extracellular HBV DNA copy number in the cell supernatant. HepG2.2.15 cells were plated in 96-well microtiter plates before treatment with complete medium (DMEM, Glutamax, 10% FBS, 1% Penicillin/Streptomycin, 250 µg/mL Genetycin, final DMSO concentration is 1%). Only the interior wells were utilized to reduce "edge effects" observed during cell culture, the exterior wells were filled with complete medium to help minimize sample evaporation. The HepG2.2.15 cells were treated 1 h later with various concentrations of a test compound in duplicate (top concentration used at 5 µM, 2 µM or 0.5 µM according to the HBsAg IC50 observed, with 1/3 successive dilutions (total of 10 dilutions). Six days following the initial administration of the test compound, the cell culture supernatant was collected; DNA extraction was performed by automated system (Magnapure) and then used in a real-time qPCR/TaqMan assay to determine HBV DNA copy numbers. Antiviral activity was calculated from the reduction in HBV DNA levels ($IC_{50}$). The compounds of the present invention were tested for their capacity to inhibit HBV DNA as described herein. The Examples were tested in the above assay and found to have $IC_{50}$ below 50 µM. Results of HBV DNA assay are given in Table 2.

TABLE 2

| Anti HBV DNA production activity in HepG2.2.15 cells | |
|---|---|
| Example No. | IC$_{50}$ (nM) |
| 5 | 8.7 |
| 20 | 20.3 |
| 26 | 5.7 |
| 43 | 1.7 |

The invention claimed is:

1. A compound of formula I,

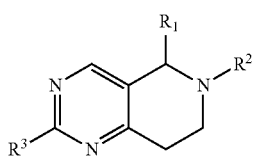

(I)

wherein:
$R^1$ is hydrogen, $C_{1-6}$alkyl, $C_{1-6}$alkoxy, halo$C_{1-6}$alkyl or $C_{3-7}$cycloalkyl;
$R^2$ is phenyl or pyridinyl, wherein said phenyl or pyridinyl is unsubstituted, or substituted by one, two or three substituents independently selected from $C_{1-6}$alkyl, cyano, $C_{3-7}$cycloalkyl$C_{1-6}$alkoxy, $C_{3-7}$cycloalkyl, halo$C_{1-6}$alkoxy, amino, $C_{1-6}$alkylamino, ($C_{1-6}$alkyl)$_2$amino, halogen, $C_{1-6}$alkoxy, $C_{1-6}$alkoxypyrrolidinyl, $C_{1-6}$alkylcarbonylpiperazinyl, $C_{1-6}$alkylsulfonylpiperazinyl, $C_{1-6}$alkoxycarbonylpiperazinyl, morpholinyl, piperazinyl, oxopiperazinyl, oxopyrrolidinyl$C_{1-6}$alkoxy, pyrrolidinyl$C_{1-6}$alkoxy, pyrrolidinyl, oxopyrrolidinyl, tetrahydrofuranyl$C_{1-6}$alkoxy and tetrahydrofuranyl; and
$R^3$ is imidazolyl, oxazolyl, pyrazolyl, thiazolyl or triazolyl, wherein said imidazolyl, oxazolyl, pyrazolyl, thiazolyl or triazolyl is unsubstituted, or substituted by $C_{1-6}$alkyl, halogen, halo$C_{1-6}$alkyl, $C_{3-7}$cycloalkyl, $C_{1-6}$alkoxy, halo$C_{1-6}$alkoxy or phenyl$C_{1-6}$alkyl;
or a pharmaceutically acceptable salt, or an enantiomer thereof.

2. A compound according to claim 1, wherein:
$R^1$ is hydrogen or $C_{1-6}$alkyl;
$R^2$ is phenyl or pyridinyl, wherein said phenyl or pyridinyl is substituted by one, two or three substituents independently selected from $C_{3-7}$cycloalkyl$C_{1-6}$alkoxy, halo$C_{1-6}$alkoxy, ($C_{1-6}$alkyl)$_2$amino, halogen, $C_{1-6}$alkoxy, $C_{1-6}$alkoxypyrrolidinyl, $C_{1-6}$alkylsulfonylpiperazinyl, morpholinyl, oxopiperazinyl, oxopyrrolidinyl$C_{1-6}$alkoxy, pyrrolidinyl and tetrahydrofuranyl$C_{1-6}$alkoxy; and
$R^3$ is imidazolyl, oxazolyl, pyrazolyl, thiazolyl or triazolyl, wherein said imidazolyl, oxazolyl, pyrazolyl, thiazolyl or triazolyl is unsubstituted or substituted by $C_{1-6}$alkyl or phenyl$C_{1-6}$alkyl;
or a pharmaceutically acceptable salt, or an enantiomer thereof.

3. A compound according to claim 1, wherein:
$R^1$ is hydrogen or methyl;
$R^2$ is phenyl or pyridinyl, wherein said phenyl or pyridinyl substituted by one, two or three substituents independently selected from cyclopropylmethoxy, difluoroethoxy, dimethylamino, fluoro, methoxy, methoxypyrrolidinyl, methylsulfonylpiperazinyl, morpholinyl, oxopiperazinyl, oxopyrrolidinylpropoxy, pyrrolidinyl and tetrahydrofuranylmethoxy; and
$R^3$ is imidazolyl, oxazolyl, pyrazolyl, thiazolyl or triazolyl, wherein said imidazolyl, oxazolyl, pyrazolyl, thiazolyl or triazolyl is unsubstituted or substituted by methyl or benzyl;
or pharmaceutically acceptable salt, or an enantiomer thereof.

4. A compound according to claim 1, wherein $R^1$ is $C_{1-6}$alkyl.

5. A compound according to claim 4, wherein $R^1$ is methyl.

6. A compound according to claim 1, wherein $R^2$ is pyridinyl substituted by two substituents independently selected from $C_{3-7}$cycloalkyl$C_{1-6}$alkoxy, ($C_{1-6}$alkyl)$_2$amino, halogen, $C_{1-6}$alkoxy, $C_{1-6}$alkoxypyrrolidinyl, $C_{1-6}$alkylsulfonylpiperazinyl, oxopiperazinyl, pyrrolidinyl and tetrahydrofuranyl$C_{1-6}$alkoxy.

7. A compound according to claim 6, wherein $R^2$ is selected from:
fluoro(methoxy)pyridinyl, difluoropyridinyl, fluoro(dimethylamino)pyridinyl, fluoro(pyrrolidinyl)pyridinyl, fluoro(methylsulfonylpiperazinyl)pyridinyl, fluoro(methoxypyrrolidinyl)pyridinyl, fluoro(oxopiperazinyl)pyridinyl, fluoro(cyclopropylmethoxy)pyridinyl, fluoro(tetrahydrofuranylmethoxy)pyridinyl, fluoro(tetrahydrofuranylmethoxy)pyridinyl and methoxy(methoxypyrrolidiny)pyridinyl.

8. A compound according to claim 1, wherein $R^3$ is $C_{1-6}$alkylimidazolyl, thiazolyl or triazolyl.

9. A compound according to claim 8, wherein $R^3$ is methylimidazolyl, thiazolyl or triazolyl.

10. A compound according to claim 1, selected from:
6-(3,4-Difluoro-5-methoxy-phenyl)-2-(1-methylimidazol-2-yl)-7,8-dihydro-5H-pyrido[4,3-d]pyrimidine;
6-(6-Fluoro-4-methoxy-2-pyridyl)-5-methyl-2-(triazol-1-yl)-7,8-dihydro-5H-pyrido[4,3-d]pyrimidine;
6-(6-Fluoro-4-methoxy-2-pyridyl)-5-methyl-2-(triazol-2-yl)-7,8-dihydro-5H-pyrido[4,3-d]pyrimidine;
2-[6-(6-Fluoro-4-methoxy-2-pyridyl)-5-methyl-7,8-dihydro-5H-pyrido[4,3-d]pyrimidin-2-yl]oxazole;
4-[6-(6-Fluoro-4-methoxy-2-pyridyl)-5-methyl-7,8-dihydro-5H-pyrido[4,3-d]pyrimidin-2-yl]thiazole;
2-[6-(6-Fluoro-4-methoxy-2-pyridyl)-5-methyl-7,8-dihydro-5H-pyrido[4,3-d]pyrimidin-2-yl]thiazole;
6-(6-Fluoro-4-methoxy-2-pyridyl)-5-methyl-2-(1-methylimidazol-2-yl)-7,8-dihydro-5H-pyrido[4,3-d]pyrimidine;
6-(6-Fluoro-4-methoxy-2-pyridyl)-5-methyl-2-(1-methylimidazol-4-yl)-7,8-dihydro-5H-pyrido[4,3-d]pyrimidine;
6-(6-Fluoro-4-methoxy-2-pyridyl) -5-methyl-2-pyrazol-1-yl-7,8-dihydro-5H-pyrido[4,3-d]pyrimidine;
2-(1-Benzylimidazol-4-yl)-6-(6-fluoro-4-methoxy-2-pyridyl)-5-methyl-7,8-dihydro-5H-pyrido[4,3-d]pyrimidine;
2-Fluoro-N,N-dimethyl-6-(5-methyl-2-thiazol-4-yl-7,8-dihydro-5H-pyrido[4,3-d]pyrimidin-6-yl)pyridin-4-amine;
4-[6-Fluoro-4-(5-methyl-2-thiazol-4-yl-7,8-dihydro-5H-pyrido[4,3-d]pyrimidin-6-yl)-2-pyridyl]morpholine;
4-[2-Fluoro-6-(5-methyl-2-thiazol-4-yl-7,8-dihydro-5H-pyrido[4,3-d]pyrimidin-6-yl)-4-pyridyl]morpholine;
4-[4-Fluoro-6-(5-methyl-2-thiazol-4-yl-7,8-dihydro-5H-pyrido[4,3-d]pyrimidin-6-yl)-2-pyridyl]morpholine;

4-[6-(6-Fluoro-4-methoxy-2-pyridyl)-5-methyl-7,8-dihydro-5H-pyrido[4,3-d]pyrimidin-2-yl]-2-methyl-thiazole;

5-[6-(6-Fluoro-4-methoxy-2-pyridyl)-5-methyl-7,8-dihydro-5H-pyrido[4,3-d]pyrimidin-2-yl]-2-methyl-thiazole;

4-[6-(2-Fluoro-6-pyrrolidin-1-yl-4-pyridyl)-5-methyl-7,8-dihydro-5H-pyrido[4,3-d]pyrimidin-2-yl]thiazole;

4-[6-(6-Fluoro-4-pyrrolidin-1-yl-2-pyridyl)-5-methyl-7,8-dihydro-5H-pyrido[4,3-d]pyrimidin-2-yl]thiazole;

4-[6-(4-Fluoro-6-pyrrolidin-1-yl-2-pyridyl)-5-methyl-7,8-dihydro-5H-pyrido[4,3-d]pyrimidin-2-yl]thiazole;

4-[6-[2-Fluoro-6-(4-methylsulfonylpiperazin-1-yl)-4-pyridyl]-5-methyl-7,8-dihydro-5H-pyrido[4,3-d]pyrimidin-2-yl]thiazole;

4-[6-[6-Fluoro-4-(4-methylsulfonylpiperazin-1-yl)-2-pyridyl]-5-methyl-7,8-dihydro-5H-pyrido[4,3-d]pyrimidin-2-yl]thiazole;

4-[6-[4-Fluoro-6-(4-methylsulfonylpiperazin-1-yl)-2-pyridyl]-5-methyl-7,8-dihydro-5H-pyrido[4,3-d]pyrimidin-2-yl]thiazole;

4-[6-[2-Fluoro-6-(3-methoxypyrrolidin-1-yl)-4-pyridyl]-5-methyl-7,8-dihydro-5H-pyrido[4,3-d]pyrimidin-2-yl]thiazole;

4-[6-[6-Fluoro-4-(3-methoxypyrrolidin-1-yl)-2-pyridyl]-5-methyl-7,8-dihydro-5H-pyrido[4,3-d]pyrimidin-2-yl]thiazole;

4-[6-[4-Fluoro-6-(3-methoxypyrrolidin-1-yl)-2-pyridyl]-5-methyl-7,8-dihydro-5H-pyrido[4,3-d]pyrimidin-2-yl]thiazole;

6-(6-Fluoro-4-methoxy-2-pyridyl)-2-(1H-imidazol-2-yl)-5-methyl-7,8-dihydro-5H-pyrido[4,3-d]pyrimidine;

6-(6-Fluoro-4-methoxy-2-pyridyl)-5-methyl-2-(1H-pyrazol-3-yl)-7,8-dihydro-5H-pyrido[4,3-d]pyrimidine;

4-[6-Fluoro-4-(5-methyl-2-thiazol-4-yl-7,8-dihydro-5H-pyrido[4,3-d]pyrimidin-6-yl)-2-pyridyl]piperazin-2-one;

4-[2-Fluoro-6-(5-methyl-2-thiazol-4-yl-7,8-dihydro-5H-pyrido[4,3-d]pyrimidin-6-yl)-4-pyridyl]piperazin-2-one;

4-[4-Fluoro-6-(5-methyl-2-thiazol-4-yl-7,8-dihydro-5H-pyrido[4,3-d]pyrimidin-6-yl)-2-pyridyl]piperazin-2-one;

4-[6-[2-(Cyclopropylmethoxy)-6-fluoro-4-pyridyl]-5-methyl-7,8-dihydro-5H-pyrido[4,3-d]pyrimidin-2-yl]thiazole;

4-[6-[4-(Cyclopropylmethoxy)-6-fluoro-2-pyridyl]-5-methyl-7,8-dihydro-5H-pyrido[4,3-d]pyrimidin-2-yl]thiazole;

4-[6-[6-(Cyclopropylmethoxy)-4-fluoro-2-pyridyl]-5-methyl-7,8-dihydro-5H-pyrido[4,3-d]pyrimidin-2-yl]thiazole;

4-[6-[2-(2,2-Difluoroethoxy)-6-fluoro-4-pyridyl]-5-methyl-7,8-dihydro-5H-pyrido[4,3-d]pyrimidin-2-yl]thiazole;

4-[6-[4-(2,2-Difluoroethoxy)-6-fluoro-2-pyridyl]-5-methyl-7,8-dihydro-5H-pyrido[4,3-d]pyrimidin-2-yl]thiazole;

4-[6-[6-(2,2-Difluoroethoxy)-4-fluoro-2-pyridyl]-5-methyl-7,8-dihydro-5H-pyrido[4,3-d]pyrimidin-2-yl]thiazole;

4-[6-[2-Fluoro-6-(tetrahydrofuran-3-ylmethoxy)-4-pyridyl]-5-methyl-7,8-dihydro-5H-pyrido[4,3-d]pyrimidin-2-yl]thiazole;

4-[6-[6-Fluoro-4-(tetrahydrofuran-3-ylmethoxy)-2-pyridyl]-5-methyl-7,8-dihydro-5H-pyrido[4,3-d]pyrimidin-2-yl]thiazole;

4-[6-[4-Fluoro-6-(tetrahydrofuran-3-ylmethoxy)-2-pyridyl]-5-methyl-7,8-dihydro-5H-pyrido[4,3-d]pyrimidin-2-yl]thiazole;

1-[3-[[6-Fluoro-4-(5-methyl-2-thiazol-4-yl-7,8-dihydro-5H-pyrido[4,3-d]pyrimidin-6-yl)-2-pyridyl]oxy]propyl]pyrrolidin-2-one;

1-[3-[[2-Fluoro-6-(5-methyl-2-thiazol-4-yl-7,8-dihydro-5H-pyrido[4,3-d]pyrimidin-6-yl)-4-pyridyl]oxy]propyl]pyrrolidin-2-one;

4-[6-(6-Fluoro-4-methoxy-2-pyridyl)-5-methyl-7,8-dihydro-5H-pyrido[4,3-d]pyrimidin-2-yl]-5-methyl-thiazole; and 6-(6-Fluoro-4-methoxy-2-pyridyl)-5-methyl-2-(1H-1,2,4-triazol-5-yl)-7,8-dihydro-5H-pyrido[4,3-d]pyrimidine;

or a pharmaceutically acceptable salt, or an enantiomer thereof.

11. A compound according to claim 1, selected from:
4-[6-(6-Fluoro-4-methoxy-2-pyridyl)-5-methyl-7,8-dihydro-5H-pyrido[4,3-d]pyrimidin-2-yl]thiazole;
6-(6-Fluoro-4-methoxy-2-pyridyl)-5-methyl-2-(1-methylimidazol-4-yl)-7,8-dihydro-5H-pyrido[4,3-d]pyrimidine;
2-Fluoro-N,N-dimethyl-6-(5-methyl-2-thiazol-4-yl-7,8-dihydro-5H-pyrido[4,3-d]pyrimidin-6-yl)pyridin-4-amine;
4-[6-(6-Fluoro-4-pyrrolidin-1-yl-2-pyridyl)-5-methyl-7,8-dihydro-5H-pyrido[4,3-d]pyrimidin-2-yl]thiazole;
4-[6-[2-Fluoro-6-(4-methylsulfonylpiperazin-1-yl)-4-pyridyl]-5-methyl-7,8-dihydro-5H-pyrido[4,3-d]pyrimidin-2-yl]thiazole;
4-[6-[2-Fluoro-6-(3-methoxypyrrolidin-1-yl)-4-pyridyl]-5-methyl-7,8-dihydro-5H-pyrido[4,3-d]pyrimidin-2-yl]thiazole;
4-[6-[4-Fluoro-6-(3-methoxypyrrolidin-1-yl)-2-pyridyl]-5-methyl-7,8-dihydro-5H-pyrido[4,3-d]pyrimidin-2-yl]thiazole;
4-[2-Fluoro-6-(5-methyl-2-thiazol-4-yl-7,8-dihydro-5H-pyrido[4,3-d]pyrimidin-6-yl)-4-pyridyl]piperazin-2-one;
4-[6-[4-(Cyclopropylmethoxy)-6-fluoro-2-pyridyl]-5-methyl-7,8-dihydro-5H-pyrido[4,3-d]pyrimidin-2-yl]thiazole;
4-[6-[2-Fluoro-6-(tetrahydrofuran-3-ylmethoxy)-4-pyridyl]-5-methyl-7,8-dihydro-5H-pyrido[4,3-d]pyrimidin-2-yl]thiazole;
4-[6-[6-Fluoro-4-(tetrahydrofuran-3-ylmethoxy)-2-pyridyl]-5-methyl-7,8-dihydro-5H-pyrido[4,3-d]pyrimidin-2-yl]thiazole; and
6-(6-Fluoro-4-methoxy-2-pyridyl)-5-methyl-2-(1H-1,2,4-triazol-5-yl)-7,8-dihydro-5H-pyrido[4,3-d]pyrimidine;

or a pharmaceutically acceptable salt, or an enantiomer thereof.

12. A process for the preparation of a compound according to claim 1, the method comprising:
(a) cyclization a compound of formula (A)

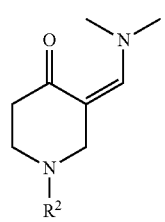

(A)

with a compound of formula (B)

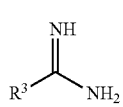 (B)

in the presence of a base;
(b) coupling of a compound of formula (C)

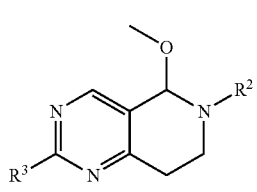 (C)

with a nucleophile in the presence of a Lewis acid;
wherein the nucleophile is a Grignard reagent or dialkylzinc reagent.

13. A pharmaceutical composition comprising a compound in accordance with claim 1 and a therapeutically inert carrier.

14. A method for the treatment of HBV infection, which method comprises administering to a subject in need thereof an effective amount of a compound as defined in claim 1.

* * * * *